(12) United States Patent
Horowitz et al.

(10) Patent No.: US 11,461,966 B1
(45) Date of Patent: Oct. 4, 2022

(54) DETERMINING SPANS AND SPAN LENGTHS OF A CONTROL OBJECT IN A FREE SPACE GESTURE CONTROL ENVIRONMENT

(71) Applicant: Ultrahaptics IP Two Limited, Bristol (GB)

(72) Inventors: Kevin A Horowitz, San Francisco, CA (US); David S Holz, San Francisco, CA (US)

(73) Assignee: Ultrahaptics IP Two Limited, Bristol (GB)

( * ) Notice: Subject to any disclaimer, the term of this patent is extended or adjusted under 35 U.S.C. 154(b) by 95 days.

(21) Appl. No.: 17/100,786

(22) Filed: Nov. 20, 2020

Related U.S. Application Data

(63) Continuation of application No. 14/474,077, filed on Aug. 29, 2014, now Pat. No. 10,846,942.
(Continued)

(51) Int. Cl.
*G06F 3/01* (2006.01)
*G06T 17/10* (2006.01)
(Continued)

(52) U.S. Cl.
CPC .............. *G06T 17/10* (2013.01); *G06F 3/011* (2013.01); *G06F 3/017* (2013.01); *G06T 7/11* (2017.01);
(Continued)

(58) Field of Classification Search
CPC ...... G06F 3/017; G06F 3/011; G06F 3/04883; G06F 3/0488; A61B 34/10; G06T 19/006;
(Continued)

(56) References Cited

U.S. PATENT DOCUMENTS 2,665,041 A   1/1954  Maffucci
4,175,862 A   11/1979 DiMatteo et al.
(Continued)

FOREIGN PATENT DOCUMENTS

CN    1984236 A    6/2007
CN   201332447 Y  10/2009
(Continued)

OTHER PUBLICATIONS

Kim et al., RetroDepth: 3D Silhouette Sensing for High-Precision Input On and Above Physical Surfaces, Apr. 26, 2014 [retrieved Jun. 12, 2022], CHI '14: Proceedings of the SIGCHI Conference on Human Factors in Computing Systems, pp. 1377-1386. Retrieved: (Year: 2014) https://dl.acm.org/doi/abs/10.1145/2556288.2557336 (Year: 2014).*

(Continued)

*Primary Examiner* — Matthew C Bella
*Assistant Examiner* — Dennis Rosario
(74) *Attorney, Agent, or Firm* — Haynes Beffel & Wolfeld LLP; Andrew L. Dunlap

(57) ABSTRACT

Free space machine interface and control can be facilitated by predictive entities useful in interpreting a control object's position and/or motion (including objects having one or more articulating members, i.e., humans and/or animals and/or machines). Predictive entities can be driven using motion information captured using image information or the equivalents. Predictive information can be improved applying techniques for correlating with information from observations.

20 Claims, 20 Drawing Sheets

Related U.S. Application Data

(60) Provisional application No. 61/898,462, filed on Oct. 31, 2013, provisional application No. 61/873,758, filed on Sep. 4, 2013, provisional application No. 61/871,790, filed on Aug. 29, 2013.

(51) Int. Cl.

| | |
|---|---|
| *G06T 7/593* | (2017.01) |
| *G06T 7/11* | (2017.01) |
| *G06T 7/246* | (2017.01) |
| *G06T 7/194* | (2017.01) |
| *G06T 7/136* | (2017.01) |
| *G06T 19/00* | (2011.01) |
| *G06T 19/20* | (2011.01) |
| *G06T 17/20* | (2006.01) |
| *G06V 40/20* | (2022.01) |

(52) U.S. Cl.
CPC .............. *G06T 7/136* (2017.01); *G06T 7/194* (2017.01); *G06T 7/251* (2017.01); *G06T 7/593* (2017.01); *G06T 17/20* (2013.01); *G06T 19/006* (2013.01); *G06T 19/20* (2013.01); *G06V 40/28* (2022.01); *G06T 19/00* (2013.01); *G06T 2207/10028* (2013.01); *G06T 2207/20048* (2013.01); *G06T 2219/2004* (2013.01); *G06T 2219/2016* (2013.01); *G06T 2219/2021* (2013.01)

(58) Field of Classification Search
CPC ....... G06T 17/00; G06T 7/12; G06T 2200/08; G06T 7/13; G06T 7/10; G06V 40/28; G06V 40/113; G06V 40/11; G06V 40/107; G06V 40/20; H04N 13/332
See application file for complete search history.

(56) References Cited

U.S. PATENT DOCUMENTS

| | | | |
|---|---|---|---|
| 4,876,455 A | 10/1989 | Sanderson et al. | |
| 4,879,659 A | 11/1989 | Bowlin et al. | |
| 4,893,223 A | 1/1990 | Arnold | |
| 5,038,258 A | 8/1991 | Koch et al. | |
| 5,134,661 A | 7/1992 | Reinsch | |
| 5,282,067 A | 1/1994 | Liu | |
| 5,434,617 A | 7/1995 | Bianchi | |
| 5,454,043 A | 9/1995 | Freeman | |
| 5,574,511 A | 11/1996 | Yang et al. | |
| 5,581,276 A | 12/1996 | Cipolla et al. | |
| 5,594,469 A | 1/1997 | Freeman et al. | |
| 5,659,475 A | 8/1997 | Brown | |
| 5,691,737 A | 11/1997 | Ito et al. | |
| 5,742,263 A | 4/1998 | Wang et al. | |
| 5,900,863 A | 5/1999 | Numazaki | |
| 5,940,538 A | 8/1999 | Spiegel et al. | |
| 6,002,808 A | 12/1999 | Freeman | |
| 6,031,161 A | 2/2000 | Baltenberger | |
| 6,031,661 A | 2/2000 | Tanaami | |
| 6,072,494 A | 6/2000 | Nguyen | |
| 6,075,895 A | 6/2000 | Qiao et al. | |
| 6,147,678 A | 11/2000 | Kumar et al. | |
| 6,154,558 A | 11/2000 | Hsieh | |
| 6,181,343 B1 | 1/2001 | Lyons | |
| 6,184,326 B1 | 2/2001 | Razavi et al. | |
| 6,184,926 B1 | 2/2001 | Khosravi et al. | |
| 6,195,104 B1 | 2/2001 | Lyons | |
| 6,204,852 B1 | 3/2001 | Kumar et al. | |
| 6,252,598 B1 | 6/2001 | Segen | |
| 6,263,091 B1 | 7/2001 | Jain et al. | |
| 6,346,933 B1 | 2/2002 | Lin | |
| 6,417,970 B1 | 7/2002 | Travers et al. | |
| 6,463,402 B1 | 10/2002 | Bennett et al. | |
| 6,492,986 B1 | 12/2002 | Metaxas et al. | |
| 6,493,041 B1 | 12/2002 | Hanko et al. | |
| 6,498,628 B2 | 12/2002 | Iwamura | |
| 6,578,203 B1 | 6/2003 | Anderson, Jr. et al. | |
| 6,597,801 B1 | 7/2003 | Cham et al. | |
| 6,603,867 B1 | 8/2003 | Sugino et al. | |
| 6,661,918 B1 | 12/2003 | Gordon et al. | |
| 6,674,877 B1 | 1/2004 | Jojic et al. | |
| 6,702,494 B2 | 3/2004 | Dumler et al. | |
| 6,734,911 B1 | 5/2004 | Lyons | |
| 6,738,424 B1 | 5/2004 | Allmen et al. | |
| 6,771,294 B1 | 8/2004 | Pulli et al. | |
| 6,798,628 B1 | 9/2004 | Macbeth | |
| 6,804,654 B2 | 10/2004 | Kobylevsky et al. | |
| 6,804,656 B1 | 10/2004 | Rosenfeld et al. | |
| 6,814,656 B2 | 11/2004 | Rodriguez | |
| 6,819,796 B2 | 11/2004 | Hong et al. | |
| 6,919,880 B2 | 7/2005 | Morrison et al. | |
| 6,950,534 B2 | 9/2005 | Cohen et al. | |
| 6,993,157 B1 | 1/2006 | Oue et al. | |
| 7,152,024 B2 | 12/2006 | Marschner et al. | |
| 7,213,707 B2 | 5/2007 | Hubbs et al. | |
| 7,215,828 B2 | 5/2007 | Luo | |
| 7,244,233 B2 | 7/2007 | Krantz et al. | |
| 7,257,237 B1 | 8/2007 | Luck et al. | |
| 7,259,873 B2 | 8/2007 | Sikora et al. | |
| 7,308,112 B2 | 12/2007 | Fujimura et al. | |
| 7,340,077 B2 | 3/2008 | Gokturk et al. | |
| 7,472,047 B2 | 12/2008 | Kramer et al. | |
| 7,483,049 B2 | 1/2009 | Aman et al. | |
| 7,519,223 B2 | 4/2009 | Dehlin et al. | |
| 7,532,206 B2 | 5/2009 | Morrison et al. | |
| 7,536,032 B2 | 5/2009 | Bell | |
| 7,542,586 B2 | 6/2009 | Johnson | |
| 7,598,942 B2 | 10/2009 | Underkoffler et al. | |
| 7,606,417 B2 | 10/2009 | Steinberg et al. | |
| 7,646,372 B2 | 1/2010 | Marks et al. | |
| 7,656,372 B2 | 2/2010 | Sato et al. | |
| 7,665,041 B2 | 2/2010 | Wilson et al. | |
| 7,692,625 B2 | 4/2010 | Morrison et al. | |
| 7,769,994 B2 | 8/2010 | Peles | |
| 7,831,932 B2 | 11/2010 | Josephsoon et al. | |
| 7,840,031 B2 | 11/2010 | Albertson et al. | |
| 7,861,188 B2 | 12/2010 | Josephsoon et al. | |
| 7,940,885 B2 | 5/2011 | Stanton et al. | |
| 7,948,493 B2 | 5/2011 | Klefenz et al. | |
| 7,961,934 B2 | 6/2011 | Thrun et al. | |
| 7,971,156 B2 | 6/2011 | Albertson et al. | |
| 7,980,885 B2 | 7/2011 | Gattwinkel et al. | |
| 8,005,263 B2 * | 8/2011 | Fujimura ............... | G06V 20/64 382/103 |
| 8,023,698 B2 | 9/2011 | Niwa et al. | |
| 8,035,624 B2 | 10/2011 | Bell et al. | |
| 8,045,825 B2 | 10/2011 | Shimoyama et al. | |
| 8,064,704 B2 | 11/2011 | Kim et al. | |
| 8,085,339 B2 | 12/2011 | Marks | |
| 8,086,971 B2 | 12/2011 | Radivojevic et al. | |
| 8,111,239 B2 | 2/2012 | Pryor et al. | |
| 8,112,719 B2 | 2/2012 | Hsu et al. | |
| 8,144,233 B2 | 3/2012 | Fukuyama | |
| 8,185,176 B2 | 5/2012 | Mangat et al. | |
| 8,213,707 B2 | 7/2012 | Li et al. | |
| 8,218,858 B2 | 7/2012 | Gu | |
| 8,229,134 B2 | 7/2012 | Duraiswami et al. | |
| 8,244,233 B2 | 8/2012 | Chang et al. | |
| 8,249,345 B2 | 8/2012 | Wu et al. | |
| 8,270,669 B2 | 9/2012 | Aichi et al. | |
| 8,289,162 B2 | 10/2012 | Mooring et al. | |
| 8,290,208 B2 | 10/2012 | Kurtz et al. | |
| 8,304,727 B2 | 11/2012 | Lee et al. | |
| 8,319,832 B2 | 11/2012 | Nagata et al. | |
| 8,363,010 B2 | 1/2013 | Nagata | |
| 8,395,600 B2 | 3/2013 | Kawashima et al. | |
| 8,514,221 B2 | 8/2013 | King et al. | |
| 8,553,037 B2 | 10/2013 | Smith et al. | |
| 8,582,809 B2 | 11/2013 | Halimeh et al. | |
| 8,593,417 B2 | 11/2013 | Kawashima et al. | |
| 8,620,024 B2 | 12/2013 | Huang et al. | |
| 8,631,355 B2 | 1/2014 | Murillo et al. | |
| 8,638,989 B2 | 1/2014 | Holz | |

(56) References Cited

U.S. PATENT DOCUMENTS

| | | |
|---|---|---|
| 8,659,594 B2 | 2/2014 | Kim et al. |
| 8,659,658 B2 | 2/2014 | Vassigh et al. |
| 8,693,731 B2 | 4/2014 | Holz et al. |
| 8,738,523 B1 | 5/2014 | Sanchez et al. |
| 8,744,122 B2 | 6/2014 | Salgian et al. |
| 8,768,022 B2 | 7/2014 | Miga et al. |
| 8,817,087 B2 | 8/2014 | Weng et al. |
| 8,842,084 B2 | 9/2014 | Andersson et al. |
| 8,843,857 B2 | 9/2014 | Berkes et al. |
| 8,872,914 B2 | 10/2014 | Gobush |
| 8,878,749 B1 | 11/2014 | Wu et al. |
| 8,891,868 B1 | 11/2014 | Ivanchenko |
| 8,907,982 B2 | 12/2014 | Zontrop et al. |
| 8,922,590 B1 | 12/2014 | Luckett, Jr. et al. |
| 8,929,609 B2 | 1/2015 | Padovani et al. |
| 8,930,852 B2 | 1/2015 | Chen et al. |
| 8,942,881 B2 | 1/2015 | Hobbs et al. |
| 8,954,340 B2 | 2/2015 | Sanchez et al. |
| 8,957,857 B2 | 2/2015 | Lee et al. |
| 9,014,414 B2 | 4/2015 | Katano et al. |
| 9,056,396 B1 | 6/2015 | Linnell |
| 9,070,019 B2 | 6/2015 | Holz |
| 9,119,670 B2 | 9/2015 | Yang et al. |
| 9,122,354 B2 | 9/2015 | Sharma |
| 9,124,778 B1 | 9/2015 | Crabtree |
| 9,135,503 B2 | 9/2015 | Sundaresan et al. |
| 9,305,229 B2 | 4/2016 | DeLean et al. |
| 9,721,383 B1 | 8/2017 | Horowitz et al. |
| 2001/0044858 A1 | 11/2001 | Rekimoto |
| 2002/0008211 A1 | 1/2002 | Kask |
| 2002/0080094 A1 | 6/2002 | Biocca et al. |
| 2002/0105484 A1 | 8/2002 | Navab et al. |
| 2003/0053658 A1 | 3/2003 | Pavlidis |
| 2003/0053659 A1 | 3/2003 | Pavlidis et al. |
| 2003/0123703 A1 | 7/2003 | Pavlidis et al. |
| 2003/0152289 A1 | 8/2003 | Luo |
| 2003/0202697 A1 | 10/2003 | Simard et al. |
| 2004/0103111 A1 | 5/2004 | Miller et al. |
| 2004/0125228 A1 | 7/2004 | Dougherty |
| 2004/0125984 A1 | 7/2004 | Ito et al. |
| 2004/0145809 A1 | 7/2004 | Brenner |
| 2004/0155877 A1 | 8/2004 | Hong et al. |
| 2004/0212725 A1 | 10/2004 | Raskar |
| 2005/0007673 A1 | 1/2005 | Chaoulov et al. |
| 2005/0068518 A1 | 3/2005 | Baney et al. |
| 2005/0094019 A1 | 5/2005 | Grosvenor et al. |
| 2005/0131607 A1 | 6/2005 | Breed |
| 2005/0156888 A1 | 7/2005 | Xie et al. |
| 2005/0168578 A1 | 8/2005 | Gobush |
| 2005/0236558 A1 | 10/2005 | Nabeshima et al. |
| 2005/0271279 A1* | 12/2005 | Fujimura ............ G06V 40/28 382/209 |
| 2006/0017807 A1 | 1/2006 | Lee et al. |
| 2006/0029296 A1 | 2/2006 | King et al. |
| 2006/0034545 A1 | 2/2006 | Mattes et al. |
| 2006/0050979 A1 | 3/2006 | Kawahara |
| 2006/0072105 A1 | 4/2006 | Wagner |
| 2006/0098899 A1 | 5/2006 | King et al. |
| 2006/0204040 A1 | 9/2006 | Freeman et al. |
| 2006/0210112 A1 | 9/2006 | Cohen et al. |
| 2006/0290950 A1 | 12/2006 | Platt et al. |
| 2007/0014466 A1 | 1/2007 | Baldwin |
| 2007/0042346 A1 | 2/2007 | Weller |
| 2007/0086621 A1 | 4/2007 | Aggarwal et al. |
| 2007/0130547 A1 | 6/2007 | Boillot |
| 2007/0206719 A1 | 9/2007 | Suryanarayanan et al. |
| 2007/0230929 A1 | 10/2007 | Niwa et al. |
| 2007/0238956 A1 | 10/2007 | Haras et al. |
| 2008/0013826 A1 | 1/2008 | Hillis et al. |
| 2008/0019576 A1 | 1/2008 | Senftner et al. |
| 2008/0030429 A1 | 2/2008 | Hailpern et al. |
| 2008/0031492 A1 | 2/2008 | Lanz |
| 2008/0056752 A1 | 3/2008 | Denton et al. |
| 2008/0064954 A1 | 3/2008 | Adams et al. |
| 2008/0106637 A1 | 5/2008 | Nakao et al. |
| 2008/0106746 A1 | 5/2008 | Shpunt et al. |
| 2008/0110994 A1 | 5/2008 | Knowles et al. |
| 2008/0118091 A1 | 5/2008 | Serfaty et al. |
| 2008/0126937 A1 | 5/2008 | Pachet |
| 2008/0187175 A1 | 8/2008 | Kim et al. |
| 2008/0244468 A1 | 10/2008 | Nishihara et al. |
| 2008/0246759 A1 | 10/2008 | Summers |
| 2008/0273764 A1 | 11/2008 | Scholl |
| 2008/0278589 A1 | 11/2008 | Thorn |
| 2008/0291160 A1 | 11/2008 | Rabin |
| 2008/0304740 A1 | 12/2008 | Sun et al. |
| 2008/0319356 A1 | 12/2008 | Cain et al. |
| 2009/0002489 A1 | 1/2009 | Yang et al. |
| 2009/0093307 A1 | 4/2009 | Miyaki |
| 2009/0102840 A1 | 4/2009 | Li |
| 2009/0116742 A1 | 5/2009 | Nishihara |
| 2009/0122146 A1 | 5/2009 | Zalewski et al. |
| 2009/0153655 A1 | 6/2009 | Ike et al. |
| 2009/0203993 A1 | 8/2009 | Mangat et al. |
| 2009/0203994 A1 | 8/2009 | Mangat et al. |
| 2009/0217211 A1 | 8/2009 | Hildreth et al. |
| 2009/0257623 A1 | 10/2009 | Tang et al. |
| 2009/0274339 A9 | 11/2009 | Cohen et al. |
| 2009/0309710 A1 | 12/2009 | Kakinami |
| 2010/0013832 A1 | 1/2010 | Xiao et al. |
| 2010/0020078 A1 | 1/2010 | Shpunt |
| 2010/0023015 A1 | 1/2010 | Park |
| 2010/0026963 A1 | 2/2010 | Faulstich |
| 2010/0027845 A1 | 2/2010 | Kim et al. |
| 2010/0046842 A1 | 2/2010 | Conwell |
| 2010/0053164 A1 | 3/2010 | Imai et al. |
| 2010/0053209 A1 | 3/2010 | Rauch et al. |
| 2010/0058252 A1 | 3/2010 | Ko |
| 2010/0066737 A1 | 3/2010 | Liu |
| 2010/0066975 A1 | 3/2010 | Rehnstrom |
| 2010/0091110 A1 | 4/2010 | Hildreth |
| 2010/0118123 A1 | 5/2010 | Freedman et al. |
| 2010/0121189 A1 | 5/2010 | Ma et al. |
| 2010/0125815 A1 | 5/2010 | Wang et al. |
| 2010/0127995 A1 | 5/2010 | Rigazio et al. |
| 2010/0141762 A1 | 6/2010 | Siann et al. |
| 2010/0158372 A1 | 6/2010 | Kim et al. |
| 2010/0177929 A1 | 7/2010 | Kurtz et al. |
| 2010/0194863 A1 | 8/2010 | Lopes et al. |
| 2010/0199232 A1 | 8/2010 | Mistry et al. |
| 2010/0201880 A1 | 8/2010 | Iwamura |
| 2010/0208942 A1 | 8/2010 | Porter et al. |
| 2010/0219934 A1 | 9/2010 | Matsumoto |
| 2010/0222102 A1 | 9/2010 | Rodriguez |
| 2010/0264833 A1 | 10/2010 | Van Endert et al. |
| 2010/0277411 A1 | 11/2010 | Yee et al. |
| 2010/0296698 A1 | 11/2010 | Lien et al. |
| 2010/0302357 A1 | 12/2010 | Hsu et al. |
| 2010/0303298 A1 | 12/2010 | Marks et al. |
| 2010/0306712 A1 | 12/2010 | Snook et al. |
| 2010/0309097 A1 | 12/2010 | Raviv et al. |
| 2010/0329509 A1 | 12/2010 | Fahn et al. |
| 2011/0007072 A1 | 1/2011 | Khan et al. |
| 2011/0025818 A1 | 2/2011 | Gallmeier et al. |
| 2011/0026765 A1 | 2/2011 | Ivanich et al. |
| 2011/0043806 A1 | 2/2011 | Guetta et al. |
| 2011/0057875 A1 | 3/2011 | Shigeta et al. |
| 2011/0080470 A1 | 4/2011 | Kuno et al. |
| 2011/0080490 A1 | 4/2011 | Clarkson et al. |
| 2011/0093820 A1 | 4/2011 | Zhang et al. |
| 2011/0107216 A1 | 5/2011 | Bi |
| 2011/0115486 A1 | 5/2011 | Frohlich et al. |
| 2011/0116684 A1 | 5/2011 | Coffman et al. |
| 2011/0119640 A1 | 5/2011 | Berkes et al. |
| 2011/0134112 A1 | 6/2011 | Koh et al. |
| 2011/0148875 A1 | 6/2011 | Kim et al. |
| 2011/0169726 A1 | 7/2011 | Holmdahl et al. |
| 2011/0173574 A1 | 7/2011 | Clavin et al. |
| 2011/0181509 A1 | 7/2011 | Rautiainen et al. |
| 2011/0193778 A1 | 8/2011 | Lee et al. |
| 2011/0205151 A1 | 8/2011 | Newton et al. |
| 2011/0213664 A1 | 9/2011 | Osterhout et al. |
| 2011/0228978 A1 | 9/2011 | Chen et al. |
| 2011/0234840 A1 | 9/2011 | Klefenz et al. |

(56) References Cited

U.S. PATENT DOCUMENTS

| | | |
|---|---|---|
| 2011/0243451 A1 | 10/2011 | Oyaizu |
| 2011/0261178 A1 | 10/2011 | Lo et al. |
| 2011/0267259 A1 | 11/2011 | Tidemand et al. |
| 2011/0279397 A1 | 11/2011 | Rimon et al. |
| 2011/0286676 A1 | 11/2011 | El Dokor |
| 2011/0289455 A1 | 11/2011 | Reville et al. |
| 2011/0289456 A1 | 11/2011 | Reville et al. |
| 2011/0291925 A1 | 12/2011 | Israel et al. |
| 2011/0291988 A1 | 12/2011 | Bamji et al. |
| 2011/0296353 A1 | 12/2011 | Ahmed et al. |
| 2011/0299737 A1 | 12/2011 | Wang et al. |
| 2011/0304650 A1 | 12/2011 | Campillo et al. |
| 2011/0310007 A1 | 12/2011 | Margolis et al. |
| 2011/0310220 A1 | 12/2011 | McEldowney |
| 2011/0314427 A1 | 12/2011 | Sundararajan |
| 2012/0038637 A1 | 2/2012 | Marks |
| 2012/0050157 A1 | 3/2012 | Latta et al. |
| 2012/0062736 A1 * | 3/2012 | Xiong ............... G06F 3/0425 382/199 |
| 2012/0065499 A1 | 3/2012 | Chono |
| 2012/0068914 A1 | 3/2012 | Jacobsen et al. |
| 2012/0159380 A1 | 6/2012 | Kocienda et al. |
| 2012/0163675 A1 | 6/2012 | Joo et al. |
| 2012/0194517 A1 | 8/2012 | Izadi et al. |
| 2012/0204133 A1 | 8/2012 | Guendelman et al. |
| 2012/0223959 A1 | 9/2012 | Lengeling |
| 2012/0236288 A1 | 9/2012 | Stanley |
| 2012/0250936 A1 | 10/2012 | Holmgren |
| 2012/0270654 A1 | 10/2012 | Padovani et al. |
| 2012/0274781 A1 | 11/2012 | Shet et al. |
| 2012/0281873 A1 | 11/2012 | Brown et al. |
| 2012/0293667 A1 | 11/2012 | Baba et al. |
| 2012/0314030 A1 | 12/2012 | Datta et al. |
| 2013/0019204 A1 | 1/2013 | Kotler et al. |
| 2013/0038694 A1 | 2/2013 | Nichani et al. |
| 2013/0044951 A1 | 2/2013 | Cherng et al. |
| 2013/0050425 A1 | 2/2013 | Im et al. |
| 2013/0086531 A1 | 4/2013 | Sugita et al. |
| 2013/0097566 A1 | 4/2013 | Berglund |
| 2013/0120319 A1 | 5/2013 | Givon |
| 2013/0148852 A1 | 6/2013 | Partis et al. |
| 2013/0182902 A1 | 7/2013 | Holz |
| 2013/0187952 A1 | 7/2013 | Berkovich et al. |
| 2013/0208948 A1 | 8/2013 | Berkovich et al. |
| 2013/0239059 A1 | 9/2013 | Chen et al. |
| 2013/0241832 A1 | 9/2013 | Rimon et al. |
| 2013/0252691 A1 | 9/2013 | Alexopoulos |
| 2013/0257736 A1 | 10/2013 | Hou et al. |
| 2013/0271397 A1 | 10/2013 | MacDougall et al. |
| 2013/0300831 A1 | 11/2013 | Mavromatis et al. |
| 2014/0010441 A1 | 1/2014 | Shamaie |
| 2014/0064566 A1 | 3/2014 | Shreve et al. |
| 2014/0081521 A1 | 3/2014 | Frojdh et al. |
| 2014/0085203 A1 | 3/2014 | Kobayashi |
| 2014/0125775 A1 | 5/2014 | Holz |
| 2014/0132738 A1 | 5/2014 | Ogura et al. |
| 2014/0139425 A1 | 5/2014 | Sakai |
| 2014/0139641 A1 | 5/2014 | Holz |
| 2014/0161311 A1 | 6/2014 | Kim |
| 2014/0168062 A1 | 6/2014 | Katz et al. |
| 2014/0176420 A1 | 6/2014 | Zhou et al. |
| 2014/0177913 A1 | 6/2014 | Holz |
| 2014/0189579 A1 | 7/2014 | Rimon et al. |
| 2014/0192024 A1 | 7/2014 | Holz |
| 2014/0222385 A1 | 8/2014 | Muenster et al. |
| 2014/0225826 A1 | 8/2014 | Juni |
| 2014/0240225 A1 | 8/2014 | Eilat |
| 2014/0248950 A1 | 9/2014 | Tosas Bautista |
| 2014/0253512 A1 | 9/2014 | Narikawa et al. |
| 2014/0253785 A1 | 9/2014 | Chan et al. |
| 2014/0267098 A1 | 9/2014 | Na et al. |
| 2014/0307920 A1 | 10/2014 | Holz |
| 2014/0364209 A1 | 12/2014 | Perry |
| 2014/0364212 A1 | 12/2014 | Osman et al. |
| 2014/0375547 A1 | 12/2014 | Katz et al. |
| 2015/0003673 A1 | 1/2015 | Fletcher |
| 2015/0009149 A1 | 1/2015 | Gharib et al. |
| 2015/0016777 A1 | 1/2015 | Abovitz et al. |
| 2015/0022447 A1 | 1/2015 | Hare et al. |
| 2015/0029091 A1 | 1/2015 | Nakashima et al. |
| 2015/0097772 A1 | 4/2015 | Starner |
| 2015/0115802 A1 | 4/2015 | Kuti et al. |
| 2015/0116214 A1 | 4/2015 | Grunnet-Jepsen et al. |
| 2015/0131859 A1 | 5/2015 | Kim et al. |
| 2015/0172539 A1 | 6/2015 | Neglur |
| 2015/0193669 A1 | 7/2015 | Gu et al. |
| 2015/0205358 A1 | 7/2015 | Lyren |
| 2015/0205400 A1 | 7/2015 | Hwang et al. |
| 2015/0206321 A1 | 7/2015 | Scavezze et al. |
| 2015/0234569 A1 | 8/2015 | Hess |
| 2015/0258432 A1 | 9/2015 | Stafford et al. |
| 2015/0261291 A1 | 9/2015 | Mikhailov et al. |
| 2015/0304593 A1 | 10/2015 | Sakai |
| 2015/0323785 A1 | 11/2015 | Fukata et al. |
| 2016/0062573 A1 | 3/2016 | Dascola et al. |
| 2016/0086046 A1 | 3/2016 | Holz et al. |
| 2016/0093105 A1 | 3/2016 | Rimon et al. |

FOREIGN PATENT DOCUMENTS

| | | | | |
|---|---|---|---|---|
| CN | 201332447 Y | * | 10/2009 | |
| CN | 101729808 A | | 6/2010 | |
| CN | 101930610 A | | 12/2010 | |
| CN | 101951474 A | | 1/2011 | |
| CN | 102053702 A | | 5/2011 | |
| CN | 201859393 U | * | 6/2011 | |
| CN | 201859393 U | | 6/2011 | |
| CN | 102201121 A | | 9/2011 | |
| CN | 102236412 A | | 11/2011 | |
| DE | 4201934 A1 | | 7/1993 | |
| DE | 10326035 A1 | | 1/2005 | |
| DE | 102007015495 A1 | | 10/2007 | |
| DE | 102007015497 B4 | | 1/2014 | |
| EP | 0999542 A1 | | 5/2000 | |
| EP | 1477924 A2 | | 11/2004 | |
| EP | 1837665 A2 | | 9/2007 | |
| EP | 2369443 A2 | | 9/2011 | |
| GB | 2419433 A | | 4/2006 | |
| GB | 2480140 A | | 11/2011 | |
| GB | 2519418 A | | 4/2015 | |
| JP | H02236407 A | | 9/1990 | |
| JP | H08261721 A | | 10/1996 | |
| JP | H09259278 A | | 10/1997 | |
| JP | 2000023038 A | | 1/2000 | |
| JP | 2002-133400 A | | 5/2002 | |
| JP | 2003256814 A | | 9/2003 | |
| JP | 2004246252 A | | 9/2004 | |
| JP | 2006019526 A | | 1/2006 | |
| JP | 2011501316 A | * | 1/2006 | ........... G06V 40/107 |
| JP | 2006259829 A | | 9/2006 | |
| JP | 2007272596 A | | 10/2007 | |
| JP | 2008227569 A | | 9/2008 | |
| JP | 2009031939 A | | 2/2009 | |
| JP | 2009037594 A | | 2/2009 | |
| JP | 2010-060548 A | | 3/2010 | |
| JP | 2011010258 A | | 1/2011 | |
| JP | 2011065652 A | | 3/2011 | |
| JP | 2011-107681 A | | 6/2011 | |
| JP | 4906960 B2 | | 3/2012 | |
| JP | 4906960 B2 | * | 3/2012 | ........... G06F 3/0346 |
| JP | 2012-527145 A | | 11/2012 | |
| KR | 101092909 B1 | | 6/2011 | |
| RU | 2422878 C1 | | 6/2011 | |
| TW | 200844871 A | | 11/2008 | |
| WO | 1994026057 A1 | | 11/1994 | |
| WO | 2004114220 A1 | | 12/2004 | |
| WO | 2006020846 A2 | | 2/2006 | |
| WO | 2007137093 A2 | | 11/2007 | |
| WO | 201007662 A1 | | 1/2010 | |
| WO | 2010032268 A2 | | 3/2010 | |
| WO | 2010076622 A1 | | 7/2010 | |
| WO | 2010088035 A2 | | 8/2010 | |
| WO | 20100138741 A1 | | 12/2010 | |
| WO | 2011024193 A2 | | 3/2011 | |

(56) References Cited

FOREIGN PATENT DOCUMENTS

| WO | 2011036618 A2 | 3/2011 |
|---|---|---|
| WO | 2011044680 A1 | 4/2011 |
| WO | 2011045789 A1 | 4/2011 |
| WO | 2011119154 A1 | 9/2011 |
| WO | 2012027422 A2 | 3/2012 |
| WO | 2013109608 A2 | 7/2013 |
| WO | 2013109609 A2 | 7/2013 |
| WO | 2014208087 A1 | 12/2014 |
| WO | 2015026707 A1 | 2/2015 |

OTHER PUBLICATIONS

Delmarre et al., 3D Articulated Models and Multiview Tracking with Physical Forces, Mar. 2001 [retrieved Jun. 12, 2022], Computer Vision and Image Understanding, vol. 81, Issue 3, pp. 328-357. Retrieved: https://www.sciencedirect.com/science/article/pii/S1077314200908920 (Year: 2001).*
JP 2014-552391—Response to First Office Action dated Dec. 9, 2014 filed Jun. 8, 2016, 9 pages.
JP 2014-552391—Response to Second Office Action dated Jul. 7, 2015 filed Dec. 25, 2015, 4 pages.
JP 2014-552391—Third Office Action dated Jan. 26, 2016, 5 pages.
CN 2013800122765—Second Office Action dated Jul. 27, 2016, 6 pages.
U.S. Appl. No. 14/250,758—Office Action dated Sep. 8, 2016, 9 pages.
U.S. Appl. No. 14/710,499—Notice of Allowance dated Sep. 12, 2016, 28 pages.
U.S. Appl. No. 14/710,499—Office Action dated Apr. 14, 2016, 30 pages.
U.S. Appl. No. 14/710,499—Response to Office Action dated Apr. 14, 2016 filed Jul. 14, 2016, 37 pages.
De La Gorce et al., "Model-Based 3D Hand Pose Estimation from Monocular Video", Feb. 24, 2011 [retrieved Jul. 15, 2016], IEEE Transac Pattern Analysis and Machine Intell, vol. 33, Issue: 9, pp. 1793-1805, Retri Internet: <http://ieeexplore. ieee.org/xpl/logi n .jsp ?tp=&arnu mber=571 9617 &u rl=http%3A%2 F%2 Fieeexplore.ieee.org%2Fxpls%2 Fabs all.jsp%3Farnumber%3D5719617>.
Stenger, et al., "Model-Based 30 Tracking of an Articulated Hand", Computer Vision and Pattern Recognition, 2001. CVPR 2001 Proceedings of the 2001 IEEE Computer Society Conference on. vol. 2. IEEE, 2001, pp. 1-6.
U.S. Appl. No. 14/474,068—Notice of Allowance dated Jan. 25, 2017, 15 pages.
U.S. Appl. No. 14/712,699—Office Action dated Nov. 7, 2016, 17 pages.
U.S. Appl. No. 14/712,699—Response to Office Action dated Nov. 7, 2016 filed Mar. 7, 2017, 9 pages.
U.S. Appl. No. 14/712,699—Notice of Allowance dated Apr. 24, 2017, 8 pages.
U.S. Appl. No. 14/474,077—Response to Office Action dated Mar. 14, 2017 filed Jun. 9, 2017, 12 pages.
U.S. Appl. No. 14/474,068—Response to Office Action dated Sep. 12, 2016 filed Dec. 12, 2016, 9 pages.
U.S. Appl. No. 14/474,077—Office Action dated Sep. 8, 16 pages.
U.S. Appl. No. 14/474,077—Response to Office Action dated Jul. 26, 2016 filed Dec. 1, 2016, 10 pages.
U.S. Appl. No. 14/474,077—Office Action dated Sep. 8, 2017, 16 pages.
U.S. Appl. No. 14/474,077—Response to Office Action dated Sep. 8, 2017, filed Dec. 8, 2017, 11 pages.
U.S. Appl. No. 14/474,077—Office Action dated Jun. 27, 2018, 106 pages.
Yamamoto et al., "A Study for Vision Based Data Glove Considering Hidden Fingertip with Self-Occlusion", Aug. 8-10, 2012 [retrieved Mar. 16, 2018], 2012 13th ACIS Int. Conf on Soft Eng, AI, Network and Parallel & Dist Computing, pp. 315-320. Retrieved from the Internet: <<http://ieeexplore.ieee.org/abstract/document/6299298/>>.
Hong et al., "Variable structure multiple model for articulated human motion tracking from monocular video sequences", May 2012 [retrieved Mar. 3, 2018], Science China Information Science, vol. 55, Issue 5, pp. 1138-1150. Retrieved from the Interent: <https://link.springer.com/article/10.1007/s11432-011-4529-8>.
Calinon et al., A probabilistic approach based on dynamical systems to team and reproduce gestures by imitation, Dec. 19, 2011 [retrieved Mar. 16, 2018], pp. 1-12. Retrieved from the Internet: <https://web.archive.org/web/20111219151051 /http://infoscience.epfl.ch/record/147286/files/CalinonEtAIRAM2010.pdf?version=6>.
U.S. Appl. No. 14/474,077—Response to Office Action dated Jun. 27, 2018 filed Nov. 28, 2018, 18 pages.
U.S. Appl. No. 14/474,077—Office Action dated Jun. 26, 2019, 37 pages.
Hamer et al., "Data-Driven Animation of Hand-Object Interactions", Mar. 21-25, 2011, Face and Gesture 2011, pp. 360-367. [retrieved on Jun. 19, 2019], Retrieved from the internet <https://ieeexplore.ieee.org/abstract/document/5771426>.
Shimada et al., "Hand Gesture Estimation and Model Refinement using Monocular Camera-Ambiguity Limitation by Inequality v Constraints", Apr. 14-16, 1998, Procedings 3rd IEEE Inter Confer Auto Face and Gesture Recog,pp. 1-6. [retrieved on Jun. 19, 2019], Retrivied from the internet <https://ieeexplore.ieee.org/abstract/document/670960>.
U.S. Appl. No. 14/474,077—Response to Office Action dated Jun. 26, 2019 filed Sep. 26, 2019, 14 pages.
U.S. Appl. No. 16/538,593—Office Action dated Apr. 10, 2020, 16 pages.
U.S. Appl. No. 15/664,959—Notice of Allowance dated Nov. 17, 2017, 21 pages.
U.S. Appl. No. 15/942,296—Office Action dated Nov. 16, 2018, 34 pages.
U.S. Appl. No. 15/942,296—Notice of Allowance dated Mar. 27, 2019, 16 pages.
U.S. Appl. No. 15/989,090—Office Action dated Nov. 29, 2018, 13 pages.
U.S. Appl. No. 15/728,242—Notice of Allowance dated Jan. 31, 2018, 16 pages.
U.S. Appl. No. 14/474,077—Office Action dated Mar. 14, 2017, 13 pages.
U.S. Appl. No. 15/989,090—Response to Office Action dated Nov. 29, 2018, filed Feb. 28, 2019, 8 pages.
U.S. Appl. No. 15/989,090—Notice of Allowance dated May 21, 2019, 10 pages.
U.S. Appl. No. 14/474,068—Office Action dated Sep. 12, 2016, 23 pages.
U.S. Appl. No. 14/474,077—Office Action dated Jul. 26, 2016, 30 pages.
Ballan et al., "Lecture Notes Computer Science: 12th European Conference on Computer Vision: Motion Capture of Hands in Action Using Discriminative Salient Points", Oct. 7-13, 2012 [retrieved Jul. 14, 2016], Springer Berlin Heidelberg, vol. 7577, pp. 640-653. Retrieved from the Internet: <http://link.springer.com/chapter/1 0.1 007/978-3-642-33783-3 46>.
Cui et al., "Applications of Evolutionary Computing: Vision-Based Hand Motion Capture Using Genetic Algorithm", 2004 [retrieved Jul. 15, 2016], Springer Berlin Heidelberg, vol. 3005 of LNCS, pp. 289-300. Retrieved from the Internet: <http://link.springer.com/chapter/10.1007/978-3-540-24653-4_30>.
Delamarre et al., "Finding Pose of Hand in Video Images: A Stereo-based Approach", Apr. 14-16, 1998 [retrieved Jul. 15, 2016], Third IEEE Intern Conf on Auto Face and Gesture Recog, pp. 585-590. Retrieved from the Internet: <http://ieeexplore.ieee.org/xpl/login.jsp?tp=&arnumber=671011&url=http%3A%2F%2Fieeexplore.ieee.org%2Fxpls%2Fabs_all.jsp%3Farnumber%3D671011>.
Gorce et al., "Model-Based 3D Hand Pose Estimation from Monocular Video", Feb. 24, 2011 [retrieved Jul. 15, 2016], IEEE Transac Pattern Analysis and Machine Intell, vol. 33, Issue: 9, pp. 1793-1805, Retri Internet: <http://ieeexplore.ieee.org/xpl/logi n .jsp ?tp=&arnu mber=571 9617 &u rl=http%3A %2 F%2 Fieeexplore. ieee.org%2Fxpls%2 Fabs all. isp%3Farnumber%3D5719617>.

(56) References Cited

OTHER PUBLICATIONS

Guo et al., Featured Wand for 3D Interaction, Jul. 2-5, 2007 [retrieved Jul. 15, 2016], 2007 IEEE International Conference on Multimedia and Expo, pp. 2230-2233. Retrieved from the Internet: <http://ieeexplore.ieee.org/xpl/login.jsp?tp=&arnumber=4285129&tag=1&url=http%3A%2F%2Fieeexplore.ieee.org%2Fxpls%2Fabs_all.jsp%3Farnumber%3D4285129%26tag%3D1>.

Melax et al., "Dynamics Based 3D Skeletal Hand Tracking", May 29, 2013 [retrieved Jul. 14, 2016], Proceedings of Graphics Interface, 2013, pp. 63-70. Retrived from the Internet: <http://dl.acm.org/citation.cfm?id=2532141>.

Oka et al., "Real-Time Fingertip Tracking and Gesture Recognition", Nov./Dec. 2002 [retrieved Jul. 15, 2016], IEEE Computer Graphics and Applications, vol. 22, Issue: 6, pp. 64-71. Retrieved from the Internet: <http://ieeexplore.ieee.org/xpl/login.jsp?tp=&arnumber=1046630&url=http%3A%2F%2Fieeexplore.ieee.org%2Fxpls%2Fabsall.jsp%3Farnumber%3D1046630>.

Schlattmann et al., "Markerless 4 gestures 6 DOF real-time visual tracking of the human hand with automatic initialization", 2007 [retrieved Jul. 15, 2016], Eurographics 2007, vol. 26, No. 3, 10 pages, Retrieved from the Internet: <http://cg.cs.uni-bonn.de/aigaion2root/attachments/schlattmann-2007-markerless.pdf>.

Wang et al., "Tracking of Deformable Hand in Real Time as Continuous Input for Gesture-based Interaction", Jan. 28, 2007 [retrieved Jul. 15, 2016], Proceedings of the 12th International Conference on Intelligent User Interfaces, pp. 235-242. Retrieved fromthe Internet: <http://dl.acm.org/citation.cfm?id=1216338>.

Zhao et al., "Combining Marker-Based Mocap and RGB-D Camera for Acquiring High-Fidelity Hand Motion Data", Jul. 29, 2012 [retrieved Jul. 15, 2016], Proceedings of the ACM SIGGRAPH/Eurographics Symposium on Computer Animation, pp. 33-42, Retrieved from the Internet: <http://dl.acm.org/citation.cfm?id=2422363>.

PCT/US2013/021713—International Search Report and Written Opinion dated Sep. 11, 2013, 7 pages.
U.S. Appl. No. 13/742,845—Office Action dated Jul. 22, 2013, 19 pages.
U.S. Appl. No. 13/742,953—Office Action dated Jun. 14, 2013, 13 pages.
U.S. Appl. No. 13/742,953—Notice of Allowance dated Nov. 4, 2013, 14 pages.
PCT/US2013/021709—International Preliminary Report on Patentability dated Jul. 22, 2014, 22 pages.
U.S. Appl. No. 13/414,485—Office Action dated May 19, 2014, 16 pages.
U.S. Appl. No. 13/414,485—Final Office Action dated Feb. 12, 2015, 30 pages.
U.S. Appl. No. 14/106,148—Office Action dated Jul. 6, 2015, 12 pages.
PCT/US2013/069231—International Search Report and Written Opinion dated Mar. 13, 2014, 7 pages.
U.S. Appl. No. 13/744,810—Office Action dated Jun. 7, 2013, 15 pages.
U.S. Appl. No. 13/744,810—Final Office Action dated Dec. 16, 2013, 18 pages.
PCT/US2013/069231—International Preliminary Report with Written Opinion dated May 12, 2015, 8 pages.
U.S. Appl. No. 14/250,758—Office Action dated Jul. 6, 2015, 8 pages.
U.S. Appl. No. 13/414,485—Office Action dated Jul. 30, 2015, 22 pages.
U.S. Appl. No. 14/106,148—Notice of Allowance dated Dec. 2, 2015, 41 pages.
CN 2013800122765—Office Action dated Nov. 2, 2015, 17 pages.
U.S. Appl. No. 14/959,880—Notice of Allowance dated Mar. 2, 2016, 51 pages.
U.S. Appl. No. 14/250,758—Final Office Action dated Mar. 10, 2016, 10 pages.
U.S. Appl. No. 13/414,485—Office Action dated Apr. 21, 2016, 24 pages.
U.S. Appl. No. 14/710,512—Notice of Allowance dated Apr. 28, 2016, 25 pages.
U.S. Appl. No. 14/959,891—Office Action dated Apr. 11, 2016, 47 pages.
U.S. Appl. No. 14/250,758—Response to Final Office Action dated Mar. 10, 2016 filed May 5, 2016, 12 pages.
U.S. Appl. No. 14/106,148—Response to Office Action dated Jul. 6, 2015 filed Nov. 6, 2015, 41 pages.
U.S. Appl. No. 14/959,880—Notice of Allowance dated Jul. 12, 2016, 22 pages.
U.S. Appl. No. 14/106,148—Notice of Allowance dated Jul. 20, 2016, 30 pages.
U.S. Appl. No. 14/959,891—Notice of Allowance dated Jul. 28, 2016, 19 pages.
JP 2014-552391—First Office Action dated Dec. 9, 2014, 6 pages.
U.S. Appl. No. 13/742,845—Response to Office Action dated Jul. 22, 2013 filed Sep. 26, 2013, 7 pages.
U.S. Appl. No. 14/959,891—Response to Office Action dated Apr. 11, 2016 filed Jun. 8, 2016, 25 pages.
DE 11 2013 000 590.5—First Office Action dated Nov. 5, 2014, 7 pages.
DE 11 2013 000 590.5—Response to First Office Action dated Nov. 5, 2014 filed Apr. 24, 2015, 1 page.
DE 11 2013 000 590.5—Second Office Action dated Apr. 29, 2015, 7 pages.
DE 11 2013 000 590.5—Response to Second Office Action dated Apr. 29, 2015 filed Sep. 16, 2015, 11 pages.
DE 11 2013 000 590.5—Third Office Action dated Sep. 28, 2015, 4 pages.
DE 11 2013 000 590.5—Response to Third Office Action dated Sep. 28, 2015 filed Dec. 14, 2015, 64 pages.
DE 11 2013 000 590.5—Notice of Allowance dated Jan. 18, 2016, 8 pages.
CN 2013800122765—Response to First Office Action dated Nov. 2, 2015 filed May 14, 2016, 14 pages.
Gorce et al., "Model-Based 3D Hand Pose Estimation from Monocular Video", Feb. 24, 2011 [retrieved Jul. 15, 2016], IEEE Transac Pattern Analysis and Machine Intell, vol. 33, Issue: 9, pp. 1793-1805, Retri Internet: <http://ieeexplore.ieee.org/xpl/logi n .jsp ?tp=&arnu mber=571 9617&u rl=http%3A %2 F%2 Fieeexplore.ieee.org%2Fxpls%2 Fabsall.jsp%3Farnumber%3D5719617>.
Oka et al., "Real-Time Fingertip Tracking and Gesture Recognition", Nov./Dec. 2002 [retrieved Jul. 15, 2016], IEEE Computer Graphics and Applications, vol. 22, Issue: 6, pp. 64-71. Retrieved from the Internet: <http://ieeexplore.ieee.org/xpl/login.jsp?tp=&arnumber=1046630&url=http%3A%2F%2Fieeexplore.ieee.org%2Fxpls%2Fabsall.jsp%3Farnumber%3D1046630>.
PCT/US2013/021709—International Search Report and Written Opinion dated Sep. 12, 2013, 22 pages.
PCT/US2013/021709—International Preliminary Report on Patentability dated Jul. 22, 2014, 22 pages (WO 2013/109608).
Yamamoto et al., "A Study for Vision Based Data Glove Considering Hidden Fingertip with Self-Occlusion", Aug. 8-10, 2012 [retrieved Mar. 16, 2018], 2012 13th ACIS Int. Conf on Soft Eng, AI, Network and Parallel & Dist Computing, pp. 315-320. Retrieved from the Internet: <<http://ieeexplore.ieee.org/abstract/document/6299298/>>.
Calinon et al., A probabilistic approach based on dynamical systems to learn and reproduce gestures by imitation, Dec. 19, 2011 [retrieved Mar. 16, 2018], pp. 1-12. Retrieved from the Internet: <https://web.archive.org/web/20111219151051/http://infoscience.epfl.ch/record/147286/files/CalinonEtAIRAM2010.pdf?version=6>.
U.S. Appl. No. 14/474,077, filed Aug. 29, 2014, Pending.
JP 2014-552391—Second Office Action dated Jul. 7, 2015, 7 pages.

\* cited by examiner

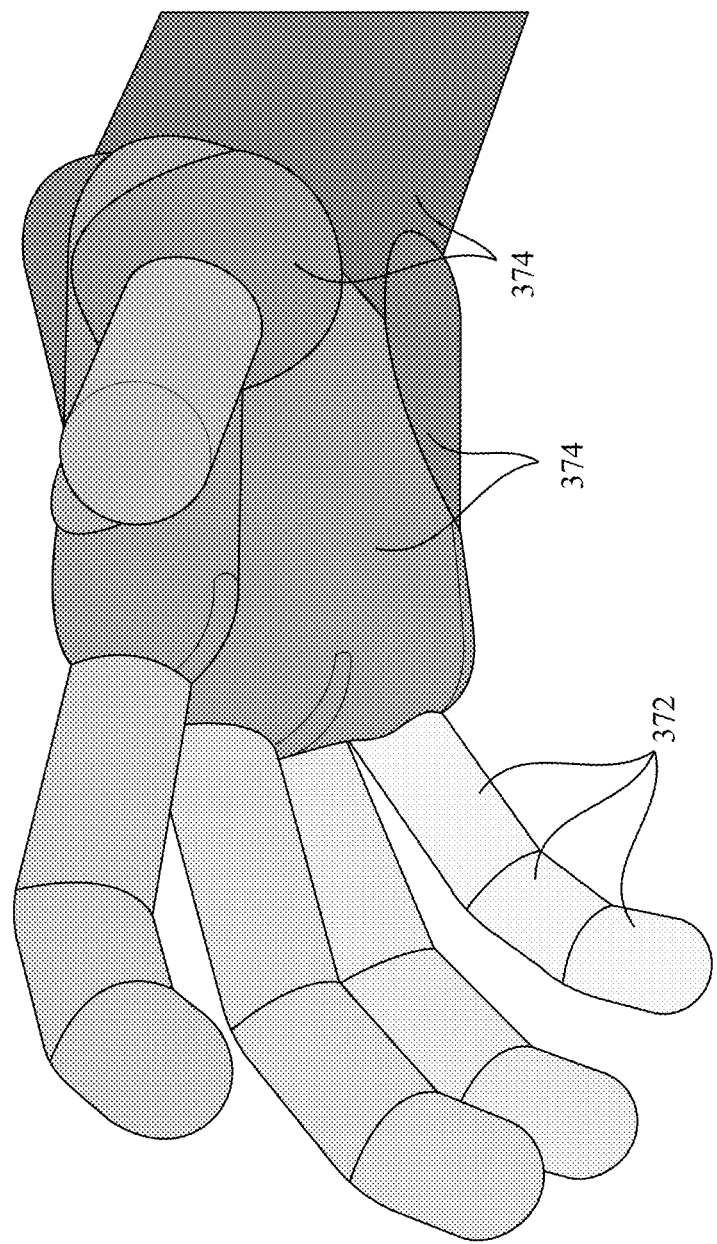

902 — determining observation information characterizing a surface of a control object from at least one image of a gestural motion of the control object in a three-dimensional (3D) sensory space 912 — constructing a 3D solid model to represent the control object by fitting one or more 3D solid subcomponents to the characterized surface 922 — improving the 3D solid model's representation of the gestural motion 932 — calculating an error indication between a point on the characterized surface of the control object and a corresponding point on at least one of the 3D solid subcomponents 942 — responsive to the error indication adjusting the 3D solid model

*FIG. 9*

```
                                                    1000
┌──────┐  ┌────────────────────────────────────────────────────┐
│ 1002 │──│ determining observation information characterizing gestural motion of a │
│      │  │ control object in a three-dimensional (3D) sensory space from at least one │
│      │  │ image captured at time t0 │
└──────┘  └────────────────────────────────────────────────────┘
                              │
                              ▼
┌──────┐  ┌────────────────────────────────────────────────────┐
│ 1012 │──│ constructing a 3D solid model to represent the control object by fitting one │
│      │  │ or more 3D solid subcomponents to a construct of the control object defined │
│      │  │ by the observation information based on the image captured at time t0 │
└──────┘  └────────────────────────────────────────────────────┘
                              │
                              ▼
┌──────┐  ┌────────────────────────────────────────────────────┐
│ 1022 │──│ improving conformance of the 3D solid model to the modified observation │
│      │  │ information │
└──────┘  └────────────────────────────────────────────────────┘
                              │
                              ▼
┌──────┐  ┌────────────────────────────────────────────────────┐
│ 1032 │──│ calculating an error indication between a point on another construct defined │
│      │  │ based on the image captured at time t1 and a corresponding point on at least │
│      │  │ one of the 3D solid subcomponents fitted based on the image captured at │
│      │  │ time t0 │
└──────┘  └────────────────────────────────────────────────────┘
                              │
                              ▼
┌──────┐  ┌────────────────────────────────────────────────────┐
│ 1042 │──│ responsive to the error indication adjusting the 3D solid model │
└──────┘  └────────────────────────────────────────────────────┘
```

*FIG. 10*

DETERMINING SPANS AND SPAN LENGTHS OF A CONTROL OBJECT IN A FREE SPACE GESTURE CONTROL ENVIRONMENT

PRIORITY AND RELATED APPLICATION STATEMENTS

This application is a continuation of U.S. Non-Provisional patent application Ser. No. 14/474,077 filed Aug. 29, 2014, entitled "PREDICTIVE INFORMATION FOR FREE SPACE GESTURE CONTROL AND COMMUNICATION" (ULTI 1007-2), which claims priority to U.S. Provisional Patent Application No. 61/871,790 filed Aug. 29, 2013 entitled "PREDICTIVE INFORMATION FOR FREE SPACE GESTURE CONTROL AND COMMUNICATION" (LEAP 1086-1/LPM-001CP2), to U.S. Provisional Patent Application No. 61/873,758 filed Sep. 4, 2013 entitled "PREDICTIVE INFORMATION FOR FREE SPACE GESTURE CONTROL AND COMMUNICATION" (LEAP 1007-1/LPM-1007APR), and to U.S. Provisional Patent Application No. 61/898,462 filed Oct. 31, 2013 entitled "PREDICTIVE INFORMATION FOR FREE SPACE GESTURE CONTROL AND COMMUNICATION" (ULTI 1018-1). The non-provisional and provisional applications are hereby incorporated by reference for all purposes.

This application is related to US Patent Application entitled "PREDICTIVE INFORMATION FOR FREE SPACE GESTURE CONTROL AND COMMUNICATION," filed contemporaneously. The related application is hereby incorporated by reference for all purposes.

This application is related to U.S. patent application Ser. No. 14/280,018 filed May 16, 2014, entitled "SYSTEMS AND METHODS FOR MACHINE CONTROL" (LPM-0001CP3/7312204003), which is a continuation-in-part of U.S. patent application Ser. No. 14/106,140 filed Dec. 13, 2013, entitled "SYSTEMS AND METHODS FOR CAPTURING MOTION IN THREE-DIMENSIONAL SPACE" (LPM-001CP2C1/7312203003), which is a continuation of U.S. patent application Ser. No. 13/742,953 filed Jan. 16, 2013 (now U.S. Pat. No. 8,638,989 issued Jan. 28, 2014), entitled "SYSTEMS AND METHODS FOR CAPTURING MOTION IN THREE-DIMENSIONAL SPACE" (LPM-001CP2/7312204002), which is a continuation-in-part of U.S. patent application Ser. No. 13/414,485 filed Mar. 7, 2012, entitle "MOTION CAPTURE USING CROSS-SECTIONS OF AN OBJECT" (LPM-001/7312202001), and Ser. No. 13/724,357 filed Dec. 21, 2012, entitled "SYSTEMS AND METHODS FOR CAPTURING MOTION IN THREE-DIMENSIONAL SPACE" (LEAP 1006-3/LPM-001CP), and also claims priority to and the benefit of U.S. Provisional Patent Application Nos. 61/724,091 filed Nov. 8, 2012, entitled "SYSTEMS AND METHODS FOR CAPTURING MOTION IN THREE-DIMENSIONAL SPACE" (LPM-001PR2/7312201010), and 61/587,554 filed Jan. 17, 2012, entitled "METHODS AND SYSTEMS FOR IDENTIFYING POSITION AND SHAPE OF OBJECTS IN THREE-DIMENSIONAL SPACE" (PA5663PRV). The present invention is further related to U.S. patent application Ser. No. 14/250,758 filed Apr. 11, 2014, entitled "SYSTEMS AND METHODS FOR TRACKING OCCLUDED OBJECTS IN THREE-DIMENSIONAL SPACE" (LPM-001A/7313842001), which claims priority to U.S. Provisional Patent Application No. 61/811,415 filed Apr. 12, 2013, entitled "SYSTEMS AND METHODS FOR CAPTURE MOTION IN THREE-DIMENSIONAL SPACE" (LPM-001PR3). The related applications are hereby incorporated by reference for all purposes.

FIELD OF THE TECHNOLOGY DISCLOSED

The technology disclosed relates, in general, to image analysis, and in particular implementations to identifying shapes and capturing motions of objects in three-dimensional (3D) space.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves may also correspond to implementations of the claimed technology.

Motion capture has numerous applications. For example, in filmmaking, digital models generated using motion capture can be used as the basis for the motion of computer-generated characters or objects. In sports, motion capture can be used by coaches to study an athlete's movements and guide the athlete toward improved body mechanics. In video games or virtual reality applications, motion capture can be used to allow a person to interact with a virtual environment in a natural way, e.g., by waving to a character, pointing at an object, or performing an action such as swinging a golf club or baseball bat.

The term "motion capture" refers generally to processes that capture movement of a subject in three-dimensional (3D) space and translate that movement into, for example, a digital model or other representation. Motion capture is typically used with complex subjects that have multiple separately articulating members whose spatial relationships change as the subject moves. For instance, if the subject is a walking person, not only does the whole body move across space, but the position of arms and legs relative to the person's core or trunk are constantly shifting. Motion capture systems are typically interested in modeling this articulation.

Most existing motion capture systems rely on markers or sensors worn by the subject while executing the motion and/or on the strategic placement of numerous cameras in the environment to capture images of the moving subject from different angles. Such systems tend to be expensive to construct. In addition, markers or sensors worn by the subject can be cumbersome and interfere with the subject's natural movement. Further, systems involving large numbers of cameras tend not to operate in real time, due to the volume of data that needs to be analyzed and correlated. Such considerations of cost, complexity and convenience have limited the deployment and use of motion capture technology.

Consequently, there is a need for improved techniques for capturing the motion of objects in real time without attaching sensors or markers thereto.

SUMMARY

Among other aspects, implementations can provide for improved image based machine interface and/or communication by interpreting a control object's position and/or motion (including objects having one or more articulating members, i.e., humans and/or animals and/or machines). Among other aspects, implementations can enable automatically (e.g., programmatically) creating, improving and/or exploiting a model using differences between observation information and predicted information comprising radial solids and/or other shapes, enable conformance of the model to real world changes in the control object facilitating real time or near real time control, communication and/or interaction with machines. Inputs can be interpreted from one or a sequence of images in conjunction with receiving input, commands, communications and/or other user-machine interfacing, gathering information about objects, events and/or actions existing or occurring within an area being explored, monitored, or controlled, and/or combinations thereof.

According to one aspect, a method implementation for improving a prediction of an object in space includes determining prediction information for the object. The method further includes receiving observation information for the object. Also, the method can include determining a closest distance between at least one point of the prediction information and at least one point of the observation information. Improved prediction information can be determined based at least in part upon the closest distance.

In an implementation, determining prediction information for the object includes determining at least a portion of a model (model subcomponent) of the object including at least one radial solid.

In an implementation, receiving observation information for the object includes receiving an image from at least one image capture device.

In an implementation, determining a closest distance between at least one point of the prediction information and at least one point of the observation information includes determining a closest distance between a first point belonging to a set of points defining a virtual surface determined from the observation information and a second point belonging to a model subcomponent determined to be corresponding to the first point.

In an implementation, determining improved prediction information based at least in part upon the closest distance includes determining an error indication based at least in part upon the closest distance; and applying the error indication to the prediction information to provide improved prediction information.

In another aspect, a method for predicting an object is provided. The method can include receiving observation information including information about an object surface portion from an imaging system. Determining from the observation information prediction information including a virtual surface portion corresponding to the object surface portion is also part of the method. The method further includes determining at least a portion of a model (model subcomponent) of the object. In an implementation, this can include determining at least one radial solid, which can be selected from a set of radial solids to approximate at least part of the object surface portion; determining a first point belonging to a set of points defining the virtual surface portion determined from the observation information; determining a second point belonging to the model subcomponent corresponding to the first point; and determining a closest distance between the first point and the second point. The method can also include improving prediction information based at least in part upon the closest distance by determining an error indication based at least in part upon the closest distance and applying the error indication to the predication information to provide improved prediction information.

In a further aspect, systems can be provided. One system implementation includes an image capture system including at least one camera oriented toward a field of view facilitating imaging an object. An image analyzer is coupled to the camera. The image analyzer can be configured to determine prediction information for the object. The image analyzer can receive observation information for the object. The image analyzer can determine a closest distance between at least one point of the prediction information and at least one point of the observation information. Further, the image analyzer can determine improved prediction information based at least in part upon the closest distance.

In another aspect, a computer-implemented method for facilitating control of a user interface via free-space motions of a control object is provided. One method implementation includes receiving data indicative of tracked motions of the control object, and computationally (i.e., using a processor) defining an engagement target and updating a spatial position (and, in some implementations, also a spatial orientation) of the engagement target based at least in part on the data such that the position of the engagement target follows the tracked motions of the control object. Further, implementations of the method involve computationally determining whether the control object intersects the engagement target, and, if so, controlling the user interface in a first mode (e.g., an engaged mode), and otherwise controlling the user interface in a second mode different from the first mode (e.g., a disengaged mode).

Techniques for determining positional, shape and/or motion information about an object are described in further detail in co-pending U.S. Ser. No. 13/414,485, filed Mar. 7, 2012, and Ser. No. 13/742,953, filed Jan. 16, 2013, the entire disclosures of which are hereby incorporated by reference as if reproduced verbatim beginning here.

Advantageously, some implementations can provide for improved interface with computing and/or other machinery than would be possible with heretofore known techniques. In some implementations, a richer human—machine interface experience can be provided. The following detailed description together with the accompanying drawings will provide a better understanding of the nature and advantages provided for by implementations.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIGS. 3B and 3C illustrate different views of a 3D capsule hand according to one implementation of the technology disclosed.

FIG. 6B shows one implementation of gestural data of one or more free-form gestures performed using a hand.

FIG. 9 illustrates an example method of capturing gestural motion of a control object in a 3D sensory space.

FIG. 10 is a representative method of accurately capturing gestural motion of a control object in a 3D sensory space.

DETAILED DESCRIPTION

Gesture Recognition System

Figure 1:
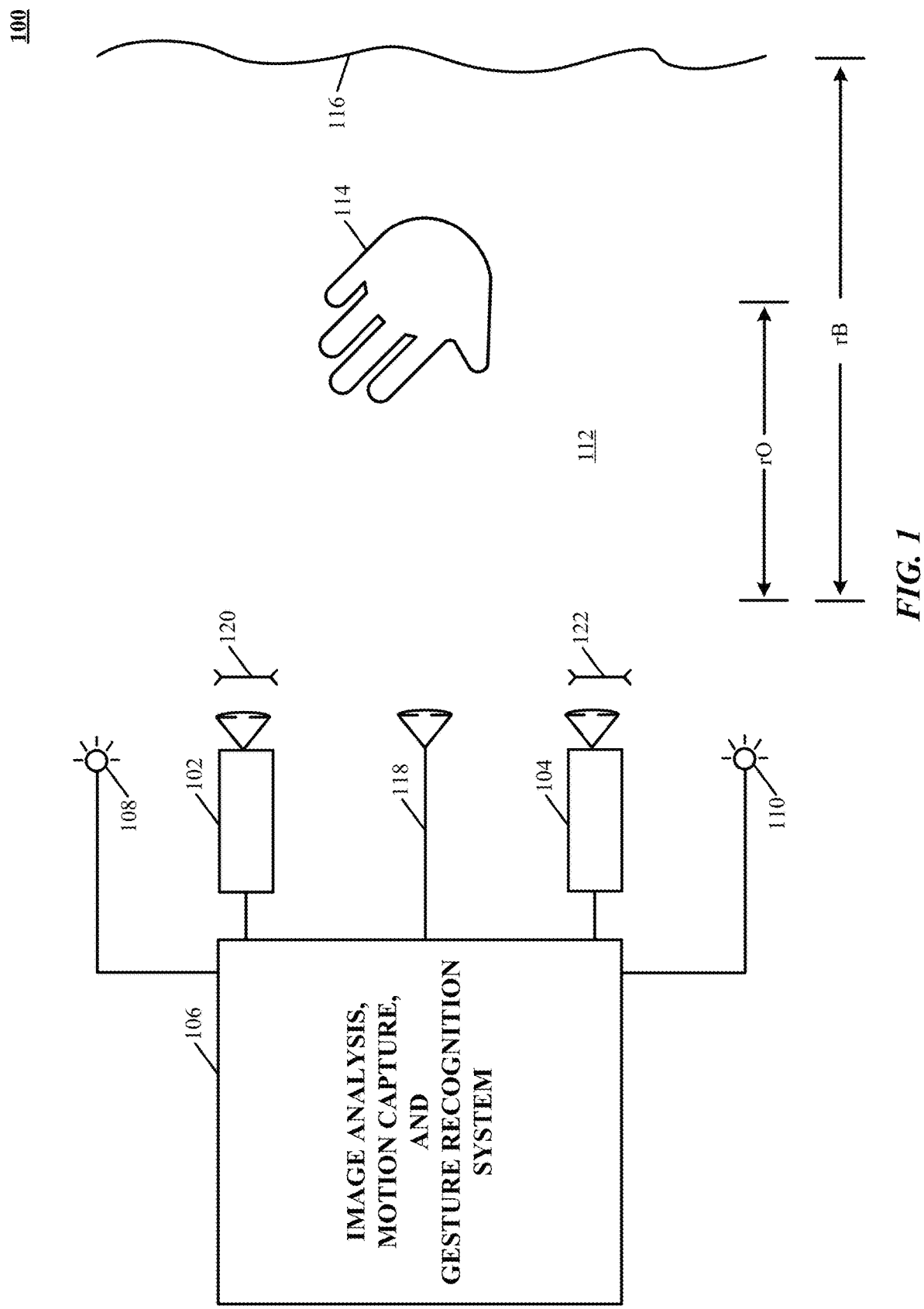
FIG. 1 illustrates an example gesture-recognition system.

Implementations of the technology disclosed relate to methods and systems for capturing motion and/or determining position of an object using small amounts of information. For example, an outline of an object's shape, or silhouette, as seen from a particular vantage point can be used to define bounding line segments to the object from that vantage point in various planes, referred to as "observation information" according to one implementation. Positions of the control object determined for different slices can be correlated to construct a 3D solid model of the object by fitting a plurality of 3D solid subcomponents to the observation information, including its position and shape. A succession of images can be analyzed using the same technique to model motion of the object. Motion of a complex object that has multiple separately articulating members (e.g., a human hand) can be modeled using techniques described herein.

The technology disclosed can be applied to solve the technical problem of reducing computational time and complexity of detecting and interpreting motions and gestures of control objects in a 3D sensory space. In one implementation, a 3D solid model is constructed based on the observation information of the control object. Further, the constructed 3D solid model is improved by a variety of techniques. In one implementation, the 3D solid model is compared with the observation information to detect an error terms or indications, which can be overcome to generate a more accurate model. In another implementation, the 3D solid model is improved by correcting the model itself and removing any impurities or spurious or discontinuous 3D model subcomponents, which may not comply with real-world physical characteristics of the control object being tracked.

In another implementation, the 3D solid model is constrained by replacing a plurality of 3D solid subcomponents of the 3D solid model with fewer representative subcomponents. In one implementation, the representative subcomponents are extreme subcomponents of the 3D solid model. For instance, for a hand, the 3D solid model can include at least three subcomponents respectively representing the proximal carpal, intermediary knuckle, and the dorsal carpal. However, the movements and interactions of the hands can be tracked by only tracking the dorsal carpal. As a result, the 3D solid model is constrained to include only the extreme subcomponent representing the dorsal carpal. This constraint 3D solid model greatly reduces the computational time and resources and thus cane be applied for motion tracking in mobile devices, according to one implementation. In yet another implementation, a plurality of 3D solid subcomponents is represented by an artificial construct rather than individual subcomponents to achieve a low-power consumption state of a device. In such an implementation, the artificial constructs are simple geometric shapes such as line segments, rectangles, circles, ellipses, etc., thus improving the efficiency and response time of the motion tracking and gesture recognition algorithm.

Implementations described herein with reference to examples can provide for automatically (e.g., programmatically) determining a correct way to interpret inputs detected from positional information (e.g., position, volume, shape, and/or surface characteristics) and/or motion information (e.g., translation, rotation, and/or other structural change) of a portion of a hand or other detectable object based upon a zone determined from the hand's (or other object's) position. Inputs can be interpreted from one or a sequence of images in conjunction with receiving input, commands, communications and/or other user-machine interfacing, gathering information about objects, events and/or actions existing or occurring within an area being explored, monitored, or controlled, and/or combinations thereof.

As shown in FIG. 1, which illustrates an exemplary motion-capture system 100 including any number of cameras 102, 104 coupled to an image analysis, motion capture, and control system 106 (The system 106 is hereinafter variably referred to as the "image analysis and motion capture system," the "image analysis system," the "motion capture system," "the gesture recognition system," the "control and image-processing system," the "control system," or the "image-processing system," depending on which functionality of the system is being discussed).

Cameras 102, 104 provide digital image data to the image analysis, motion capture, and control system 106, which analyzes the image data to determine the three-dimensional (3D) position, orientation, and/or motion of the object 114 the field of view of the cameras 102, 104. Cameras 102, 104 can be any type of cameras, including cameras sensitive across the visible spectrum or, more typically, with enhanced sensitivity to a confined wavelength band (e.g., the infrared (IR) or ultraviolet bands); more generally, the term "camera" herein refers to any device (or combination of devices) capable of capturing an image of an object and representing that image in the form of digital data. While illustrated using an example of a two camera implementation, other implementations are readily achievable using different numbers of cameras or non-camera light sensitive image sensors or combinations thereof. For example, line sensors or line cameras rather than conventional devices that capture a two-dimensional (2D) image can be employed. Further, the term "light" is used generally to connote any electromagnetic radiation, which may or may not be within the visible spectrum, and can be broadband (e.g., white light) or narrowband (e.g., a single wavelength or narrow band of wavelengths).

Cameras 102, 104 are preferably capable of capturing video images (i.e., successive image frames at a constant rate of at least 15 frames per second); although no particular frame rate is required. The capabilities of cameras 102, 104 are not critical to the technology disclosed, and the cameras can vary as to frame rate, image resolution (e.g., pixels per image), color or intensity resolution (e.g., number of bits of intensity data per pixel), focal length of lenses, depth of field, etc. In general, for a particular application, any cameras capable of focusing on objects within a spatial volume of interest can be used. For instance, to capture motion of the hand of an otherwise stationary person, the volume of interest can be defined as a cube approximately one meter on a side. To capture motion of a running person, the volume of interest might have dimensions of tens of meters in order to observe several strides.

Cameras 102, 104 can be oriented in any convenient manner. In one implementation, the optical axes of the cameras 102, 104 are parallel, but this is not required. As described below, each of the 102, 104 can be used to define a "vantage point" from which the object 114 is seen; if the location and view direction associated with each vantage point are known, the locus of points in space that project onto a particular position in the cameras' image plane can be determined. In some implementations, motion capture is reliable only for objects in an area where the fields of view of cameras 102, 104; the cameras 102, 104 can be arranged to provide overlapping fields of view throughout the area where motion of interest is expected to occur.

In some implementations, the illustrated system 100 includes one or more sources 108, 110, which can be disposed to either side of cameras 102, 104, and are controlled by image analysis and motion capture system 106. In one implementation, the sources 108, 110 are light sources. For example, the light sources can be infrared light sources, e.g., infrared light emitting diodes (LEDs), and cameras 102, 104 can be sensitive to infrared light. Use of infrared light can allow the motion-capture system 100 to operate under a broad range of lighting conditions and can avoid various inconveniences or distractions that can be associated with directing visible light into the region where the person is moving. However, a particular wavelength or region of the electromagnetic spectrum can be required. In one implementation, filters 120, 122 are placed in front of cameras 102, 104 to filter out visible light so that only infrared light is registered in the images captured by cameras 102, 104. Alternatively, cameras 102, 104 include elements sensitive to different spectral portions, e.g., visible light (RGB) and infrared (IR) radiation, and information from the different spectral portions can be processed independently, or in conjunction with one another. In another implementation, the sources 108, 110 are sonic sources providing sonic energy appropriate to one or more sonic sensors (not shown in FIG. 1 for clarity sake) used in conjunction with, or instead of, cameras 102, 104. The sonic sources transmit sound waves to the user; with the user either blocking ("sonic shadowing") or altering the sound waves ("sonic deflections") that impinge upon her. Such sonic shadows and/or deflections can also be used to detect the user's gestures and/or provide presence information and/or distance information using ranging techniques. In some implementations, the sound waves are, for example, ultrasound, which are not audible to humans.

It should be stressed that the arrangement shown in FIG. 1 is representative and not limiting. For example, lasers or other light sources can be used instead of LEDs. In implementations that include laser(s), additional optics (e.g., a lens or diffuser) can be employed to widen the laser beam (and make its field of view similar to that of the cameras). Useful arrangements can also include short-angle and wide-angle illuminators for different ranges. Light sources are typically diffuse rather than specular point sources; for example, packaged LEDs with light-spreading encapsulation are suitable.

In operation, light sources 108, 110 are arranged to illuminate a region of interest 112 that includes an entire control object or its portion 114 (in this example, a hand) that can optionally hold a tool or other object of interest. Cameras 102, 104 are oriented toward the region 112 to capture video images of the hand 114. In some implementations, the operation of light sources 108, 110 and cameras 102, 104 is controlled by the image analysis and motion capture system 106, which can be, e.g., a computer system, control logic implemented in hardware and/or software or combinations thereof. Based on the captured images, image analysis and motion capture system 106 determines the position and/or motion of hand 114.

Motion capture can be improved by enhancing contrast between the object of interest 114 and background surfaces like surface 116 visible in an image, for example, by means of controlled lighting directed at the object. For instance, in motion capture system 106 where an object of interest 114, such as a person's hand, is significantly closer to the cameras 102 and 104 than the background surface 116, the falloff of light intensity with distance ($1/r^2$ for point like light sources) can be exploited by positioning a light source (or multiple light sources) near the camera(s) or other image-capture device(s) and shining that light onto the object 114. Source light reflected by the nearby object of interest 114 can be expected to be much brighter than light reflected from more distant background surface 116, and the more distant the background (relative to the object), the more pronounced the effect will be. Accordingly, a threshold cut off on pixel brightness in the captured images can be used to distinguish "object" pixels from "background" pixels. While broadband ambient light sources can be employed, various implementations use light having a confined wavelength range and a camera matched to detect such light; for example, an infrared source light can be used with one or more cameras sensitive to infrared frequencies.

In operation, cameras 102, 104 are oriented toward a region of interest 112 in which an object of interest 114 (in this example, a hand) and one or more background objects 116 can be present. Light sources 108, 110 are arranged to illuminate region 112. In some implementations, one or more of the light sources 108, 110 and one or more of the cameras 102, 104 are disposed below the motion to be detected, e.g., in the case of hand motion, on a table or other surface beneath the spatial region where hand motion occurs. This is an optimal location because the amount of information recorded about the hand is proportional to the number of pixels it occupies in the camera images, and the hand will occupy more pixels when the camera's angle with respect to the hand's "pointing direction" is as close to perpendicular as possible. Further, if the cameras 102, 104 are looking up, there is little likelihood of confusion with background objects (clutter on the user's desk, for example) and other people within the cameras' field of view.

Control and image-processing system 106, which can be, e.g., a computer system, can control the operation of light sources 108, 110 and cameras 102, 104 to capture images of region 112. Based on the captured images, the image-processing system 106 determines the position and/or motion of object 114. For example, as a step in determining the position of object 114, image-analysis system 106 can determine which pixels of various images captured by cameras 102, 104 contain portions of object 114. In some implementations, any pixel in an image can be classified as an "object" pixel or a "background" pixel depending on whether that pixel contains a portion of object 114 or not. With the use of light sources 108, 110, classification of pixels as object or background pixels can be based on the brightness of the pixel. For example, the distance ($r_O$) between an object of interest 114 and cameras 102, 104 is expected to be smaller than the distance ($r_B$) between background object(s) 116 and cameras 102, 104. Because the intensity of light from sources 108, 110 decreases as $1/r^2$, object 114 will be more brightly lit than background 116, and pixels containing portions of object 114 (i.e., object pixels) will be correspondingly brighter than pixels containing portions of background 116 (i.e., background pixels). For example, if $r_B/r_O=2$, then object pixels will be approximately four times brighter than background pixels, assuming object 114 and background 116 are similarly reflective of the light from sources 108, 110, and further assuming that the overall illumination of region 112 (at least within the frequency band captured by cameras 102, 104) is dominated by light sources 108, 110. These conditions generally hold for suitable choices of cameras 102, 104, light sources 108, 110, filters 120, 122, and objects commonly encountered. For example, light sources 108, 110 can be infrared LEDs capable of strongly emitting radiation in a narrow frequency band, and filters 120, 122 can be matched to the frequency band of light sources 108, 110. Thus, although a human hand or body, or a heat source or other object in the background, can emit some infrared radiation, the response of cameras 102, 104 can still be dominated by light originating from sources 108, 110 and reflected by object 114 and/or background 116.

In this arrangement, image-analysis system 106 can quickly and accurately distinguish object pixels from background pixels by applying a brightness threshold to each pixel. For example, pixel brightness in a CMOS sensor or similar device can be measured on a scale from 0.0 (dark) to 1.0 (fully saturated), with some number of gradations in between depending on the sensor design. The brightness encoded by the camera pixels scales standardly (linearly) with the luminance of the object, typically due to the deposited charge or diode voltages. In some implementations, light sources 108, 110 are bright enough that reflected light from an object at distance $r_O$ produces a brightness level of 1.0 while an object at distance $r_B=2r_O$ produces a brightness level of 0.25. Object pixels can thus be readily distinguished from background pixels based on brightness. Further, edges of the object can also be readily detected based on differences in brightness between adjacent pixels, allowing the position of the object within each image to be determined. Correlating object positions between images from cameras 102, 104 allows image-analysis system 106 to determine the location in 3D space of object 114, and analyzing sequences of images allows image-analysis system 106 to reconstruct 3D motion of object 114 using motion algorithms.

In accordance with various implementations of the technology disclosed, the cameras 102, 104 (and typically also the associated image-analysis functionality of control and image-processing system 106) are operated in a low-power mode until an object of interest 114 is detected in the region of interest 112. For purposes of detecting the entrance of an object of interest 114 into this region, the system 100 further includes one or more light sensors 118 (e.g., a CCD or CMOS sensor) and/or an associated imaging optic (e.g., a lens) that monitor the brightness in the region of interest 112 and detect any change in brightness. For example, a single light sensor including, e.g., a photodiode that provides an output voltage indicative of (and over a large range proportional to) a measured light intensity can be disposed between the two cameras 102, 104 and oriented toward the region of interest 112. The one or more sensors 118 continuously measure one or more environmental illumination parameters such as the brightness of light received from the environment. Under static conditions—which implies the absence of any motion in the region of interest 112—the brightness will be constant. If an object enters the region of interest 112, however, the brightness can abruptly change. For example, a person walking in front of the sensor(s) 118 can block light coming from an opposing end of the room, resulting in a sudden decrease in brightness. In other situations, the person can reflect light from a light source in the room onto the sensor, resulting in a sudden increase in measured brightness.

The aperture of the sensor(s) 118 can be sized such that its (or their collective) field of view overlaps with that of the cameras 102, 104. In some implementations, the field of view of the sensor(s) 118 is substantially co-existent with that of the cameras 102, 104 such that substantially all objects entering the camera field of view are detected. In other implementations, the sensor field of view encompasses and exceeds that of the cameras. This enables the sensor(s) 118 to provide an early warning if an object of interest approaches the camera field of view. In yet other implementations, the sensor(s) capture(s) light from only a portion of the camera field of view, such as a smaller area of interest located in the center of the camera field of view.

The control and image-processing system 106 monitors the output of the sensor(s) 118, and if the measured brightness changes by a set amount (e.g., by 10% or a certain number of candela), it recognizes the presence of an object of interest in the region of interest 112. The threshold change can be set based on the geometric configuration of the region of interest and the motion-capture system, the general lighting conditions in the area, the sensor noise level, and the expected size, proximity, and reflectivity of the object of interest so as to minimize both false positives and false negatives. In some implementations, suitable settings are determined empirically, e.g., by having a person repeatedly walk into and out of the region of interest 112 and tracking the sensor output to establish a minimum change in brightness associated with the person's entrance into and exit from the region of interest 112. Of course, theoretical and empirical threshold-setting methods can also be used in conjunction. For example, a range of thresholds can be determined based on theoretical considerations (e.g., by physical modelling, which can include ray tracing, noise estimation, etc.), and the threshold thereafter fine-tuned within that range based on experimental observations.

In implementations where the area of interest 112 is illuminated, the sensor(s) 118 will generally, in the absence of an object in this area, only measure scattered light amounting to a small fraction of the illumination light. Once an object enters the illuminated area, however, this object can reflect substantial portions of the light toward the sensor(s) 118, causing an increase in the measured brightness. In some implementations, the sensor(s) 118 is (or are) used in conjunction with the light sources 108, 110 to deliberately measure changes in one or more environmental illumination parameters such as the reflectivity of the environment within the wavelength range of the light sources. The light sources can blink, and a brightness differential be measured between dark and light periods of the blinking cycle. If no object is present in the illuminated region, this yields a baseline reflectivity of the environment. Once an object is in the area of interest 112, the brightness differential will increase substantially, indicating increased reflectivity. (Typically, the signal measured during dark periods of the blinking cycle, if any, will be largely unaffected, whereas the reflection signal measured during the light period will experience a significant boost.) Accordingly, the control system 106 monitoring the output of the sensor(s) 118 can detect an object in the region of interest 112 based on a change in one or more environmental illumination parameters such as environmental reflectivity that exceeds a predetermined threshold (e.g., by 10% or some other relative or absolute amount). As with changes in brightness, the threshold change can be set theoretically based on the configuration of the image-capture system and the monitored space as well as the expected objects of interest, and/or experimentally based on observed changes in reflectivity.

Computer System

Figure 2:
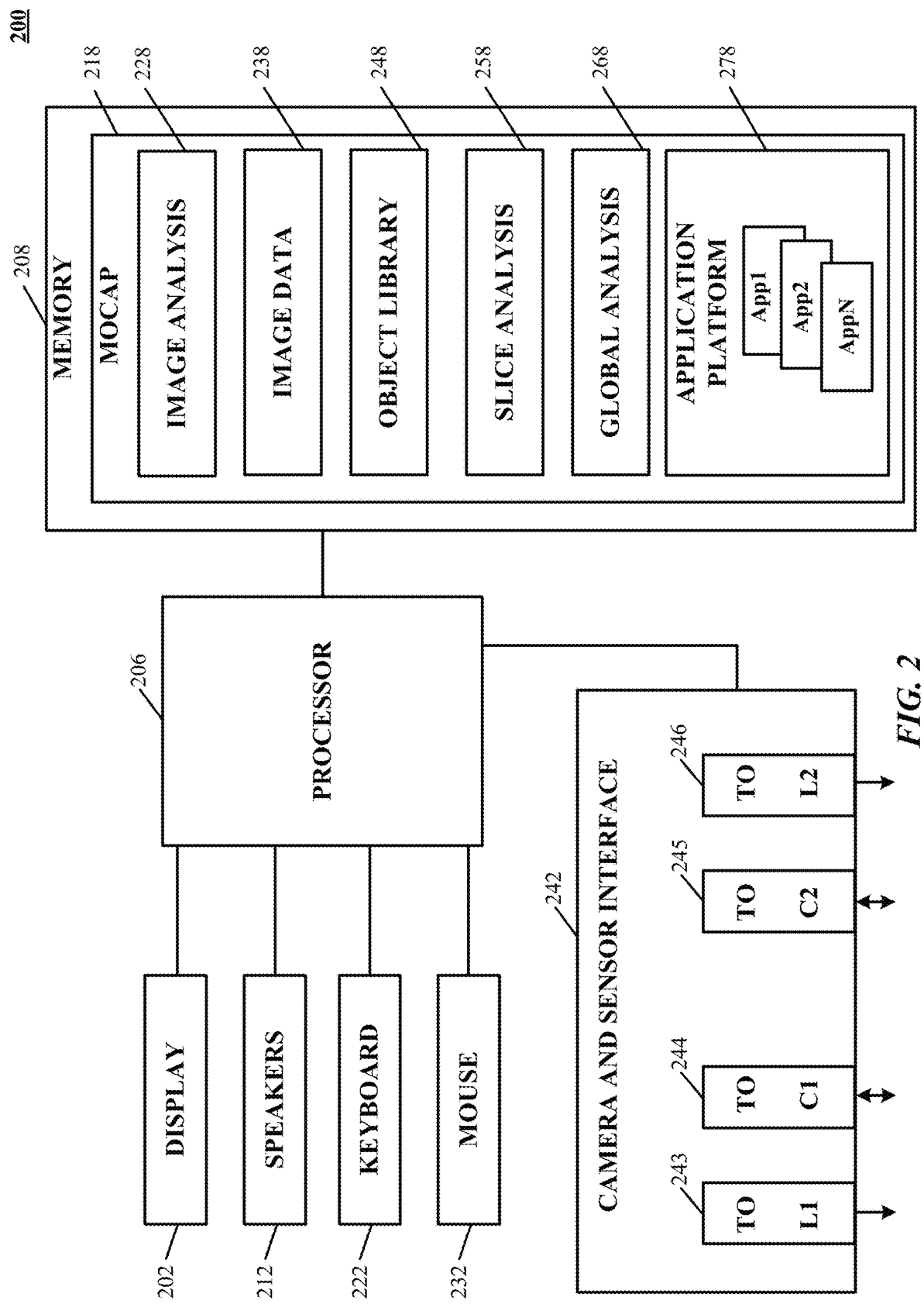
FIG. 2 is a simplified block diagram of a computer system implementing a gesture-recognition apparatus according to an implementation of the technology disclosed.

FIG. 2 is a simplified block diagram of a computer system 200, implementing all or portions of image analysis and motion capture system 106 according to an implementation of the technology disclosed. Image analysis and motion capture system 106 can include or consist of any device or device component that is capable of capturing and processing image data. In some implementations, computer system 200 includes a processor 206, memory 208, a sensor interface 242, a display 202 (or other presentation mechanism(s), e.g. holographic projection systems, wearable googles or other head mounted displays (HMDs), heads up displays (HUDs), other visual presentation mechanisms or combinations thereof, speakers 212, a keyboard 222, and a mouse 232. Memory 208 can be used to store instructions to be executed by processor 206 as well as input and/or output data associated with execution of the instructions. In particular, memory 208 contains instructions, conceptually illustrated as a group of modules described in greater detail below, that control the operation of processor 206 and its interaction with the other hardware components. An operating system directs the execution of low-level, basic system functions such as memory allocation, file management and operation of mass storage devices. The operating system can be or include a variety of operating systems such as Microsoft WINDOWS operating system, the Unix operating system, the Linux operating system, the Xenix operating system, the IBM AIX operating system, the Hewlett Packard UX operating system, the Novell NETWARE operating system, the Sun Microsystems SOLARIS operating system, the OS/2 operating system, the BeOS operating system, the MAC OS operating system, the APACHE operating system, an OPENACTION operating system, iOS, Android or other mobile operating systems, or another operating system platform.

The computing environment can also include other removable/non-removable, volatile/nonvolatile computer storage media. For example, a hard disk drive can read or write to non-removable, nonvolatile magnetic media. A magnetic disk drive can read from or write to a removable, nonvolatile magnetic disk, and an optical disk drive can read from or write to a removable, nonvolatile optical disk such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid physical arrangement RAM, solid physical arrangement ROM, and the like. The storage media are typically connected to the system bus through a removable or non-removable memory interface.

According to some implementations, cameras 102, 104 and/or light sources 108, 110 can connect to the computer 200 via a universal serial bus (USB), FireWire, or other cable, or wirelessly via Bluetooth, Wi-Fi, etc. The computer 200 can include a camera interface 242, implemented in hardware (e.g., as part of a USB port) and/or software (e.g., executed by processor 206), that enables communication with the cameras 102, 104 and/or light sources 108, 110. The camera interface 242 can include one or more data ports and associated image buffers for receiving the image frames from the cameras 102, 104; hardware and/or software signal processors to modify the image data (e.g., to reduce noise or reformat data) prior to providing it as input to a motion-capture or other image-processing program; and/or control signal ports for transmit signals to the cameras 102, 104, e.g., to activate or deactivate the cameras, to control camera settings (frame rate, image quality, sensitivity, etc.), or the like.

Processor 206 can be a general-purpose microprocessor, but depending on implementation can alternatively be a microcontroller, peripheral integrated circuit element, a CSIC (customer-specific integrated circuit), an ASIC (application-specific integrated circuit), a logic circuit, a digital signal processor, a programmable logic device such as an FPGA (field-programmable gate array), a PLD (programmable logic device), a PLA (programmable logic array), an RFID processor, smart chip, or any other device or arrangement of devices that is capable of implementing the actions of the processes of the technology disclosed.

Camera and sensor interface 242 can include hardware and/or software that enables communication between computer system 200 and cameras such as cameras 102, 104 shown in FIG. 1, as well as associated light sources such as light sources 108, 110 of FIG. 1. Thus, for example, camera and sensor interface 242 can include one or more data ports 244, 245 to which cameras can be connected, as well as hardware and/or software signal processors to modify data signals received from the cameras (e.g., to reduce noise or reformat data) prior to providing the signals as inputs to a motion-capture ("mocap") program 218 executing on processor 206. In some implementations, camera and sensor interface 242 can also transmit signals to the cameras, e.g., to activate or deactivate the cameras, to control camera settings (frame rate, image quality, sensitivity, etc.), or the like. Such signals can be transmitted, e.g., in response to control signals from processor 206, which can in turn be generated in response to user input or other detected events.

Camera and sensor interface 242 can also include controllers 243, 246, to which light sources (e.g., light sources 108, 110) can be connected. In some implementations, controllers 243, 246 provide operating current to the light sources, e.g., in response to instructions from processor 206 executing mocap program 218. In other implementations, the light sources can draw operating current from an external power supply, and controllers 243, 246 can generate control signals for the light sources, e.g., instructing the light sources to be turned on or off or changing the brightness. In some implementations, a single controller can be used to control multiple light sources.

Instructions defining mocap program 218 are stored in memory 208, and these instructions, when executed, perform motion-capture analysis on images supplied from cameras connected to sensor interface 242. In one implementation, mocap program 218 includes various modules, such as an image analysis module 228 or image data 238. Image analysis module 228 can analyze images (e.g., images captured via camera and sensor interface 242) to detect edges and/or features of an object therein and/or other information about the object's location. In one implementation, it can also analyze the object information to determine the 3D position and/or motion of the object (e.g., a user's hand). Slice analysis module 258 can analyze image data from a slice of an image as described below, to generate an approximate cross-section of the object in a particular plane. Global analysis module 268 can correlate cross-sections across different slices and refine the analysis. Examples of operations that can be implemented in code modules of mocap program 218 are described below. Examples of operations that can be implemented in code modules of mocap program 218 are described below.

The memory 208 can further store input and/or output data associated with execution of the instructions (including, e.g., input and output image data 238) as well as additional information used by the various software applications; for example, in some implementations, the memory 208 stores an object library 248 of canonical models of various objects of interest. As described below, an object detected in the camera images can be identified by matching its shape to a model in the object library 248, and the model can then inform further image analysis, motion prediction, etc.

The memory 208 can further store input and/or output data associated with execution of the instructions (including, e.g., input and output image data 238) as well as additional information used by the various software applications. In addition, the memory 208 can also include other information and/or code modules used by mocap program 218 such as an application platform 288, which allows a user to interact with the mocap program 218 using different applications like application 1 (App1), application 2 (App2), and application N (AppN).

Display 202, speakers 212, keyboard 222, and mouse 232 can be used to facilitate user interaction with computer system 200. In some implementations, results of motion capture using sensor interface 242 and mocap program 218 can be interpreted as user input. For example, a user can perform hand gestures that are analyzed using mocap program 218, and the results of this analysis can be interpreted as an instruction to some other program executing on processor 206 (e.g., a web browser, word processor, or other application). Thus, by way of illustration, a user might use upward or downward swiping gestures to "scroll" a webpage currently displayed on display 202, to use rotating gestures to increase or decrease the volume of audio output from speakers 212, and so on.

It will be appreciated that computer system 200 is illustrative and that variations and modifications are possible. Computer systems can be implemented in a variety of form factors, including server systems, desktop systems, laptop systems, tablets, smart phones or personal digital assistants, wearable devices, e.g., goggles, head mounted displays (HMDs), wrist computers, heads up displays (HUDs) for vehicles, and so on. A particular implementation can include other functionality not described herein, e.g., wired and/or wireless network interfaces, media playing and/or recording capability, etc. In some implementations, one or more cameras can be built into the computer or other device into which the sensor is imbedded rather than being supplied as separate components. Further, an image analyzer can be implemented using only a subset of computer system components (e.g., as a processor executing program code, an ASIC, or a fixed-function digital signal processor, with suitable I/O interfaces to receive image data and output analysis results).

In another example, in some implementations, the cameras 102, 104 are connected to or integrated with a special-purpose processing unit that, in turn, communicates with a general-purpose computer, e.g., via direct memory access ("DMA"). The processing unit can include one or more image buffers for storing the image data read out from the camera sensors, a GPU or other processor and associated memory implementing at least part of the motion-capture algorithm, and a DMA controller. The processing unit can provide processed images or other data derived from the camera images to the computer for further processing. In some implementations, the processing unit sends display control signals generated based on the captured motion (e.g., of a user's hand) to the computer, and the computer uses these control signals to adjust the on-screen display of documents and images that are otherwise unrelated to the camera images (e.g., text documents or maps) by, for example, shifting or rotating the images.

While computer system 200 is described herein with reference to particular blocks, it is to be understood that the blocks are defined for convenience of description and are not intended to imply a particular physical arrangement of component parts. Further, the blocks need not correspond to physically distinct components. To the extent that physically distinct components are used, connections between components (e.g., for data communication) can be wired and/or wireless as desired.

When a user performs a gesture that is captured by the cameras 102, 104 as a series of temporally sequential images. In other implementations, cameras 102, 104 can capture any observable pose or portion of a user. For instance, if a user walks into the field of view near the cameras 102, 104, cameras 102, 104 can capture not only the whole body of the user, but the positions of arms and legs relative to the person's core or trunk. These are analyzed by the mocap 218, which provides input to an electronic device, allowing a user to remotely control the electronic device and/or manipulate virtual objects, such as prototypes/models, blocks, spheres, or other shapes, buttons, levers, or other controls, in a virtual environment displayed on display 202. The user can perform the gesture using any part of her body, such as a finger, a hand, or an arm. As part of gesture recognition or independently, the image analysis and motion capture system 106 can determine the shapes and positions of the user's hand in 3D space and in real time; see, e.g., U.S. Ser. Nos. 61/587,554, 13/414,485, 61/724,091, and Ser. No. 13/724,357 filed on Jan. 17, 2012, Mar. 7, 2012, Nov. 8, 2012, and Dec. 21, 2012 respectively, the entire disclosures of which are hereby incorporated by reference. As a result, the image analysis and motion capture system processor 206 may not only recognize gestures for purposes of providing input to the electronic device, but can also capture the position and shape of the user's hand in consecutive video images in order to characterize the hand gesture in 3D space and reproduce it on the display screen 202.

In one implementation, the mocap 218 compares the detected gesture to a library of gestures electronically stored as records in a database, which is implemented in the image analysis and motion capture system 106, the electronic device, or on an external storage system. (As used herein, the term "electronically stored" includes storage in volatile or non-volatile storage, the latter including disks, Flash memory, etc., and extends to any computationally addressable storage media (including, for example, optical storage)

.) For example, gestures can be stored as vectors, i.e., mathematically specified spatial trajectories, and the gesture record can have a field specifying the relevant part of the user's body making the gesture; thus, similar trajectories executed by a user's hand and head can be stored in the database as different gestures so that an application can interpret them differently. Typically, the trajectory of a sensed gesture is mathematically compared against the stored trajectories to find a best match, and the gesture is recognized as corresponding to the located database entry only if the degree of match exceeds a threshold. The vector can be scaled so that, for example, large and small arcs traced by a user's hand will be recognized as the same gesture (i.e., corresponding to the same database record) but the gesture recognition module will return both the identity and a value, reflecting the scaling, for the gesture. The scale can correspond to an actual gesture distance traversed in performance of the gesture, or can be normalized to some canonical distance.

In various implementations, the motion captured in a series of camera images is used to compute a corresponding series of output images for presentation on the display 202. For example, camera images of a moving hand can be translated by the processor 206 into a wire-frame or other graphical representations of motion of the hand. In any case, the output images can be stored in the form of pixel data in a frame buffer, which can, but need not be, implemented, in main memory 208. A video display controller reads out the frame buffer to generate a data stream and associated control signals to output the images to the display 202. The video display controller can be provided along with the processor 206 and memory 208 on-board the motherboard of the computer 200, and can be integrated with the processor 206 or implemented as a co-processor that manipulates a separate video memory.

In some implementations, the computer 200 is equipped with a separate graphics or video card that aids with generating the feed of output images for the display 202. The video card generally includes a graphical processing unit ("GPU") and video memory, and is useful, in particular, for complex and computationally expensive image processing and rendering. The graphics card can implement the frame buffer and the functionality of the video display controller (and the on-board video display controller can be disabled). In general, the image-processing and motion-capture functionality of the system 200 can be distributed between the GPU and the main processor 206.

In some implementations, the mocap program 218 detects more than one gesture. The user can perform an arm-waving gesture while flexing his or her fingers. The mocap program 218 detects the waving and flexing gestures and records a waving trajectory and five flexing trajectories for the five fingers. Each trajectory can be converted into a vector along, for example, six Euler degrees of freedom in Euler space. The vector with the largest magnitude can represent the dominant component of the motion (e.g., waving in this case) and the rest of vectors can be ignored. In one implementation, a vector filter that can be implemented using conventional filtering techniques is applied to the multiple vectors to filter the small vectors out and identify the dominant vector. This process can be repetitive, iterating until one vector—the dominant component of the motion— is identified. In some implementations, a new filter is generated every time new gestures are detected.

If the mocap program 218 is implemented as part of a specific application (such as a game or controller logic for a television), the database gesture record can also contain an input parameter corresponding to the gesture (which can be scaled using the scaling value); in generic systems where the mocap program 218 is implemented as a utility available to multiple applications, this application-specific parameter is omitted: when an application invokes the mocap program 218, it interprets the identified gesture according in accordance with its own programming.

In one implementation, the mocap program 218 breaks up and classifies one or more gestures into a plurality of gesture primitives. Each gesture can include or correspond to the path traversed by an object, such as user's hand or any other object (e.g., an implement such as a pen or paintbrush that the user holds), through 3D space. The path of the gesture can be captured by the cameras 102, 104 in conjunction with mocap 218, and represented in the memory 208 as a set of coordinate (x, y, z) points that lie on the path, as a set of vectors, as a set of specified curves, lines, shapes, or by any other coordinate system or data structure. Any method for representing a 3D path of a gesture on a computer system is within the scope of the technology disclosed.

Of course, the system 200 under control need not be a desktop computer. In other implementations, free-space gestures can be used to operate a handheld tablet or smart phone. The tablet can be connected, e.g., via a USB cable (or any other wired or wireless connection), to a motion-capture device (such as for example, a dual-camera motion controller as provided by Leap Motion, Inc., San Francisco, Calif. or other interfacing mechanisms and/or combinations thereof) that is positioned and oriented so as to monitor a region where hand motions normally take place. For example, the motion-capture device can be placed onto a desk or other working surface, and the tablet can be held at an angle to that working surface to facilitate easy viewing of the displayed content. The tablet can be propped up on a tablet stand or against a wall or other suitable vertical surface to free up the second hand, facilitating two-hand gestures. In a modified tablet implementation, the motion-capture device can be integrated into the frame of the tablet or smart phone.

3D Solid Hand Model

Gesture-recognition system 106 not only can recognize gestures for purposes of providing input to the electronic device, but can also capture the position and shape of the user's hand 114 in consecutive video images in order to characterize a hand gesture in 3D space and reproduce it on the display screen 202. A 3D model of the user's hand is determined from a solid hand model covering one or more capsule elements built from the images using techniques described below with reference to FIGS. 3A-3F.

Figure 3A:
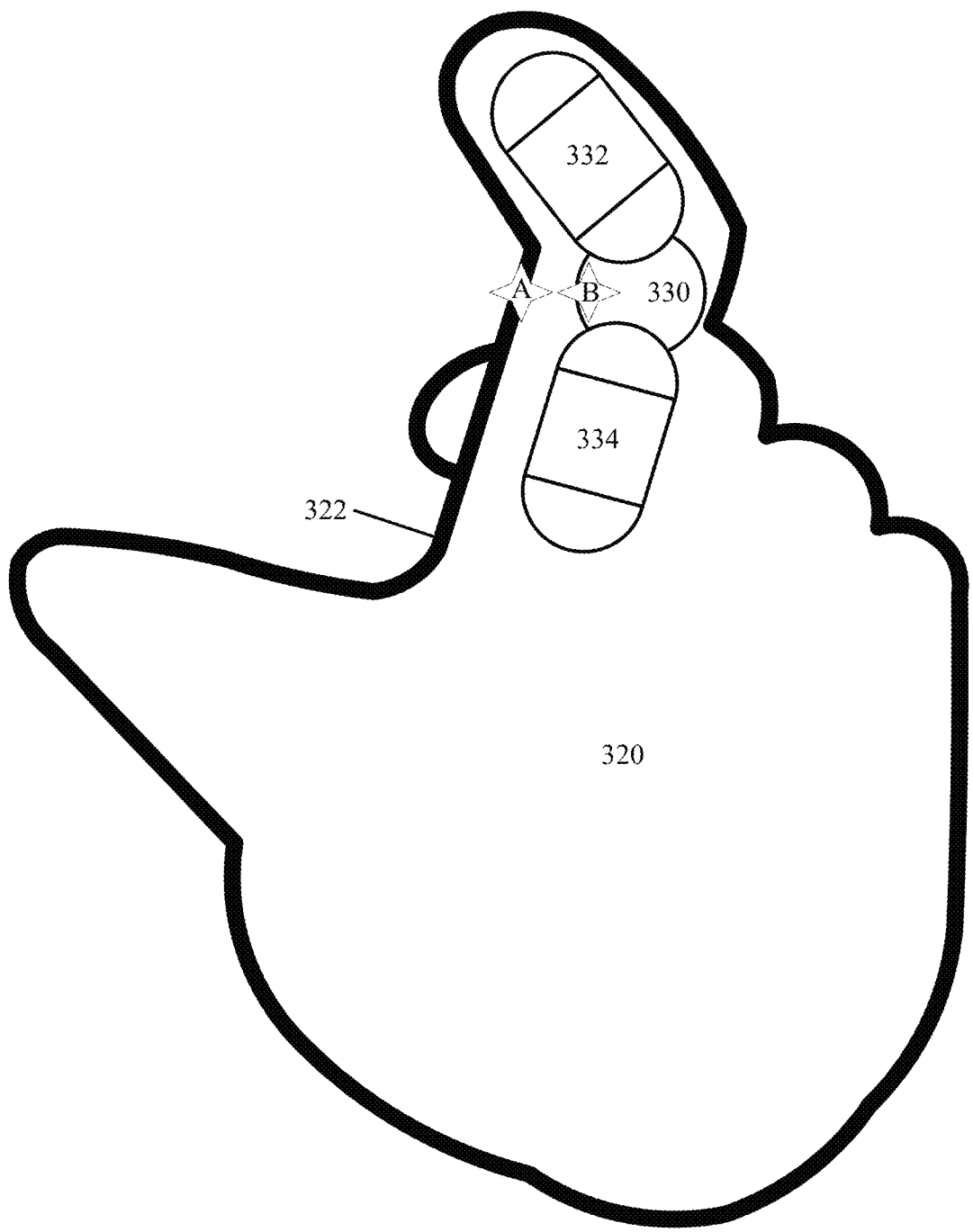
FIG. 3A shows one implementation of a 3D solid model hand with capsule representation of predictive information of a hand.

FIG. 3A shows one implementation of a 3D solid hand model 300A with capsule representation of predictive information of the hand 114. Some examples of predictive information of the hand include finger segment length, distance between finger tips, joint angles between fingers, and finger segment orientation. As illustrated by FIG. 3A, the prediction information can be constructed from one or more model subcomponents referred to as capsules 330, 332, and 334, which are selected and/or configured to represent at least a portion of a surface of the hand 114 and virtual surface portion 322. In some implementations, the model subcomponents can be selected from a set of radial solids, which can reflect at least a portion of the hand 114 in terms of one or more of structure, motion characteristics, conformational characteristics, other types of characteristics of hand 114, and/or combinations thereof. In one implementation, radial solids are objects made up of a 1D or 2D primitive (e.g., line, curve, plane) and a surface having a constant radial distance to the 1D or 2D primitive. A closest point to the radial solid can be computed relatively quickly. As used herein, three or greater capsules are referred to as a "capsoodle."

Figure 8A:
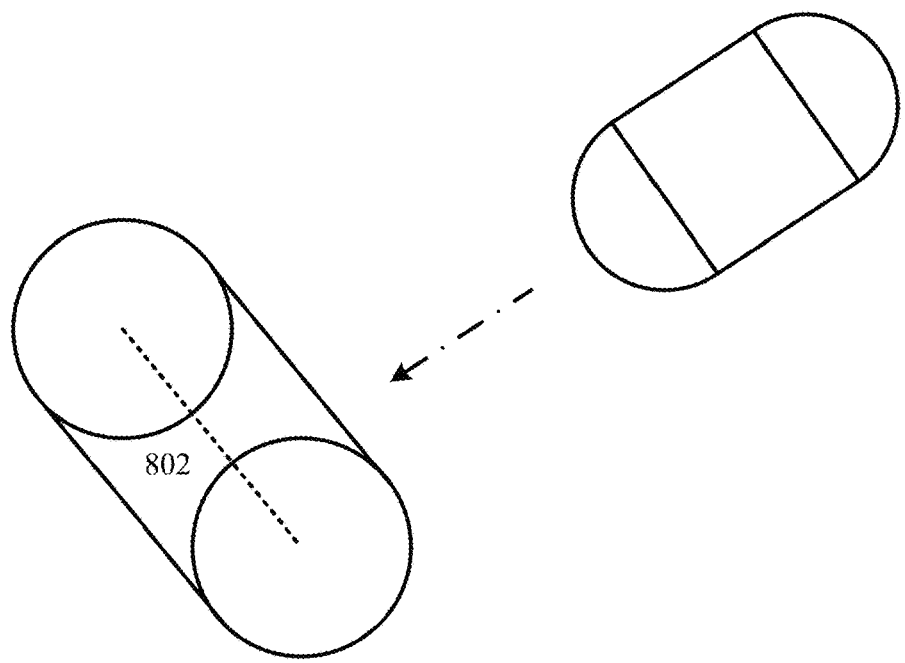
FIGS. 8A and 8B are simplified illustrations of fitting one or more 3D solid subcomponents to the observation information according to an implementation.
Figure 8B:
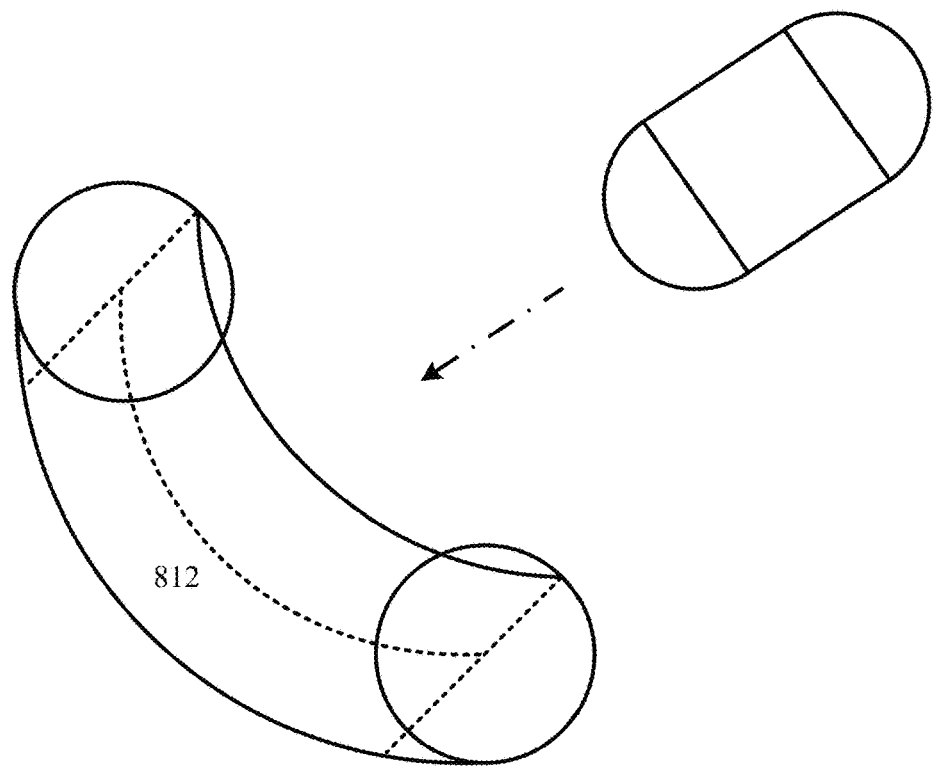

FIGS. 8A and 8B are simplified illustrations of fitting one or more 3D solid subcomponents to the observation information according to an implementation. One radial solid implementation includes a contour (802, 812) and a surface defined by a set of points having a fixed distance from the closest corresponding point on the contour. Another radial solid implementation includes a set of points normal to points on a contour and a fixed distance therefrom. In one implementation, computational technique(s) for defining the radial solid include finding a closest point on the contour and the arbitrary point, then projecting outward the length of the radius of the solid. In another implementation, such projection can be a vector normal to the contour at the closest point. In one example, the contour is a straight line segment along a lengthwise longitudinal axis of a closed curve, such as one contour 802. In another example, the contour is a curvilinear line segment along a lengthwise longitudinal axis of a closed curve, such as one contour 812. An example radial solid (e.g., 332, 334) includes a "capsuloid," i.e., a capsule shaped solid including a cylindrical body and semi-spherical ends. Another type of radial solid (e.g., 330) includes a sphere. Different types of radial solids can be identified based on the foregoing teaching in other implementations.

One or more attributes can define characteristics of a model subcomponent or capsule. Attributes can include e.g., sizes, rigidity, flexibility, torsion, ranges of motion with respect to one or more defined points that can include endpoints in some examples. In one implementation, predictive information about the hand 114 can be formed to include a 3D solid model 300A of the hand 114 together with attributes defining the model and values of those attributes.

In some implementations, when the hand 114 morphs, conforms, and/or translates, motion information reflecting such motion(s) is included as observation information about the motion of the hand 114. Points in space can be recomputed based on the new observation information. The model subcomponents can be scaled, sized, selected, rotated, translated, moved, or otherwise re-ordered to enable portions of the model corresponding to the virtual surface(s) to conform within the set of points in space.

In an implementation, observation information including observation of the control object can be compared against the model at one or more of periodically, randomly or substantially continuously (i.e., in real time). A "control object" as used herein with reference to an implementation is generally any three-dimensionally movable object or appendage with an associated position and/or orientation (e.g., the orientation of its longest axis) suitable for pointing at a certain location and/or in a certain direction. Control objects include, e.g., hands, fingers, feet, or other anatomical parts, as well as inanimate objects such as pens, styluses, handheld controls, portions thereof, and/or combinations thereof. Where a specific type of control object, such as the user's finger, is used hereinafter for ease of illustration, it is to be understood that, unless otherwise indicated or clear from context, any other type of control object can be used as well.

Observational information can include without limitation observed values of attributes of the control object corresponding to the attributes of one or more model subcomponents in the predictive information for the control object. In an implementation, comparison of the model with the observation information provides an error indication. In an implementation, an error indication can be computed by determining a closest distance determined between a first point A belonging to a set of points defining the virtual surface 322 and a second point B belonging to a model subcomponent 330 determined to be corresponding to the first point (e.g., nearest to the first point for example). In an implementation, the error indication can be applied to the predictive information to correct the model to more closely conform to the observation information. In an implementation, error indication can be applied to the predictive information repeatedly until the error indication falls below a threshold, a measure of conformance with the observation information rises above a threshold, or a fixed or variable number of times, or a fixed or variable number of times per time period, or combinations thereof.

Figure 7A:
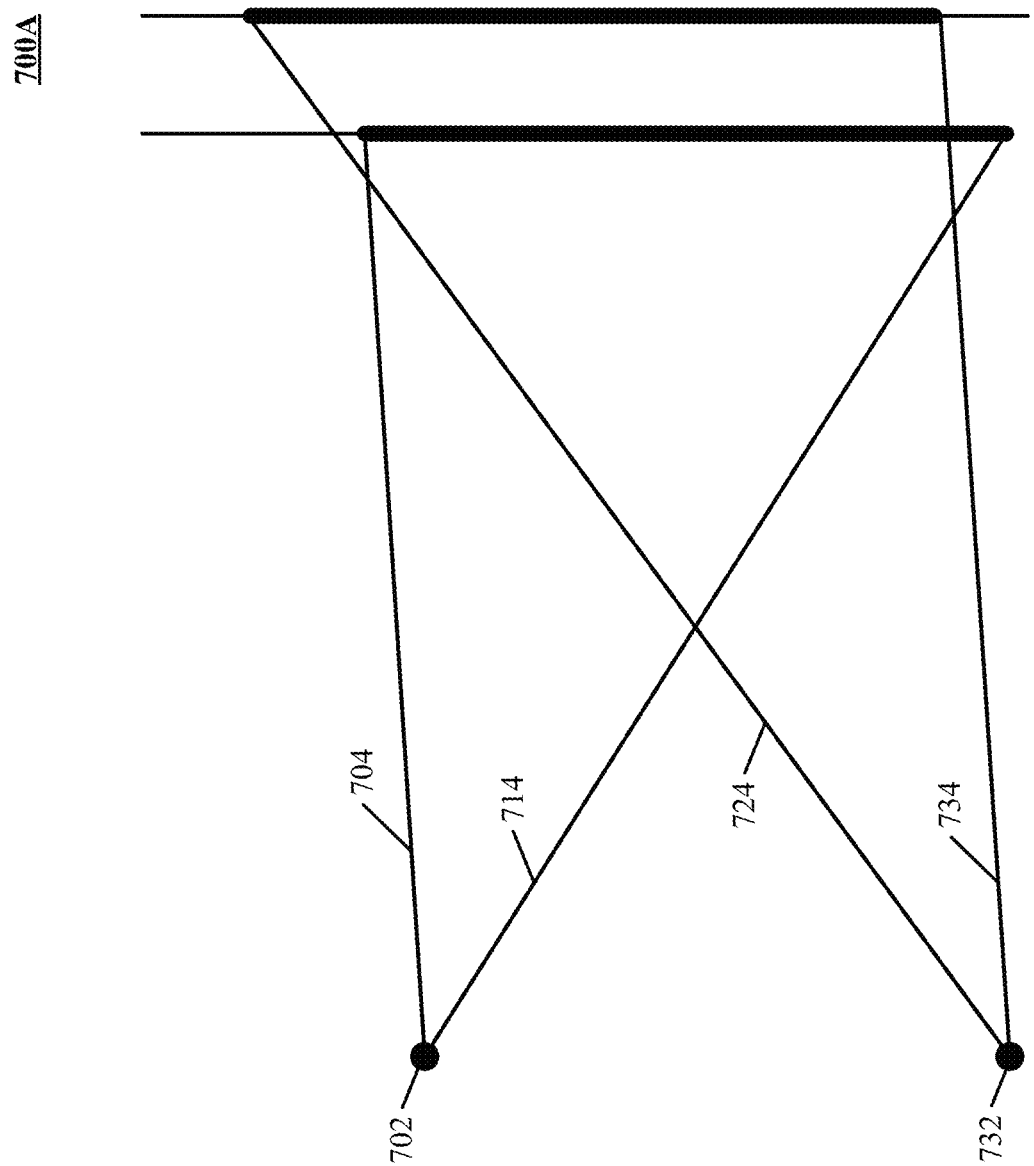
FIGS. 7A and 7B graphically illustrates one implementation of determining observation information.
Figure 7B:
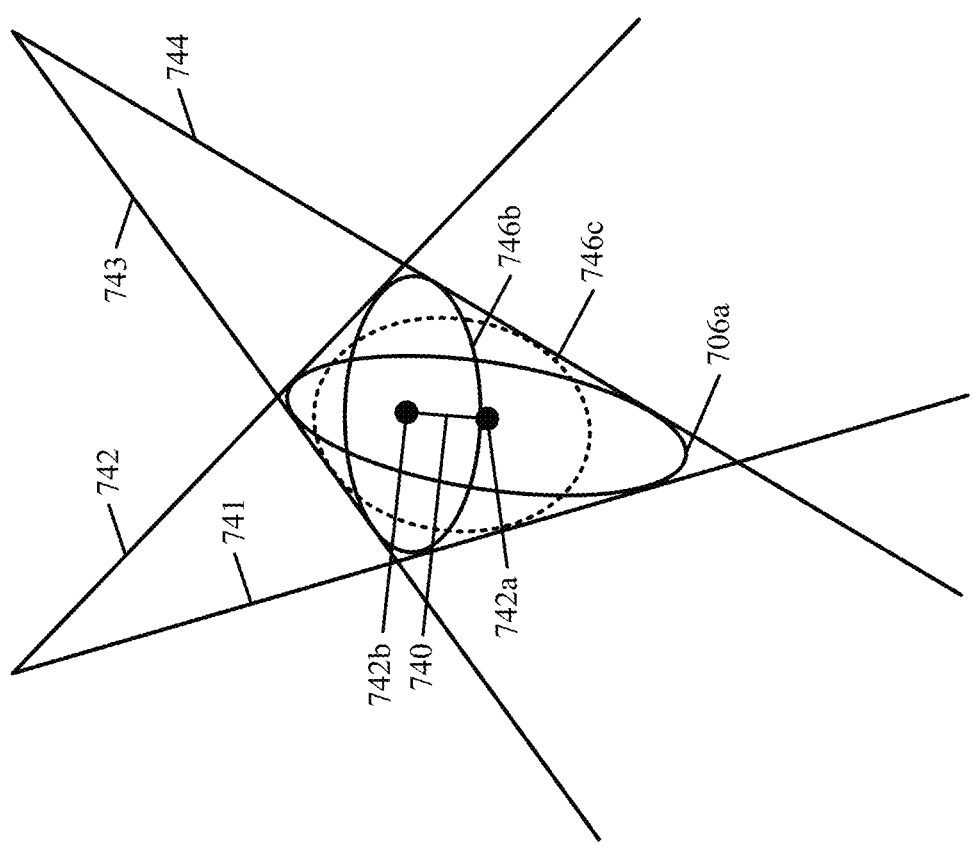

FIGS. 7A and 7B graphically illustrates one implementation of determining observation information 700A and 700B. In an implementation, comparing predictive information to observation information can be achieved by selecting one or more sets of points in space surrounding or bounding the control object within a field of view of one or more image capture device(s). As shown by FIG. 7A, points in space can be determined using one or more sets of lines 704, 714, 724, 734 originating at point(s) of view 732, 702 associated with the image capture device(s) (e.g., FIG. 1: 102, 104) and determining therefrom one or more intersection point(s) defining a bounding region (i.e., region formed by lines FIG. 7B: 741, 742, 743, and 744) surrounding a cross-section of the control object. The bounding region can be used to define a virtual surface (FIG. 7A: 746a, 746b, 746c) to which model subcomponents can be compared. In an implementation, the virtual surface can include straight portions, curved surface portions, and/or combinations thereof.

Figure 3B:
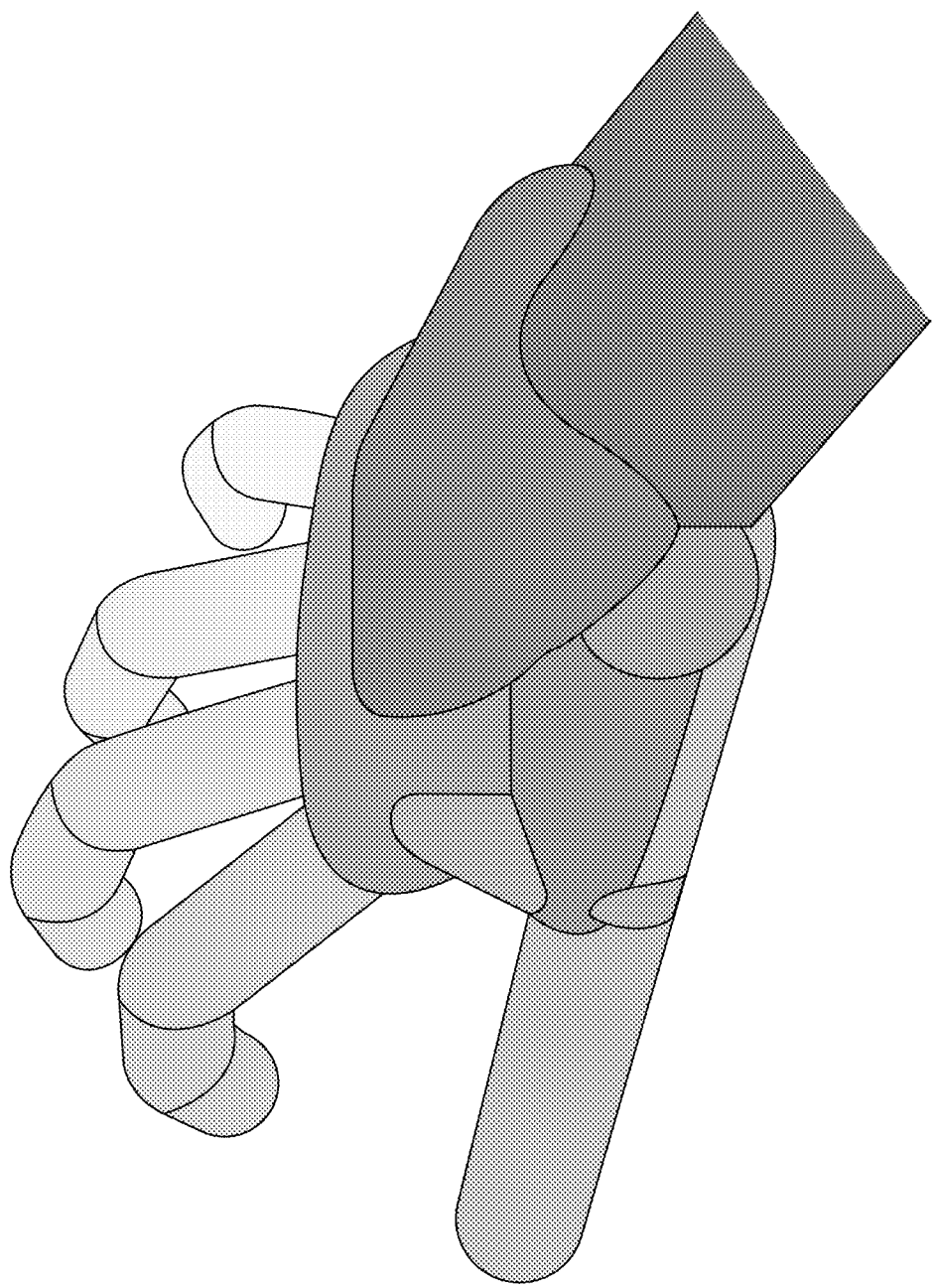
Figure 3D:
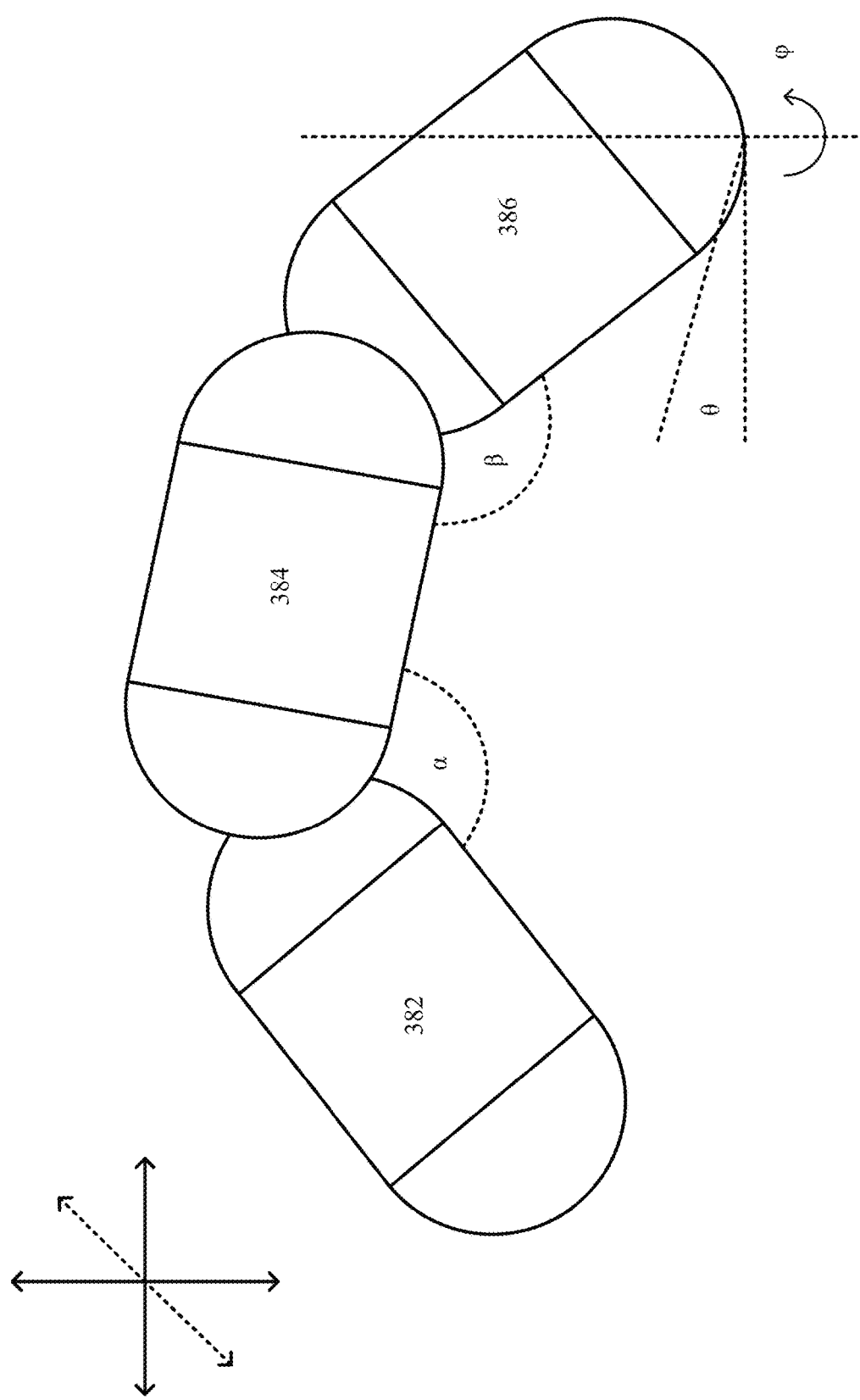
FIG. 3D depicts one implementation of generating a 3D finger capsuloid of a hand with different joint angles.

In one implementation and with reference to FIGS. 3B and 3C, a collection of radial solids and/or capsuloids can be considered a "capsule hand." In particular, FIGS. 3B and 3C illustrate different views 300B and 300C of a 3D capsule hand. A number of capsuloids 372, e.g. five (5), are used to represent fingers on a hand while a number of radial solids 374 are used to represent the shapes of the palm and wrist. With reference to FIG. 3D, a finger capsuloid 300C with radial solids 382, 384, and 386 can be represented by its two (2) joint angles ($\alpha$, $\beta$), pitch ($\theta$), and yaw ($\varphi$). In an implementation, the angle $\theta$ can be represented as a function of joint angle $\alpha$, pitch $\theta$, and yaw $\varphi$. Allowing angle $\theta$ to be represented this way can allow for faster representation of the finger capsuloid with fewer variables; see, e.g., U.S. Serial Nos. 61/871,790, filed 28 Aug. 2013 and 61/873,758, filed 4 Sep. 2013. For example, one capsule hand can include five (5) capsules for each finger, a radial polygon defining a base of the hand, and a plurality of definitional capsules that define fleshy portions of the hand. In some implementations, the capsule hand 300B is created using stereo matching, depth maps, or by finding contours and/or feature points reduced to certain finite number of degrees of freedom as shown in FIG. 3F, so as to enable simplification of problems of inverse kinematics (IK), sampling sizes, pose determination, etc.

Figure 3E:
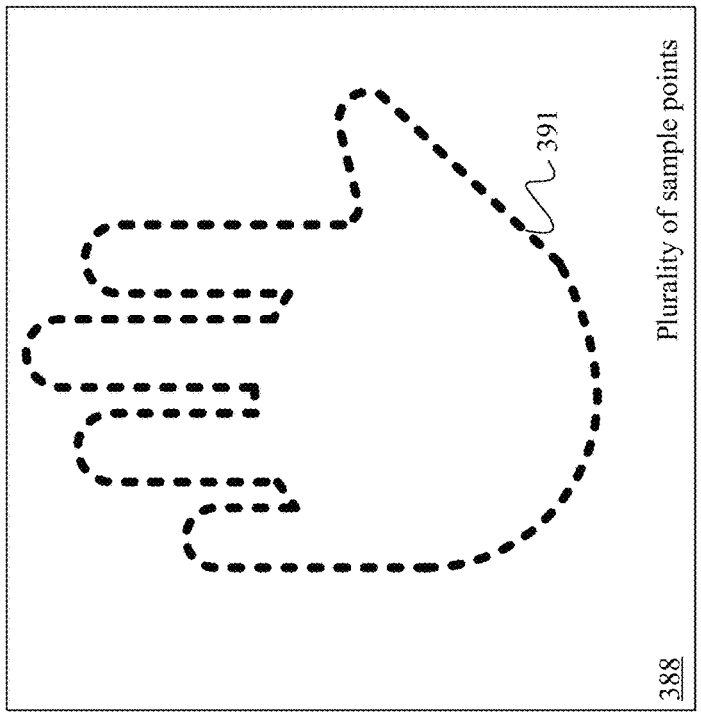
FIG. 3E is one implementation of determining spans and span lengths of a control object.
Figure 3E:
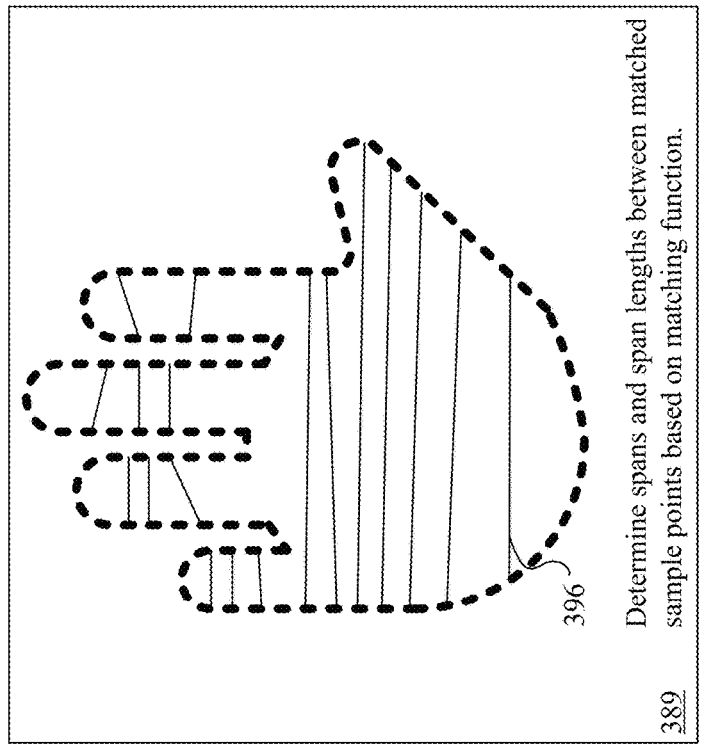
Figure 3E:
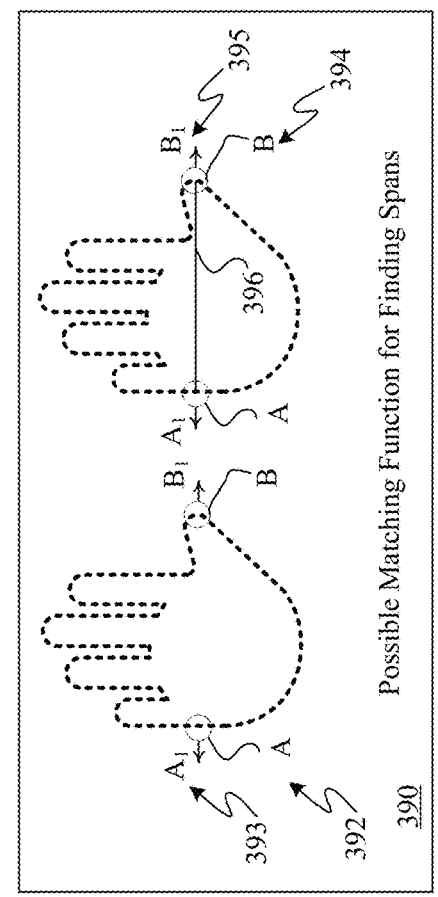
Figure 3F:
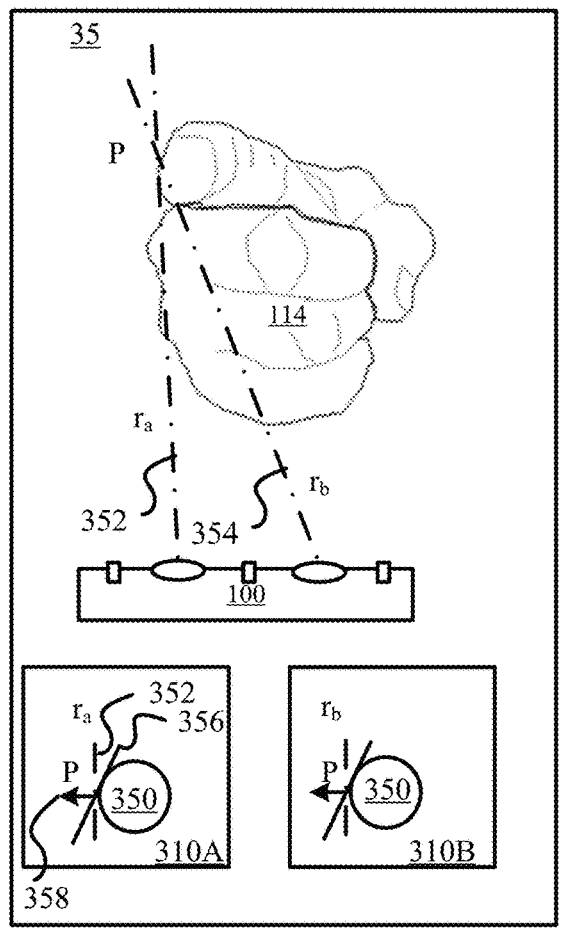
FIG. 3F illustrates one implementation of finding points in an image of an object being modeled.
Figure 3F:
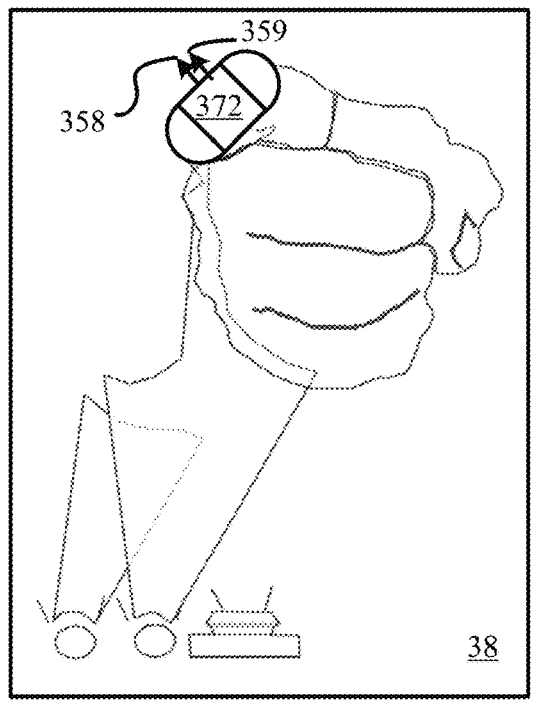

FIG. 3E depicts determination of spans and span lengths 300D in the observation information about the hand 114 in which one or more point pairings are selected from a surface portion as represented in the observation information. As illustrated by block 388 of FIG. 3E, an observed surface portion 391 (i.e., of observation information) can include a plurality of sample points from which one or more point pairings can be selected. In a block 390 of FIG. 3E, a point pairing between point A and point B of observed surface portion 391 are selected by application of a matching function. One method for determining a point pairing using a matching function is illustrated by FIG. 3E, in which a first unmatched (arbitrary) point A on a contour (of block 390 of FIG. 3E) representing a surface portion of interest in the observation information is selected as a starting point 392. A normal $A_1$ 393 (of block 390 of FIG. 3E) is determined for the point A. A wide variety of techniques for determining a normal can be used in implementations, but in one example implementation, a set of points proximate to the first unmatched point, at least two of which are not co-linear, is determined. Then, a normal for the first unmatched point can be determined using the other points in the set by determining a normal perpendicular to the plane. For example, given points $P_1$, $P_2$, $P_3$, the normal n is given by the cross product:

$$n=(p_2-p_1)\times(p_3-p_1),$$

Another technique that can be used: (i) start with the set of points; (ii) form a first vector from $P_2-P_1$, (iii) apply rotation matrix to rotate the first vector 90 degrees away from the center of mass of the set of points. (The center of mass of the set of points can be determined by an average of the points). A yet further technique that can be used includes: (i) determine a first vector tangent to a point on a contour in a first image; (ii) determine from the point on the contour a second vector from that point to a virtual camera object in space; (iii) determine a cross product of the first vector and the second vector. The cross product is a normal vector to the contour.

Again with reference to FIG. 3E, the closest second unmatched point B 394 (of block 390 of FIG. 3E) reachable by a convex curve (line 396) having the most opposite normal $B_1$ 395 is found. Accordingly, points A and B form a point pairing. In FIG. 3E, a span length is determined for at least one of the one or more point pairings selected. Now with reference to block 389 of FIG. 3E, one or more spans and span lengths are determined for the one or more point pairings. In a representative implementation, a span can be found by determining a shortest convex curve for the point pairings A and B. It is determined whether the convex curve passes through any other points of the model. If so, then another convex curve is determined for paired points A and B. Otherwise, the span comprises the shortest continuous segment found through paired points A and B that only intersects the model surface at paired points A and B. In an implementation, the span can comprise a convex geodesic segment that only intersects the model at two points. A span can be determined from any two points using the equation of a line fitted to the paired points A and B for example.

FIG. 3F illustrates an implementation of finding points in an image of an object being modeled. Now with reference to block 35 of FIG. 3F, cameras 102, 104 are operated to collect a sequence of images (e.g., 310A, 310B) of the object 114. The images are time correlated such that an image from camera 102 can be paired with an image from camera 104 that was captured at the same time (or within a few milliseconds). These images are then analyzed by object detection module 228 that detects the presence of one or more objects 350 in the image, and object analysis module 238 analyzes detected objects to determine their positions and shape in 3D space. If the received images 310A, 310B include a fixed number of rows of pixels (e.g., 1080 rows), each row can be analyzed, or a subset of the rows can be used for faster processing. Where a subset of the rows is used, image data from adjacent rows can be averaged together, e.g., in groups of two or three.

Again with reference to block 35 in FIG. 3F, one or more rays 352 can be drawn from the camera(s) proximate to an object 114 for some points P, depending upon the number of vantage points that are available. One or more rays 352 can be determined for some point P on a surface of the object 350 in image 310A. A tangent 356 to the object surface at the point P can be determined from point P and neighboring points. A normal vector 358 to the object surface 350 at the point P is determined from the ray and the tangent by cross product or other analogous technique. In block 38, a model portion (e.g., capsule 387) can be aligned to object surface 350 at the point P based upon the normal vector 358 and a normal vector 359 of the model portion 372. Optionally, as shown in block 35, a second ray 354 is determined to the point P from a second image 310B captured by a second camera. In some instances, fewer or additional rays or constraints from neighboring capsule placements can create additional complexity or provide further information. Additional information from placing neighboring capsules can be used as constraints to assist in determining a solution for placing the capsule. For example, using one or more parameters from a capsule fit to a portion of the object adjacent to the capsule being placed, e.g., angles of orientation, the system can determine a placement, orientation and shape/size information for the capsule. Object portions with too little information to analyze can be discarded or combined with adjacent object portions.

Figure 4A:
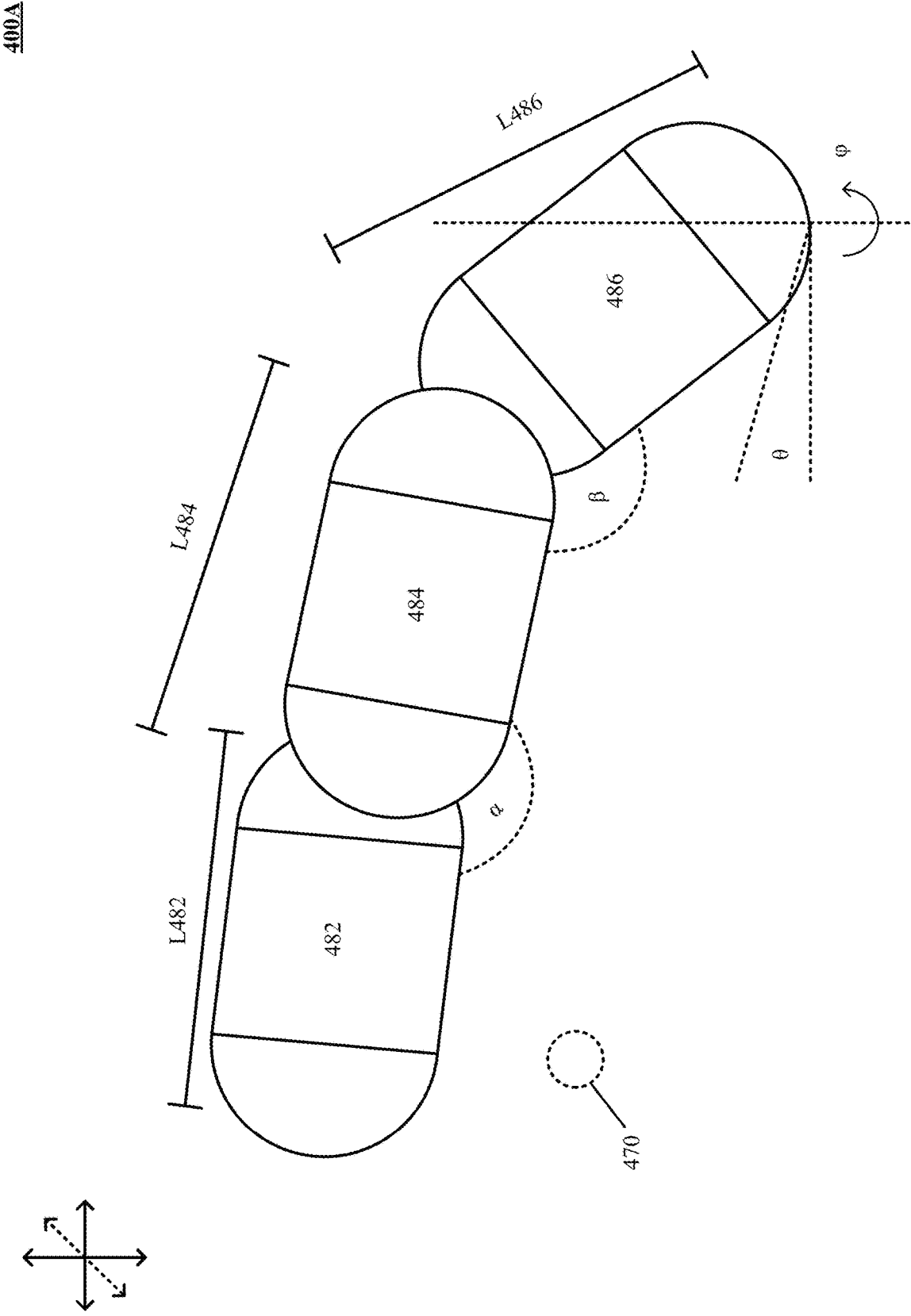
FIGS. 4A and 4B are one implementation of determination and reconstruction of fingertip position of a hand.
Figure 4B:
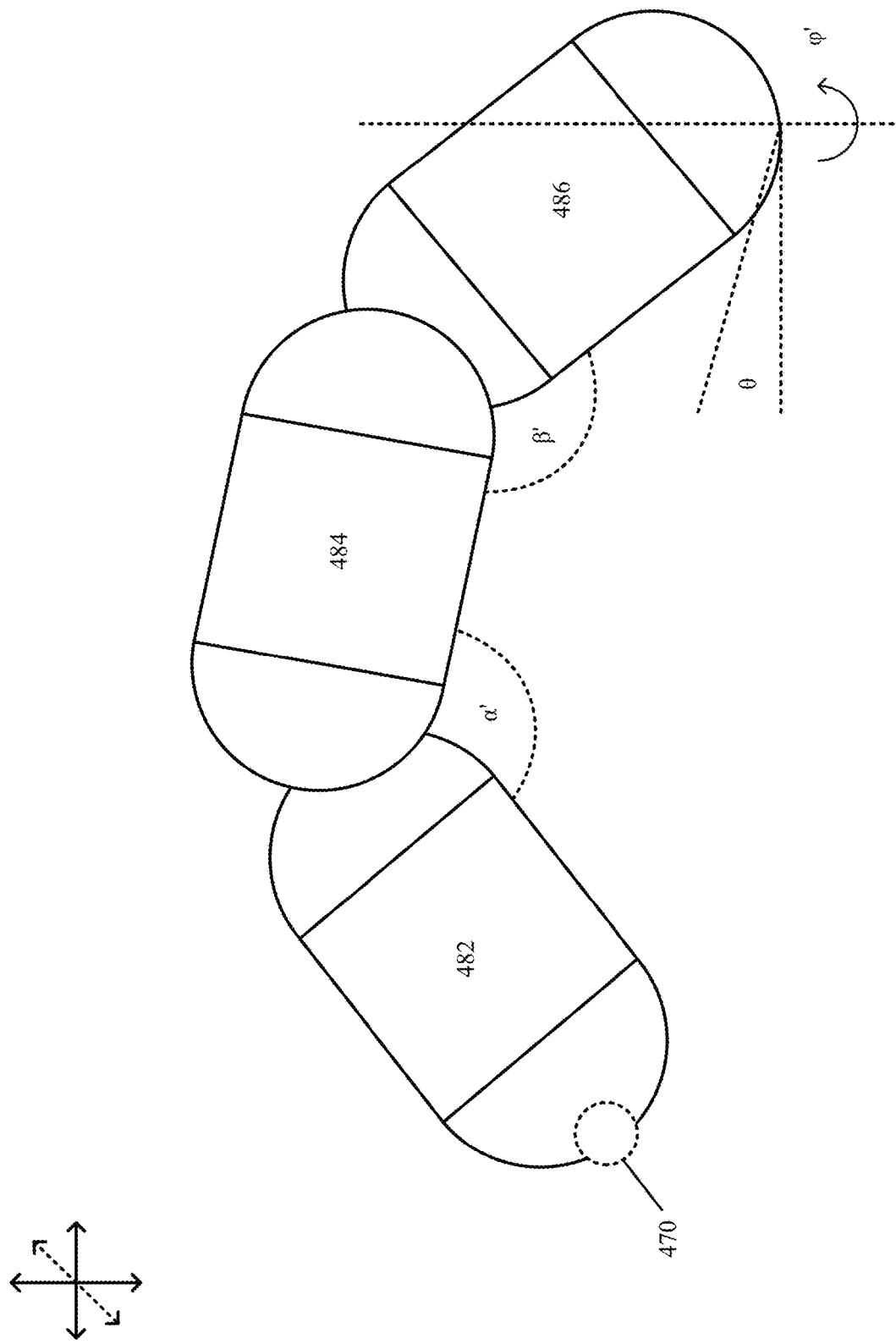

In one implementation, as illustrated by FIGS. 4A-4B, a fingertip position 400A-B can be determined from an image and can be reconstructed in 3D space. In FIG. 4A, a point 470 is an observed fingertip. Model 482, 484, and 486 are aligned such that the tip of 482 is coincident with the location in space of point 470 determined from the observation information. In one technique, angle α and angle β are allowed to be set equal, which enables a closed form solution for θ and φ as well as angle α and angle β.

$$s^2=2ac(-2a^2-2c^2+b^2-2a-2b-2c+4ac)+-2b^2(a^2+c^2)$$

$$\alpha=\beta=\tan 2^{-1}s-(a+c)b$$

$$\varphi=x_1/\text{norm}(x)$$

$$\theta=x_2/\text{norm}(x)$$

Wherein norm(x) can be described as the norm of a 3D point x (470 in FIG. 4B) with a, b and c being capsule lengths L482, L484, L486 in FIG. 4A.

Figure 5:
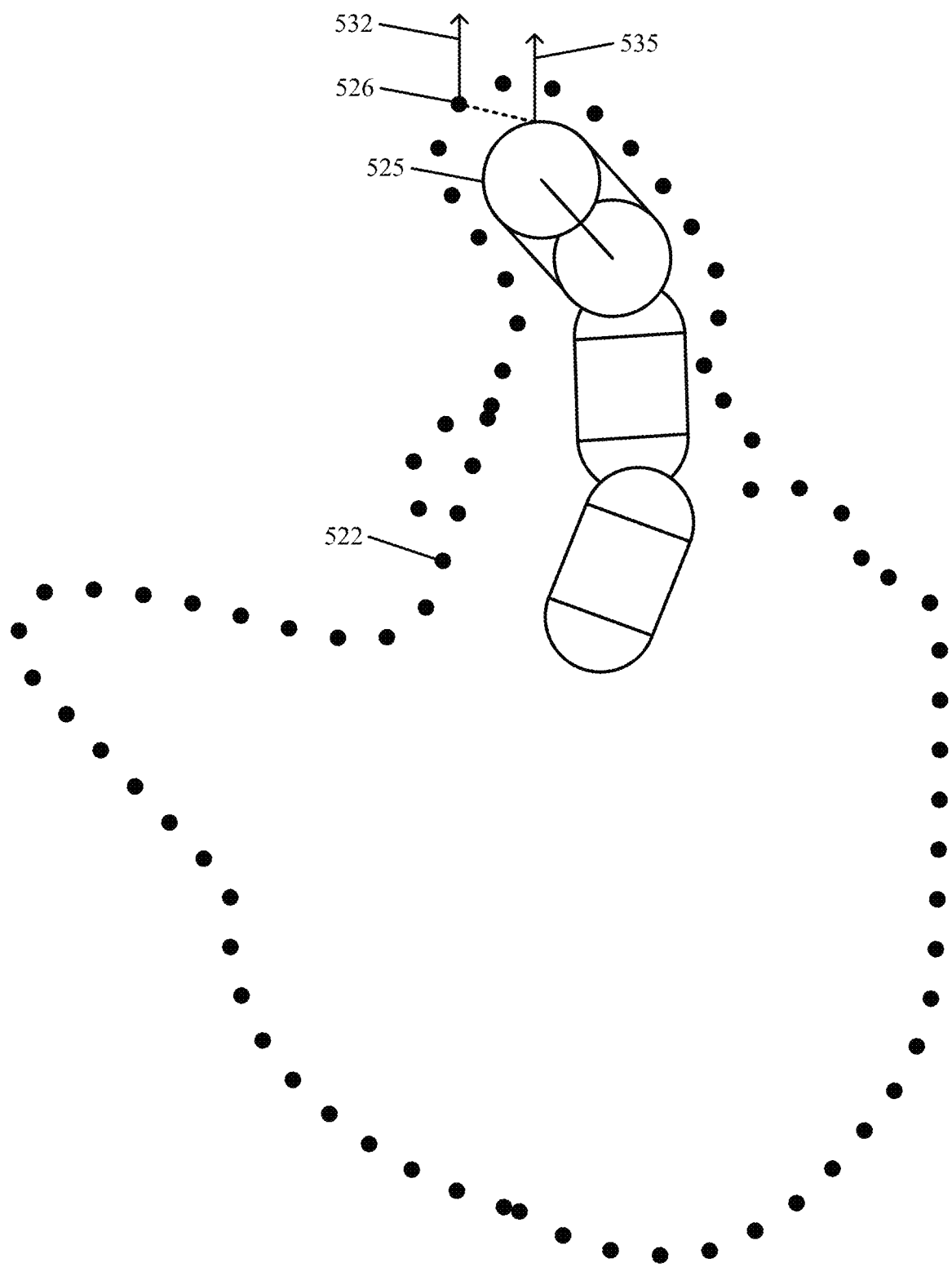
FIG. 5 shows one implementation of improving capsule representation of predictive information.

FIG. 5 illustrates one implementation of improving 500 capsule representation of predictive information. In one implementation, observation information 522 including observation of the control object (such as hand 114) can be compared against the 3D solid hand model at least one of periodically, randomly or substantially continuously (i.e., in real-time). Observational information 522 can include without limitation observed values of attributes of the control object corresponding to the attributes of one or more model subcomponents in the predictive information for the control object. In another implementation, comparison of the model 524 with the observation information 522 provides an error indication 526. In an implementation, an error indication 526 can be computed by first associating a set A of 3D points with a corresponding normal direction 532 to a set B of 3D points with a corresponding normal direction 534 on the subcomponents surface. The association can be done in a manner that assures that each paired point in set A and B has the same associated normal. An error can then be computed by summing the distances between each point in set A and B. This error is here on referred to the association error; see, e.g., U.S. Ser. No. 61/873,758, filed Sep. 4, 2013.

Predictive information of the 3D hand model can be aligned to the observation information using any of a variety of techniques. Aligning techniques bring model portions (e.g., capsules, capsuloids, capsoodles) into alignment with the information from the image source (e.g., edge samples, edge rays, interior points, 3D depth maps, and so forth). In one implementation, the model is rigidly aligned to the observation information using iterative closest point (ICP) technique. The model can be non-rigidly aligned to the observation information by sampling techniques.

One ICP implementation includes finding an optimal rotation R and translation T from one set of points A to another set of points B. First each point from A is matched to a point in set B. A mean square error is computed by adding the error of each match:

$$MSE=\text{sqrt}(\Sigma(R^*x_i+T-y_i)^{t}*(R^*x_i+T-y_i))$$

An optimal R and T can be computed and applied to the set of points A or B, in some implementations.

In order to enable the ICP to match points to points on the model, a capsule matching technique can be employed. One implementation of the capsule matcher includes a class that "grabs" the set of data and computes the closest point on each tracked hand (using information like the normal). Then the minimum of those closest points is associated to the corresponding hand and saved in a structure called "Hand Data." Other points that don't meet a minimal distance threshold can be marked as unmatched.

In an implementation, motion(s) of the control object can be rigid transformation, in which case, points on the virtual surface(s) remain at the same distance(s) from one another through the motion. Motion(s) can be non-rigid transformations, in which points on the virtual surface(s) can vary in distance(s) from one another during the motion. In an implementation, observation information can be used to adjust (and/or recomputed) predictive information thereby enabling "tracking" the control object. In implementations, control object can be tracked by determining whether a rigid transformation or a non-rigid transformation occurs. In an implementation, when a rigid transformation occurs, a transformation matrix is applied to each point of the model uniformly. Otherwise, when a non-rigid transformation occurs, an error indication can be determined, and an error minimization technique such as described herein above can be applied.

In some implementations, rigid transformations and/or non-rigid transformations can be composed. One example composition implementation includes applying a rigid transformation to predictive information. Then an error indication can be determined, and an error minimization technique such as described herein above can be applied. In an implementation, determining a transformation can include determining a rotation matrix that provides a reduced RMSD (root mean squared deviation) between two paired sets of points. One implementation can include using Kabsch Algorithm to produce a rotation matrix. The Kabsch algorithm can be used to find an optimal rotation R and translation T that minimizes the error:

$$RMS=\text{sqrt}(\Sigma(R^*x_i+T-y_i)^{t}*(R^*x_i+T-y_i))w_i$$

The transformation (both R and T) are applied rigidly to the model, according to one implementation. The capsule matching and rigid alignment can be repeated until convergence. In one implementation, the Kabsch can be extended to ray or co-variances by the following minimizing:

$$\Sigma(R^*x_i+T-y_i)^{t}*M_i*(R^*x_i+T-y_i)$$

In the equation above, $M_i$ is a positive definite symmetric matrix. In other implementations and by way of example, one or more force lines can be determined from one or more portions of a virtual surface.

One implementation applies non-rigidly alignment to the observed by sampling the parameters of each finger. A finger is represented by a 3D vector where the entry of each vector is Pitch, Yaw and Bend of the finger. The Pitch and Yaw can be defined trivially. The bend is the angle between the first and second Capsule and the second and third Capsule which are set to be equal. The mean of the samples weighted by the RMS is taken to be the new finger parameter. After Rigid Alignment all data that has not been assigned to a hand, can be used to initialize a new object (hand or tool).

In an implementation, predictive information can include collision information concerning two or more capsoloids. By means of illustration, several possible fits of predicted information to observation information can be removed from consideration based upon a determination that these potential solutions would result in collisions of capsoloids.

In an implementation, a relationship between neighboring capsoloids, each having one or more attributes (e.g., determined minima and/or maxima of intersection angles between capsoloids) can be determined. In an implementation, determining a relationship between a first capsoloid having a first set of attributes and a second capsoloid having a second set of attributes includes detecting and resolving conflicts between first attribute and second attributes. For example, a conflict can include a capsoloid having one type of angle value with a neighbor having a second type of angle value incompatible with the first type of angle value. Attempts to attach a capsoloid with a neighboring capsoloid having attributes such that the combination will exceed what is allowed in the observation information—or to pair incompatible angles, lengths, shapes, or other such attributes—can be removed from the predicted information without further consideration.

In an implementation, predictive information can be artificially constrained to capsoloids positioned in a subset of the observation information—thereby enabling creation of a "lean model". For example, as illustrated in FIG. 3A, capsoloid 332 could be used to denote the portion of the surface 322 without addition of capsoloids 330 and 334. In a yet further implementation, connections can be made using artificial constructs to link together capsoloids of a lean model. In another implementation, the predictive information can be constrained to a subset of topological information about the observation information representing the control object to form a lean model.

In an implementation, a lean model can be associated with a full predictive model. The lean model (or topological information, or properties described above) can be extracted from the predictive model to form a constraint. Then, the constraint can be imposed on the predictive information thereby enabling the predictive information to be constrained in one or more of behavior, shape, total (system) energy, structure, orientation, compression, shear, torsion, other properties, and/or combinations thereof.

In an implementation, the observation information can include components reflecting portions of the control object which are occluded from view of the device ("occlusions" or "occluded components"). In one implementation, the predictive information can be "fit" to the observation information as described herein above with the additional constraint(s) that some total property of the predictive information (e.g., potential energy) be minimized or maximized (or driven to lower or higher value(s) through iteration or solution). Properties can be derived from nature, properties of the control object being viewed, others, and/or combinations thereof. In another implementation, a deformation of the predictive information can be allowed subject to an overall permitted value of compression, deformation, flexibility, others, and/or combinations thereof.

In one implementation, raw image information and fast lookup table can be used to find a look up region that gives constant time of computation of the closest point on the contour given a position. Fingertip positions are used to compute point(s) on the contour which can be then determined whether the finger is extended or non-extended, according to some implementations. A signed distance function can be used to determine whether points lie outside or inside a hand region, in another implementation. An implementation includes checking to see if points are inside or outside the hand region.

In another implementation, a variety of information types can be abstracted from the 3D solid model of a hand. For example, velocities of a portion of a hand (e.g., velocity of one or more fingers, and a relative motion of a portion of the hand), state (e.g., position, an orientation, and a location of a portion of the hand), pose (e.g., whether one or more fingers are extended or non-extended, one or more angles of bend for one or more fingers, a direction to which one or more fingers point, a configuration indicating a pinch, a grab, an outside pinch, and a pointing finger), and whether a tool or object is present in the hand can be abstracted in various implementations.

In one implementation, the predictive information including the 3D solid model is filtered by applying various constraints based on known (or inferred) physical properties of the system. For example, some solutions would place the object outside the field of view of the cameras, and such solutions can readily be rejected. As another example, in some implementations, the type of object being modeled is known (e.g., it can be known that the object is or is expected to be a human hand). Techniques for determining object type are described below; for now, it is noted that where the object type is known, properties of that object can be used to rule out instances of the 3D solid model where the geometry is inconsistent with objects of that type. For example, human hands have a certain range of sizes and expected eccentricities, and such ranges can be used to filter the solutions in a particular slice. These constraints can be represented in any suitable format, e.g., the 3D solid model, an ordered list of parameters based on such a model, etc. As another example, if it is assumed that the object being modeled is a particular type of object (e.g., a hand), a parameter value can be assumed based on typical dimensions for objects of that type (e.g., an average cross-sectional dimension of a palm or finger). An arbitrary assumption can also be used, and any assumption can be improved or refined through iterative analysis.

In some implementations, known topological information of a control object can also be used to filter (or further filter) the 3D solid model. For example, if the object is known to be a hand, constraints on the spatial relationship between various parts of the hand (e.g., fingers have a limited range of motion relative to each other and/or to the palm of the hand) as represented in a physical model or explicit set of constraint parameters can be used to constrain one iteration of the 3D solid model based on results from other iterations.

In some implementations, multiple 3D solid models can be constructed over time for a control object. It is likely that the "correct" solution (i.e., the 3D solid model that best corresponds to the actual position and/or pose of the object) will interpolate well with other iterations, while any "spurious" solutions (i.e., models that do not correspond to the actual position and/or pose of the object) will not. Incorrect or least correct solutions can be discarded in other implementations.

In a further implementation, the 3D model can be further improved or refined, e.g., based on an identification of the type of object being modeled. In some implementations, a library of object types can be provided (e.g., as object library 248 of FIG. 2). For each object type, the library can provide characteristic parameters for the object in a range of possible poses (e.g., in the case of a hand, the poses can include different finger positions, different orientations relative to the cameras, etc.). Based on these characteristic parameters, a reconstructed 3D model can be compared to various object types in the library. If a match is found, the matching object type is assigned to the model.

Once an object type is determined, the 3D model can be improved or refined using constraints based on characteristics of the object type. For instance, a human hand would characteristically have five fingers (not six), and the fingers would be constrained in their positions and angles relative to each other and to a palm portion of the hand. Any 3D solid subcomponents in the model that are inconsistent with these constraints can be discarded. In some instances, applying type-based constraints can cause deterioration in accuracy of reconstruction if the object is misidentified. (Whether this is a concern depends on implementation, and type-based constraints can be omitted if desired.)

In some implementations, object library 248 can be dynamically and/or iteratively updated. For example, based on characteristic parameters, an object being modeled can be identified as a hand. As the motion of the hand is modeled across time, information from the model can be used to revise the characteristic parameters and/or define additional characteristic parameters, e.g., additional poses that a hand can present.

In some implementations, improvement or refinement can also include correlating results of analyzing images across time. It is contemplated that a series of images can be obtained as the object moves and/or articulates. Since the images are expected to include the same object, information about the object determined from one set of images at one time can be used to constrain the 3D solid model of the object at a later time. (Temporal refinement can also be performed "backward" in time, with information from later images being used to refine analysis of images at earlier times.)

In some implementations, analysis of the next set of images can be informed by results of analyzing previous sets. For example, if an object type was determined, type-based constraints can be applied in the initial 3D solid model construction, on the assumption that successive images are of the same object. In addition, images can be correlated across time, and these correlations can be used to further refine the model, e.g., by rejecting discontinuous jumps in the object's position or subcomponents that appear at one time point but completely disappear at the next.

It will be appreciated that the motion capture process described herein is illustrative and that variations and modifications are possible. Steps described as sequential can be executed in parallel, order of steps can be varied, and steps can be modified, combined, added or omitted. Different mathematical formulations and/or solution procedures can be substituted for those shown herein. Various phases of the analysis can be iterated, as noted above, and the degree to which iterative improvement is used can be chosen based on a particular application of the technology. For example, if motion capture is being used to provide real-time interaction (e.g., to control a computer system), the data capture and analysis should be performed fast enough that the system response feels like real time to the user. Inaccuracies in the model can be tolerated as long as they do not adversely affect the interpretation or response to a user's motion. In other applications, e.g., where the motion capture data is to be used for rendering in the context of digital movie-making, an analysis with more iterations that produces a more refined (and accurate) model can be preferred. As noted above, an object being modeled can be a "complex" object and consequently can present multiple discrete subcomponents in some construction iterations. For example, a hand has fingers, and a 3D solid model for the fingers can include as many as five discrete elements. The analysis techniques described above can be used to model complex objects.

Any type of object can be the subject of motion capture using these techniques, and various aspects of the implementation can be optimized for a particular object. For example, the type and positions of cameras and/or light sources can be optimized based on the size of the object whose motion is to be captured and/or the space in which motion is to be captured. As described above, in some implementations, an object type can be determined based on the 3D model, and the determined object type can be used to add type-based constraints in subsequent phases of the analysis. In other implementations, the motion capture algorithm can be optimized for a particular type of object, and assumptions or constraints pertaining to that object type (e.g., constraints on the number and relative position of fingers and palm of a hand) can be built into the analysis algorithm. This can improve the quality of the reconstruction for objects of that type, although it can degrade performance if an unexpected object type is presented. Depending on implementation, this can be an acceptable design choice. For example, in a system for controlling a computer or other device based on recognition of hand gestures, there may not be value in accurately reconstructing the motion of any other type of object (e.g., if a cat walks through the field of view, it can be sufficient to determine that the moving object is not a hand).

Analysis techniques in accordance with implementations of the technology disclosed can be implemented as algorithms in any suitable computer language and executed on programmable processors. Alternatively, some or all of the algorithms can be implemented in fixed-function logic circuits, and such circuits can be designed and fabricated using conventional or other tools.

Computer programs incorporating various features of the technology disclosed can be encoded on various computer readable storage media; suitable media include magnetic disk or tape, optical storage media such as compact disk (CD) or DVD (digital versatile disk), flash memory, and any other non-transitory medium capable of holding data in a computer-readable form. Computer readable storage media encoded with the program code can be packaged with a compatible device or provided separately from other devices. In addition program code can be encoded and transmitted via wired optical, and/or wireless networks conforming to a variety of protocols, including the Internet, thereby allowing distribution, e.g., via Internet download.

The motion capture methods and systems described herein can be used in a variety of applications. For example, the motion of a hand can be captured and used to control a computer system or video game console or other equipment based on recognizing gestures made by the hand. Full-body motion can be captured and used for similar purposes. In such implementations, the analysis and reconstruction advantageously occurs in approximately real-time (e.g., times comparable to human reaction times), so that the user experiences a natural interaction with the equipment. In other applications, motion capture can be used for digital rendering that is not done in real time, e.g., for computer-animated movies or the like; in such cases, the analysis can take as long as desired. In intermediate cases, detected object shapes and motions can be mapped to a physical model whose complexity is suited to the application—i.e., which provides a desired processing speed given available computational resources. For example, the model can represent generic hands at a computationally tractable level of detail, or can incorporate the user's own hands by initial image capture thereof followed by texture mapping onto a generic hand model. The physical model is manipulated ("morphed") according to the detected object orientation and motion.

Motion data representing free-form gestures performed using a control object can be stored as data units called frames. Frames include information necessary to capture the dynamic nature of the free-form gestures, referred to as "feature sets." Hands and pointables (fingers and tools) are examples of feature sets of a gesture that are described by features directly related to real attributes of the hands and pointables. For instance, a hand can be described by three dimensional values, like: position of center of hand, normal vector, and direction vector pointing from the center to the end of fingers. Similarly, fingers or tools (which are linger and thinner than fingers) can described by a set of features including a position of tip, pointing direction vector, length, and width.

Figure 6A:
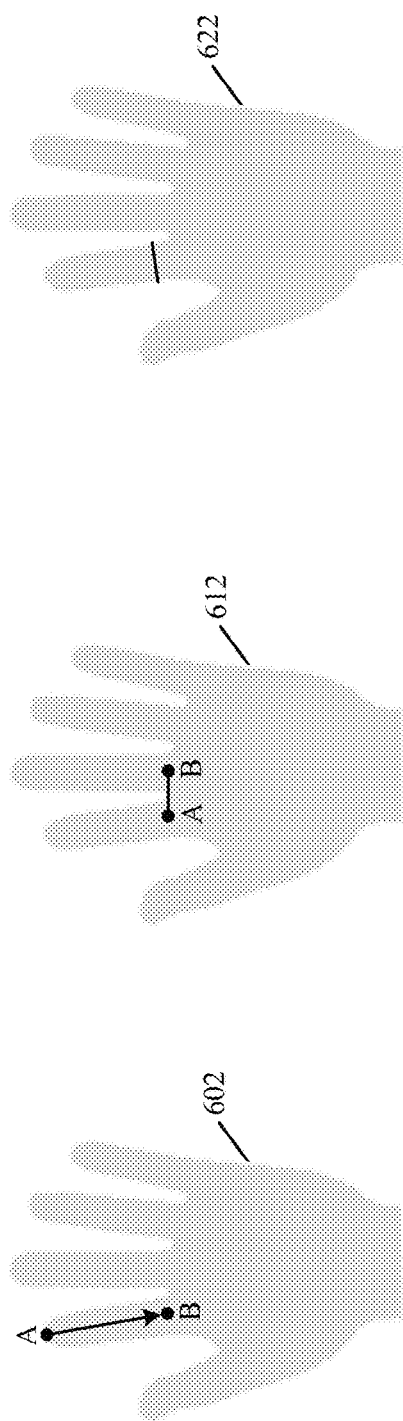
FIG. 6A depicts one implementation of feature sets of a free-form gesture that are described by features directly related to real attributes of a control object.
Figure 6A:
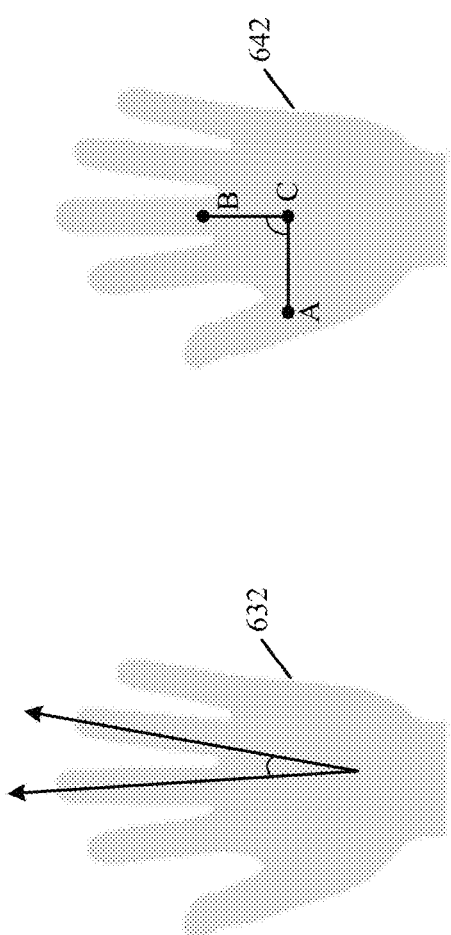

As illustrated in FIG. 6A, several different features of a hand can be determined such that a first feature set can include numbers of fingers in a frame, Euclidean distances between consecutive finger's tips, and absolute angles between consecutive fingers. In another implementation, a second feature can be the first feature set extended by the distances between consecutive finger tips and the position of the hand's palm. In yet another implementation, a third feature set can include features from the second feature set extended by the five angles between fingers and normal of hand's palm.

In one implementation, distance between two nearest base points of a finger is calculated by multiplying a reversed normalized direction vector designated to a finger base point with the length of the finger. Further, the beginning of this vector is placed in the fingertip position and the end of the vector identifies the finger base point, as shown in silhouette 602. Silhouette 612 is an example of distance between two nearest base points of fingers. Silhouette 622 is an implementation depicting the ration of a finger's thickness to the maximal finger's thickness.

According to an implementation presented as silhouette 632, angles between two nearest fingers are determined by determining the angle between finger direction vectors of two consecutive fingers. In another implementation, angles between a particular finger and the first finger relative to palm position are calculated using two fingertip positions and a palm position. After this, the line segments between the palm position, fingertip positions, and the searched angle between two finger segments are identified, as shown in silhouette 642.

In some implementations, a feature set can include features encoding the information about the speed of the hand during a free-form gesture. In one implementation, a recorded displacement of the hand in a rectangular or curvilinear coordinate system can be determined. In one implementation, an object detection module 228 expresses the changing locations of the hand as it traverses a path through a monitored space in Cartesian/(x, y, z) coordinates. According to some implementations, a gestural path of a control object can be entirely defined by its angles in the relative curvilinear coordinates. In one example, if C is a vector representing the control object in the Cartesian coordinate system as C(x, y, z)=(initial point–final point) (x, y, z). Then, transformation to a curvilinear coordinate system can be denoted as C(ρ, θ, φ), where ρ represents the radius of a curve, θ is the azimuth angle of the curve, and φ is the inclination angle of the curve.

The object detection module 228 identifies these coordinates by analyzing the position of the object as captured in a sequence of images. A filtering module receives the Cartesian coordinates, converts the path of the object into a Frenet-Serret space, and filters the path in that space. In one implementation, the filtering module then converts the filtered Frenet-Serret path back into Cartesian coordinates for downstream processing by other programs, applications, modules, or systems.

Frenet-Serret formulas describe the kinematic properties of a particle moving along a continuous, differentiable curve in 3D space. A Frenet-Serret frame is based on a set of orthonormal vectors, which illustrates a path of an object (e.g., a user's hand, a stylus, or any other object) through the monitored space; points are the (x, y, z) locations of the object as identified by the object detection module 228. The filtering module attaches a Frenet-Serret frame of reference to a plurality of locations (which can or may not correspond to the points) on the path. The Frenet-Serret frame consists of (i) a tangent unit vector (T) that is tangent to the path (e.g., the vector T points in the direction of motion), (ii) a normal unit vector (N) that is the derivative of T with respect to an arclength parameter of the path divided by its length, and (iii) a binormal unit vector (B) that is the cross-product of T and N. Alternatively, the tangent vector can be determined by normalizing a velocity vector (as explained in greater detail below) if it is known at a given location on the path. These unit vectors T, N, B collectively form the orthonormal basis in 3D space known as a TNB frame or Frenet-Serret frame. The Frenet-Serret frame unit vectors T, N, B at a given location can be calculated based on a minimum of at least one point before and one point after the given location to determine the direction of movement, the tangent vector, and the normal vector. The binormal vector is calculated as the cross-product of the tangent and normal vectors. Any method of converting the path represented by the points to Frenet-Serret frames is within the scope of the technology disclosed.

Once a reference Frenet-Serret frame has been associated with various points along the object's path, the rotation between consecutive frames can be determined using the Frenet-Serret formulas describing curvature and torsion. The total rotation of the Frenet-Serret frame is the combination of the rotations of each of the three Frenet vectors described by the formulas $$\frac{dT}{ds} = \kappa N, \frac{dN}{ds} = -\kappa T + \tau B, \text{ and } \frac{dB}{ds} = -\tau N,$$

where $$\frac{d}{ds}$$

is the derivative with respect to arclength, κ is the curvature, and τ is the torsion of the curve. The two scalars κ and τ can define the curvature and torsion of a 3D curve, in that the curvature measures how sharply a curve is turning while torsion measures the extent of its twist in 3D space. Alternatively, the curvature and torsion parameters can be calculated directly from the derivative of best-fit curve functions (i.e., velocity) using, for example, the equations $$\kappa = \frac{|\vec{v} \times \vec{a}|}{|\vec{v}|^3} \text{ and } \tau = \frac{(\vec{v} \times \vec{a}) \cdot \vec{a}'}{|\vec{v} \times \vec{a}|^2}.$$

Figure 6B:
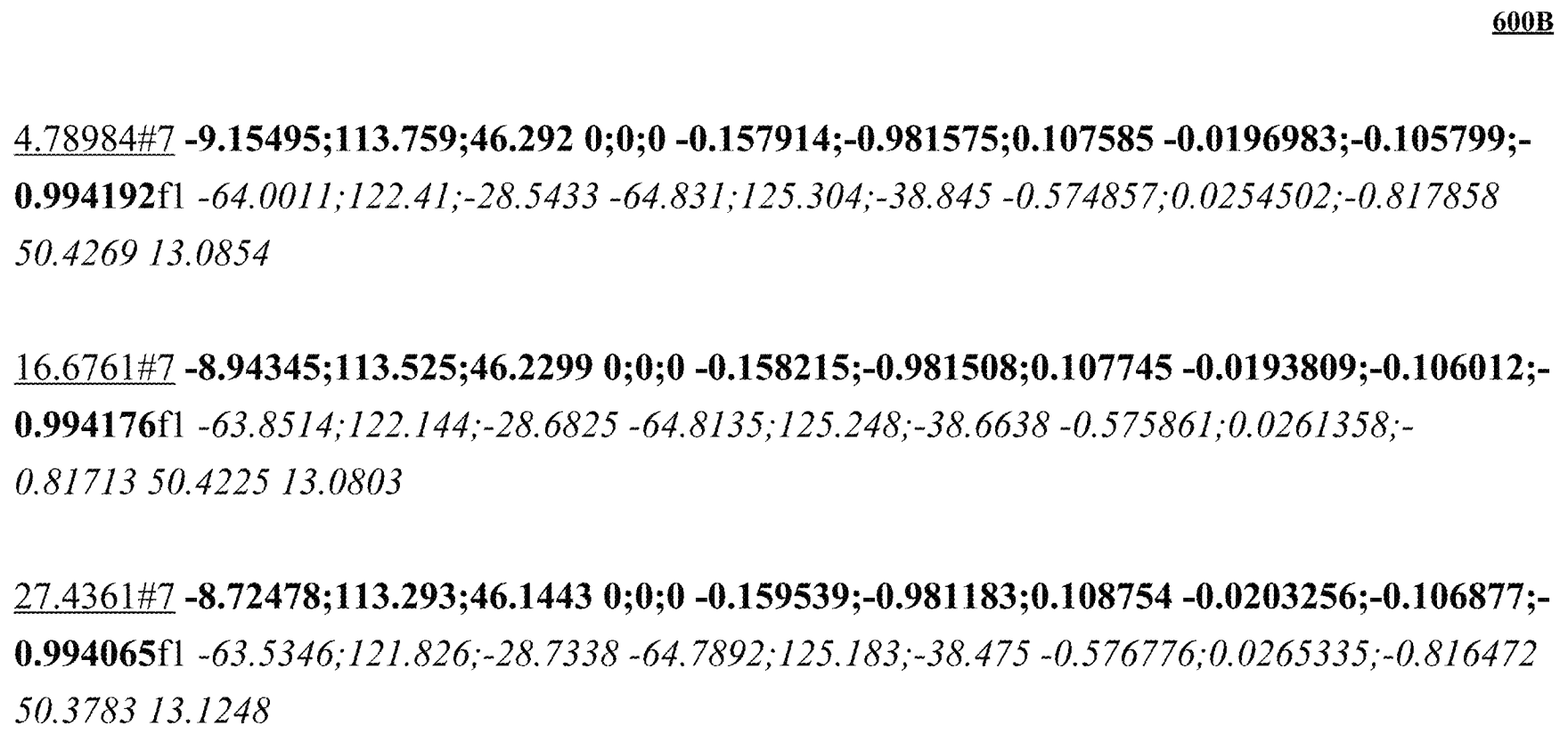

The sequence shown in FIG. 6B is an example representation of gestural data captured for one or more free-form gestures performed using a hand. In the sequence 600B, each line represents a frame and each frame includes a timestamp and hand parameters such as hand id, palm position, stabilized palm position, palm normal, vector, palm direction vector, and detected fingers parameters. Further, the finger parameters include finger id, fingertip position, stabilized tip position, finger direction vector, finger length, and finger width. Again with reference to sequence 600B, underlined text depicts frame timestamp, the bold faced data highlights information about the hand, and the italicized alphanumeric characters identify information about the fingers.

FIG. 9 illustrates an example method 900 of capturing gestural motion of a control object in a 3D sensory space. Flowchart 900 can be implemented by one or more processors configured to receive or retrieve information, process the information, store results, and transmit the results. Other implementations may perform the actions in different orders and/or with different, varying, alternative, modified, fewer or additional actions than those illustrated in FIG. 9. Multiple actions can be combined in some implementations. For convenience, this flowchart is described with reference to the system that carries out a method. The system is not necessarily part of the method.

At action 902, observation information characterizing a surface of a control object is determined from at least one image of a gestural motion of the control object in a three-dimensional (3D) sensory space. In one implementation, determining the observation information further includes fitting a family of closed curves and positions of a plurality of two-dimensional (2D) cross-sectional portions of the control object to the image based at least on a location of at least one image capturing device.

At action 912, a 3D solid model is constructed to represent the control object by fitting one or more 3D solid subcomponents to the characterized surface. In one implementation, fitting the one or more 3D solid subcomponents further includes fitting a set of closed curves to at least a portion of the surface. In some implementations, the closed curves are at least one of radial solids, capsuloids, spheres, ellipsoids, and hyperboloids.

According to one implementation, fitting the one or more 3D solid subcomponents further includes fitting a contour and surface defined by a set of points at a fixed distance from a closest corresponding point on the contour. In another implementation, fitting the one or more 3D solid subcomponents further includes fitting a set of points normal to points on a contour and a fixed distance therefrom. In a further implementation, fitting the one or more 3D solid subcomponents further includes finding a closest point on a contour and projecting outward a set of points at a radius length from the closest point.

In some implementations, when the control object is a hand and fitting the one or more 3D solid subcomponents further includes at least one of fitting capsuloids in finger portions of the surface and fitting radial solids in palm and/or wrist portions of the surface. In other implementations, constructing the 3D solid model further includes selecting a pre-determined 3D solid model from an object library based on characteristic parameters of the control object.

In yet another implementation, constructing the 3D solid model further includes determining the 3D solid subcomponents from physical characteristics of a type of control object being observed. When the control object is a hand and the physical characteristics of the hand include at least one of four fingers and a thumb of the hand, a palm to which the fingers and the thumb are connected, and positions and angles of the fingers and the thumb relative to each other and to the palm. When the control object is a tool and the physical characteristics of the tool include at least one of length of the tool, width of the tool, and pointing direction vector of the tool.

At action 922, the 3D solid model's representation of the gestural motion is improved. In one implementation, improving the 3D solid model's representation of the gestural motion by interpolating the 3D solid model positions across time based on expected continuity in motion and deformation of the control object. In another implementation, the 3D solid model's representation of the gestural motion is improved by detecting fits of 3D solid subcomponents with colliding subcomponents and fitting, to the surface, 3D solid subcomponents with least colliding subcomponents. In some implementations, detection of the colliding subcomponents is based at least on identifying a subcomponent attribute incompatible with an adjacent subcomponent attribute. According to one implementation, the subcomponent attribute is at least one of orientation, angle, length, shape, behavior, total energy, structure, compression, deformation, shear, and torsion.

In a yet another implementation, the 3D solid model's representation of the gestural motion is improved by detecting conflicting attributes between adjacent 3D solid subcomponents and fitting, to the surface, 3D solid subcomponents with least conflicting attributes. In one implementation, the 3D solid subcomponents with conflicting attributes are ranked based on a degree of conflict and presenting the ranked 3D solid subcomponents for selection. Some implementations include the conflicting attributes being at least one of minima and maxima of intersection angles between the 3D solid subcomponents.

At action 932, an error indication is calculated between a point on the characterized surface of the control object and a corresponding point on at least one of the 3D solid subcomponents. In one implementation, determining the error indication further includes determining whether the point on the surface and the corresponding point on the at least one of the 3D solid subcomponents are within a threshold closest distance. In another implementation, determining the error indication further includes pairing point sets on the surface with points on axes of the 3D solid subcomponents, wherein the surface points lie on vectors that are normal to the axes, and determining a reduced root mean squared deviation (RMSD) of distances between paired point sets. In yet another implementation, determining the error indication further includes pairing point sets on the surface with points on the 3D solid subcomponents, wherein normal vectors to the point sets are parallel to each other, and determining a reduced root mean squared deviation (RMSD) of distances between bases of the normal vectors.

Figure 8C:
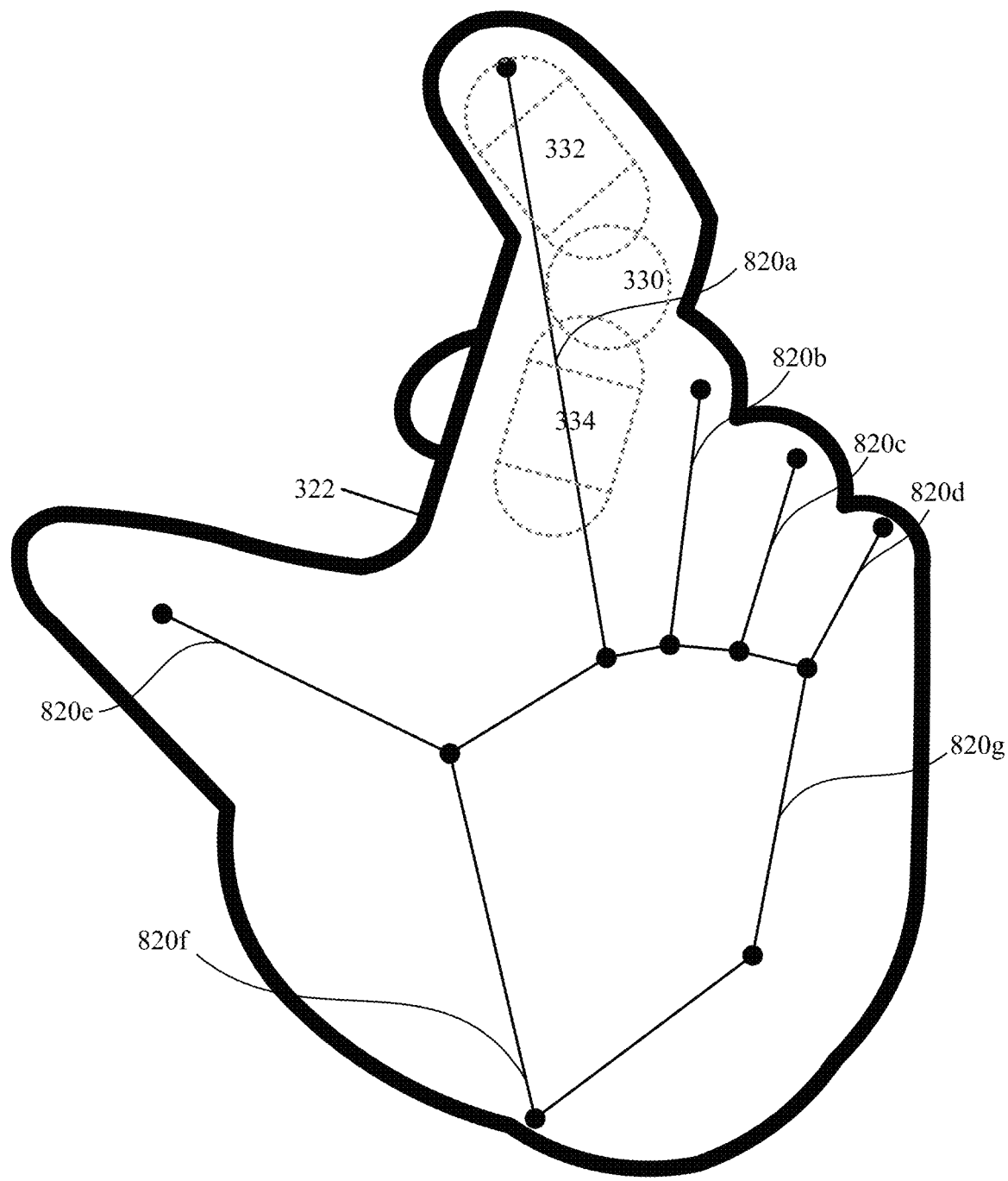
FIGS. 8C and 8D depict graphical illustrations of constraining a 3D solid model using less complex artificial constructs.
Figure 8D:
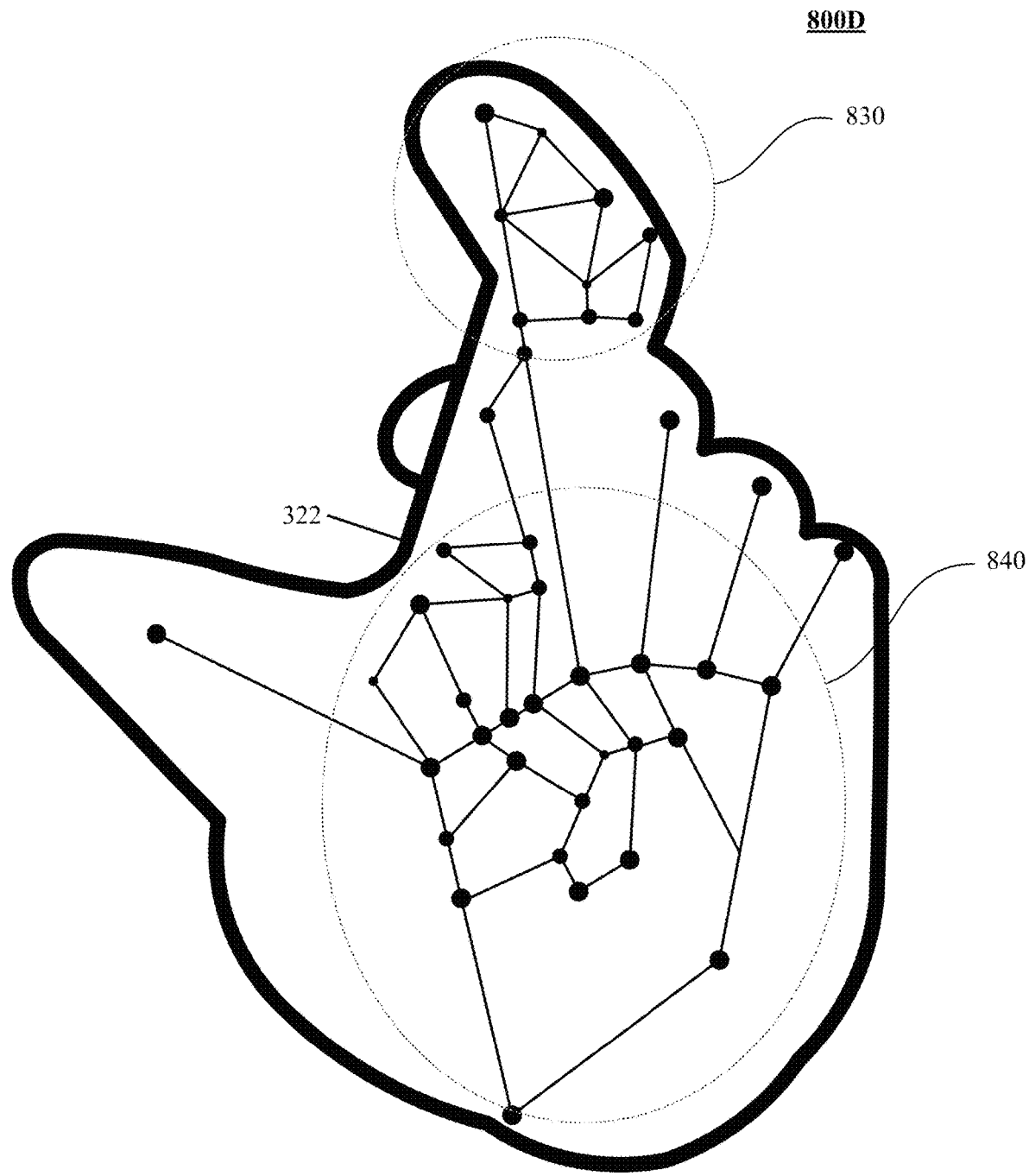

According to one implementation, the one or more 3D solid subcomponents are identified at an extremity of the control object and error indication determination is constrained to the identified extremity subcomponents. In another implementation, the 3D solid subcomponents are linked by representing a plurality of subcomponents using one or more artificial constructs and the error indication determination is constrained to the artificial constructs. For instance, FIGS. 8C and 8D depict graphical illustrations 800A and 800B of constraining a 3D solid model using less complex artificial constructs. In the example shown in FIG. 8C, a group of 3D solid subcomponents 332, 330, and 334 are replaced by artificial constructs 820a-f. In this example, all the artificial constructs 820a-f are line segments. In other implementations, other types of artificial constructs can be used such as different combinations of 1D or 2D solids. In another example shown in FIG. 8D, a surface portion 322 of a hand is represented with a web of artificial constructs and individual portions of the hand such as fingers, carpals, knuckles, palm, wrist, etc. are represented by separate clusters of the artificial constructs, such as clusters 830 and 840. In this example, all the artificial constructs are line segments. In other implementations, other types of artificial constructs can be used such as different combinations of 1D or 2D solids. When the 3D solid subcomponents are fitted to a hand surface, an artificial construct can be a line segment representing finger subcomponents and/or a line, square, circle, or ellipse to representing palm or wrist subcomponents.

At action 942, the 3D solid model is adjusted responsive to the error indication. In one implementation, adjusting the 3D solid model further includes altering the 3D solid subcomponents to conform to at least one of length, width, orientation, and arrangement of portions of the surface. In some implementations, altering the 3D solid subcomponents further includes applying a transformation matrix to a plurality of points on the 3D solid subcomponents. In other implementations, altering the 3D solid subcomponents further includes determining a rotation matrix that provides a reduced root mean squared deviation (RMSD) between paired point sets on the surface and point sets on the 3D solid subcomponents.

Yet other implementations include repeatedly applying the method 900 over time and determining gestural motion of the control object based on differences between 3D solid model positions across time.

This method and other implementations of the technology disclosed can include one or more of the following features and/or features described in connection with additional methods disclosed. Other implementations can include a non-transitory computer readable storage medium storing instructions executable by a processor to perform any of the methods described above. Yet another implementation can include a system including memory and one or more processors operable to execute instructions, stored in the memory, to perform any of the methods described above.

FIG. 10 is a representative method 1000 of accurately capturing gestural motion of a control object in a three-dimensional 3D sensory space. Flowchart 1000 can be implemented by one or more processors configured to receive or retrieve information, process the information, store results, and transmit the results. Other implementations may perform the actions in different orders and/or with different, varying, alternative, modified, fewer or additional actions than those illustrated in FIG. 10. Multiple actions can be combined in some implementations. For convenience, this flowchart is described with reference to the system that carries out a method. The system is not necessarily part of the method.

At action 1002, observation information characterizing gestural motion of a control object in a three-dimensional (3D) sensory space is determined from at least one image captured at time t0. In one implementation, determining the observation information further includes fitting a family of closed curves and positions of a plurality of two-dimensional (2D) cross-sectional portions of the control object to the image based at least on a location of at least one image capturing device.

At action 1012, a 3D solid model is constructed to represent the control object by fitting one or more 3D solid subcomponents to a construct of the control object defined by the observation information based on the image captured at time t0. In one implementation, fitting the one or more 3D solid subcomponents further includes fitting a set of closed curves to at least a portion of the construct. In some implementations, the closed curves are at least one of radial solids, capsuloids, spheres, ellipsoids, and hyperboloids.

According to one implementation, fitting the one or more 3D solid subcomponents further includes fitting a contour and construct defined by a set of points at a fixed distance from a closest corresponding point on the contour. In another implementation, fitting the one or more 3D solid subcomponents further includes fitting a set of points normal to points on a contour and a fixed distance therefrom. In a further implementation, fitting the one or more 3D solid subcomponents further includes finding a closest point on a contour and projecting outward a set of points at a radius length from the closest point.

In some implementations, when the control object is a hand and fitting the one or more 3D solid subcomponents further includes at least one of fitting capsuloids in finger portions of the construct and fitting radial solids in palm and/or wrist portions of the construct. In other implementations, constructing the 3D solid model further includes selecting a pre-determined 3D solid model from an object library based on characteristic parameters of the control object.

In yet another implementation, constructing the 3D solid model further includes determining the 3D solid subcomponents from physical characteristics of a type of control object being observed. When the control object is a hand and the physical characteristics of the hand include at least one of four fingers and a thumb of the hand, a palm to which the fingers and the thumb are connected, and positions and angles of the fingers and the thumb relative to each other and to the palm. When the control object is a tool and the physical characteristics of the tool include at least one of length of the tool, width of the tool, and pointing direction vector of the tool.

At action 1022, conformance of the 3D solid model to the modified observation information is improved responsive to modifications in the observation information based on another image captured at time t1, when the control object moved between t0 and t1. In one implementation, improving the 3D solid model's representation of the gestural motion by interpolating the 3D solid model positions across time based on expected continuity in motion and deformation of the control object. In another implementation, the 3D solid model's representation of the gestural motion is improved by detecting fits of 3D solid subcomponents with colliding subcomponents and fitting, to the construct, 3D solid subcomponents with least colliding subcomponents. In some implementations, detection of the colliding subcomponents is based at least on identifying a subcomponent attribute incompatible with an adjacent subcomponent attribute. According to one implementation, the subcomponent attribute is at least one of orientation, angle, length, shape, behavior, total energy, structure, compression, deformation, shear, and torsion.

In a yet another implementation, the 3D solid model's representation of the gestural motion is improved by detecting conflicting attributes between adjacent 3D solid subcomponents and fitting, to the construct, 3D solid subcomponents with least conflicting attributes. In one implementation, the 3D solid subcomponents with conflicting attributes are ranked based on a degree of conflict and presenting the ranked 3D solid subcomponents for selection. Some implementations include the conflicting attributes being at least one of minima and maxima of intersection angles between the 3D solid subcomponents.

At action 1032, an error indication is calculated between a point on another construct of the control object defined by the observation information based on the image captured at time t1 and a corresponding point on at least one of the 3D solid subcomponents fitted to the construct defined by the observation information based on the image captured at time t0. In one implementation, determining the error indication further includes determining whether the point on the construct and the corresponding point on the at least one of the 3D solid subcomponents are within a threshold closest distance. In another implementation, determining the error indication further includes pairing point sets on the construct with points on axes of the 3D solid subcomponents, wherein the construct points lie on vectors that are normal to the axes, and determining a reduced root mean squared deviation (RMSD) of distances between paired point sets. In yet another implementation, determining the error indication further includes pairing point sets on the construct with points on the 3D solid subcomponents, wherein normal vectors to the point sets are parallel to each other, and determining a reduced root mean squared deviation (RMSD) of distances between bases of the normal vectors.

According to one implementation, the one or more 3D solid subcomponents are identified at an extremity of the control object and error indication determination is constrained to the identified extremity subcomponents. In another implementation, the 3D solid subcomponents are linked by representing a plurality of subcomponents using one or more artificial constructs and the error indication determination is constrained to the artificial constructs. When the 3D solid subcomponents are fitted to a hand construct, an artificial construct can be a line segment representing finger subcomponents and/or a square, circle, or ellipse to representing palm subcomponents.

At action 1042, the 3D solid model is adjusted responsive to the error indication. In one implementation, adjusting the 3D solid model further includes altering the 3D solid subcomponents to conform to at least one of length, width, orientation, and arrangement of portions of the construct. In some implementations, altering the 3D solid subcomponents further includes applying a transformation matrix to a plurality of points on the 3D solid subcomponents. In other implementations, altering the 3D solid subcomponents further includes determining a rotation matrix that provides a reduced root mean squared deviation (RMSD) between paired point sets on the construct and point sets on the 3D solid subcomponents.

Yet other implementations include repeatedly applying the method 1000 over time and determining gestural motion of the control object based on differences between 3D solid model positions across time.

This method and other implementations of the technology disclosed can include one or more of the following features and/or features described in connection with additional methods disclosed. Other implementations can include a non-transitory computer readable storage medium storing instructions executable by a processor to perform any of the methods described above. Yet another implementation can include a system including memory and one or more processors operable to execute instructions, stored in the memory, to perform any of the methods described above.

The terms and expressions employed herein are used as terms and expressions of description and not of limitation, and there is no intention, in the use of such terms and expressions, of excluding any equivalents of the features shown and described or portions thereof. In addition, having described certain implementations of the technology disclosed, it will be apparent to those of ordinary skill in the art that other implementations incorporating the concepts disclosed herein can be used without departing from the spirit and scope of the technology disclosed. Accordingly, the described implementations are to be considered in all respects as only illustrative and not restrictive.

What is claimed is:

1. A method of accurately capturing gestural motion of a control object in a three-dimensional (3D) sensory space, the method including:
    determining observation information characterizing gestural motion of a control object in a three-dimensional (3D) sensory space from at least one image captured at time t0, the determining of the observation information including:
        identifying a contour of the control object, the identified contour having a plurality of contour points;
        identifying a first unmatched contour point of the plurality of contour points;
        determining a normal for the first unmatched contour point;
        identifying a second unmatched contour point of the plurality of contour points by locating an unmatched contour point that is closest to the first unmatched contour point and is reachable by a line having a most opposite normal to the normal for the first unmatched contour point;
        defining a span as a shortest distance between the first unmatched contour point and the second unmatched contour point;
        defining a span length as a length of the defined span; and
        determining the observation information to include the defined span and the defined span length;
    constructing a 3D solid model to represent the control object by fitting one or more 3D solid subcomponents to a construct of the control object defined by the observation information based on the image captured at time t0; and
    responsive to modifications in the observation information based on another image captured at time t1, wherein the control object moved between t0 and t1, improving conformance of the 3D solid model to the modifications in the observation information.

2. The method of claim 1, wherein the fitting of the one or more 3D solid subcomponents further includes fitting a set of closed curves to at least a portion of a construct of the control object.

3. The method of claim 2, wherein the set of closed curves includes at least one of radial solids, capsuloids, spheres, ellipsoids, and hyperboloids.

4. The method of claim 1, wherein the fitting of the one or more 3D solid subcomponents further includes fitting a set of capsuloids to at least a portion of construct of the control object.

5. The method of claim 1, wherein the control object is a hand and the fitting the one or more 3D solid subcomponents further includes at least one of:
    fitting capsuloids to finger portions of a construct of the control object; and
    fitting radial solids to palm and/or wrist portions of the construct.

6. The method of claim 1, wherein the improving of the conformance of the 3D solid model includes altering the 3D solid subcomponents to conform to at least one of the defined span length, width, orientation, and arrangement of portions of a construct of the control object.

7. The method of claim 6, wherein the altering of the 3D solid subcomponents further includes applying a transformation matrix to a plurality of points on the 3D solid subcomponents.

8. The method of claim 1, wherein the constructing of the 3D solid model further includes determining the 3D solid subcomponents from physical characteristics of a type of control object being observed.

9. The method of claim 8, wherein the control object is a hand and the physical characteristics of the hand include at least one of:
    four fingers and a thumb of the hand;
    a palm to which the fingers and the thumb are connected; and
    positions and angles of the fingers and the thumb relative to each other and to the palm.

10. The method of claim 8, wherein the control object is a tool and the physical characteristics of the tool include at least one of:
    length of the tool;
    width of the tool; and
    pointing direction vector of the tool.

11. The method of claim 1, wherein the control object is a hand and identified construct portions include at least one fingers, carpals, knuckles, palm, and wrist.

12. The method of claim 1, further including improving a 3D solid model's representation of the gestural motion by:
    detecting conflicting attributes between adjacent 3D solid subcomponents based on the defined span and the defined span length; and
    fitting, to the construct, 3D solid subcomponents with least conflicting attributes.

13. The method of claim 12, further including:
    ranking the 3D solid subcomponents with conflicting attributes based on a degree of conflict; and presenting the ranked 3D solid subcomponents for selection.

14. The method of claim 1, wherein the first unmatched contour point is arbitrarily identified.

15. The method of claim 1, wherein the line is a convex curve line.

16. The method of claim 1, wherein the span is defined as a shortest convex curve between the first unmatched contour point and the second unmatched contour point.

17. The method of claim 1, wherein the normal for the first unmatched contour point is determined by:
   identifying a set of contour points proximate to the first unmatched contour point, wherein at least two contour points included in the set of contour points are not co-linear; and
   determining the normal by obtaining a cross product of the set of points.

18. The method of claim 1, wherein the normal for the first unmatched contour point is determined by:
   identifying a set of contour points proximate to the first unmatched contour point;
   defining a first vector by subtracting a first contour point in the set of contour points from a second contour point in the set of contour points;
   applying a rotation matrix to rotate the first vector by 90 degrees away from a center of mass of the set of contour points; and
   determining the rotated first vector to be the normal.

19. A non-transitory computer readable storage medium impressed with computer program instructions to accurately capture gestural motion of a control object in a three-dimensional (3D) sensory space, which computer program instructions, when executed on a processor, implement a method including:
   determining observation information characterizing gestural motion of a control object in a three-dimensional (3D) sensory space from at least one image captured at time t0, the determining of the observation information including:
      identifying a contour of the control object, the identified contour having a plurality of contour points;
      identifying a first unmatched contour point of the plurality of contour points;
      determining a normal for the first unmatched contour point;
      identifying a second unmatched contour point of the plurality of contour points by locating an unmatched contour point that is closest to the first unmatched contour point and is reachable by a line having a most opposite normal to the normal for the first unmatched contour point;
      defining a span as a shortest distance between the first unmatched contour point and the second unmatched contour point;
      defining a span length as a length of the defined span; and
      determining the observation information to include the defined span and the defined span length;
   constructing a 3D solid model to represent the control object by fitting one or more 3D solid subcomponents to a construct of the control object defined by the observation information based on the image captured at time t0; and
   responsive to modifications in the observation information based on another image captured at time t1, wherein the control object moved between t0 and t1, improving conformance of the 3D solid model to the modifications in the observation information.

20. A system to accurately capture gestural motion of a control object in a three-dimensional (3D) sensory space, comprising:
   a processor and a computer readable storage medium storing computer instructions configured to cause the processor to:
      determine observation information characterizing gestural motion of a control object in a three-dimensional (3D) sensory space from at least one image captured at time t0, the determining of the observation information including:
         identify a contour of the control object, the identified contour having a plurality of contour points;
         identify a first unmatched contour point of the plurality of contour points;
         determine a normal for the first unmatched contour point;
         identify a second unmatched contour point of the plurality of contour points by locating an unmatched contour point that is closest to the first unmatched contour point and is reachable by a line having a most opposite normal to the normal for the first unmatched contour point;
         define a span as a shortest distance between the first unmatched contour point and the second unmatched contour point;
         define a span length as a length of the defined span; and
         determine the observation information to include the defined span and the defined span length;
      construct a 3D solid model to represent the control object by fitting one or more 3D solid subcomponents to a construct of the control object defined by the observation information based on the image captured at time t0; and
      responsive to modifications in the observation information based on another image captured at time t1, wherein the control object moved between t0 and t1, improve conformance of the 3D solid model to the modifications in the observation information.

\* \* \* \* \*

UNITED STATES PATENT AND TRADEMARK OFFICE
CERTIFICATE OF CORRECTION

PATENT NO. : 11,461,966 B1
APPLICATION NO. : 17/100786
DATED : October 4, 2022
INVENTOR(S) : Kevin A Horowitz and David S Holz It is certified that error appears in the above-identified patent and that said Letters Patent is hereby corrected as shown below:

In the Claims

In Claim 1, at Column 33, Line 45, after "time" change "to" to --t0--.

Signed and Sealed this
Twelfth Day of September, 2023

*Katherine Kelly Vidal*

Katherine Kelly Vidal
*Director of the United States Patent and Trademark Office*